US008524247B2

(12) United States Patent
Wu et al.

(10) Patent No.: US 8,524,247 B2
(45) Date of Patent: Sep. 3, 2013

(54) RABIES VIRUS-BASED RECOMBINANT IMMUNOCONTRACEPTIVE COMPOSITIONS AND METHODS OF USE

(75) Inventors: Xianfu Wu, Atlanta, GA (US); Charles Rupprecht, Lawrenceville, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 6 days.

(21) Appl. No.: 13/062,680

(22) PCT Filed: Aug. 20, 2009

(86) PCT No.: PCT/US2009/054502

§ 371 (c)(1),
(2), (4) Date: Mar. 7, 2011

(87) PCT Pub. No.: WO2010/033337

PCT Pub. Date: Mar. 25, 2010

(65) Prior Publication Data

US 2011/0165189 A1 Jul. 7, 2011

Related U.S. Application Data

(60) Provisional application No. 61/097,748, filed on Sep. 17, 2008.

(51) Int. Cl.
*A61K 39/12* (2006.01)
*C12N 7/01* (2006.01)
*A61P 37/00* (2006.01)

(52) U.S. Cl.
USPC .................................... 424/205.1; 435/235.1

(58) Field of Classification Search
None
See application file for complete search history.

(56) References Cited

U.S. PATENT DOCUMENTS

| | | | |
|---|---|---|---|
| 4,608,251 A | 8/1986 | Mia | |
| 5,403,586 A | 4/1995 | Russell-Jones et al. | |
| 5,484,592 A | 1/1996 | Meloen et al. | |
| 5,759,551 A | 6/1998 | Ladd et al. | |
| 6,027,727 A | 2/2000 | Harris et al. | |
| 6,284,733 B1 | 9/2001 | Meloen et al. | |
| 6,911,206 B1 | 6/2005 | Campos et al. | |
| 2002/0131981 A1 | 9/2002 | Dietzschold et al. | |
| 2003/0099671 A1* | 5/2003 | Fu | 424/224.1 |
| 2003/0113346 A1* | 6/2003 | Dietzchold et al. | 424/204.1 |
| 2004/0191266 A1 | 9/2004 | Miller et al. | |
| 2004/0202674 A1 | 10/2004 | Brown et al. | |
| 2005/0239701 A1* | 10/2005 | Baker et al. | 514/12 |
| 2006/0013821 A1 | 1/2006 | Miller et al. | |

FOREIGN PATENT DOCUMENTS

| | | |
|---|---|---|
| WO | WO 88/05308 | 7/1988 |
| WO | WO 93/25231 | 12/1993 |
| WO | WO 94/11019 | 5/1994 |
| WO | WO 2006/017276 A2 | 2/2006 |
| WO | WO 2007/047459 A1 | 4/2007 |

OTHER PUBLICATIONS

Smith et al. (Virology. 2006; 353: 344-356).*

Bradley et al., "Vaccines for Fertility Regulation of Wild and Domestic Species," *J. Biotechnol.*, 73:91-101, 1999.

Brown et al., "Evidence for a Long-Lasting Single Administration Contraceptive Vaccine in Wild Grey Seals," *J. Reprod. Immunol.* vol. 35:43-51, 1997.

Brown et al., "Temporal Trends in Antibody Production in Captive Grey, Harp and Hooded Seals to a Single Administration Immunocontraceptive Vaccine," *J. Reprod. Immunol.*, vol. 35:53-64, 1997.

Cat Contraceptive Vaccine Status, available online at http://www.vetmed.vt.edu/research/cmmid/docs/contravaccine.pdf, 2 pages, Jun. 2006.

Choudhury et al., "Feasibility and Challenges in the Development of Immunocontraceptive Vaccine Based on Zona Pellucida Glycoproteins," *Society of Reproduction and Fertility Supplement*, vol. 63:479-493, 2007.

Cooper and Larsen, "Immunocontraception of Mammalian Wildlife: Ecological and Immunogenetic Issues," *Reproduction*, vol. 132:821-828, 2006.

Delves et al., "Antifertility Vaccines," *Trends Immunol.* vol. 23:213-219, 2002.

Dietzschold et al., "Characterization of an Antigenic Determinant of the Glycoprotein that Correlates with Pathogenicity of Rabies Virus," *Proc. Natl. Acad. Sci.*, vol. 80:70-74, 1983.

Gorman et al., "Evaluation of a Porcine Zona Pellucida Vaccine for the Immunocontraception of Domestic Kittens (*Felis catus*)," *Theriogenology*, vol. 58:135-149, 2002.

Gupta, et al., "Molecular Characterization of Zona Pellucida Glycoproteins: Role in Fertilization and Regulation of Fertility," available online at http://www.nii.res.in/res-reports-2004/resrep043.pdf, 4 pages, Jun. 28, 2006.

Gupta et al., "Potential of Canine Zona Pellucida Glycoproteins-Based Immunocontraceptive Vaccines," Proc. Third Intl. Symp. On Non-Surgical Contraceptive Methods for Pet Population Control, available online at www.acc-d.org, Nov. 10, 2006.

Hardy and Mobbs, "Expression of Recombinant Mouse Sperm Protein sp56 and Assessment of Its Potential for Use as an Antigen in an Immunocontraceptive Vaccine," *Mol. Reprod. Dev.*, vol. 52(2):216-224, 1999.

Hardy et al., "Mouse-specific immunocontraceptive polyepitope vaccines," *Reproduction Supplement* 60:19-30, 2002.

(Continued)

*Primary Examiner* — Shanon A Foley
(74) *Attorney, Agent, or Firm* — Klarquist Sparkman, LLP

(57) ABSTRACT

Described herein are recombinant rabies viruses comprising a heterologous nucleic acid sequence encoding an immunocontraceptive protein, such as gonadotropin-releasing hormone (GnRH) or zona pellucida 3 (ZP3). The recombinant rabies viruses disclosed herein are recovered by reverse genetics, replicate efficiently, elicit rabies virus neutralizing antibodies and immunocontraceptive peptide-specific antibodies in vaccinated animals, and protect vaccinated animals against wild-type rabies virus challenge. Further provided is a method of immunizing a non-human animal against rabies virus infection and simultaneously inhibiting fertility of the animal, comprising administering an immunogenic composition comprising one or more of the recombinant rabies viruses described herein.

18 Claims, 10 Drawing Sheets

(56) References Cited

OTHER PUBLICATIONS

Ivanovo et al., "Contraceptive Potential of Porcine Zona Pellucida in Cats," *Theriogenology*, vol. 43:969-981, 1995.
Miller, "Immunocontraception and Possible Application in Wildlife Damage Management," Wildlife Damage Management, Internet Center for Great Plains Wildlife Damage Control Workshop Proceedings, University of Nebraska—Lincoln, available online at http://digitalcommons.unl.edu/gpwdcwp/445, 1995.
Naz et al., "Recent Advances in Contraceptive Vaccine Development: A Mini-Review," *Hum. Reprod.*, vol. 20(12):3271-3283, 2005.
O'Hern et al., "Colinear Synthesis of an Antigen-Specific B-cell Epitope with a 'Promiscuous' Tetanus Toxin T-cell Epitope: A Synthetic Peptide Immunocontraceptive," *Vaccine*, vol. 16(15):1761-1766, 1997.
O'Rand et al., "Reversible Immunocontraception in Male Monkeys Immunized with Eppin," Science, vol. 306:1189-1190, 2004.
Rath et al., "Characterization of Immune Response in Mice to Plasmid DNA Encoding Dog Zona Pellucida Glycoprotein-3," *Vaccine*, vol. 21:1913-1923, 2003.
Tuffereau et al., "Arginine or Lysine in Position 333 of ERA and CVS Glycoprotein is Necessary for Rabies Virulence in Adult Mice," *Virol.*, vol. 172:206-212, 1989.
Wu and Rupprecht, "Glycoprotein Gene Relocation in Rabies Virus," *Virus Res.* vol. 131:95-99, 2008.
Wu et al., "Both Viral Transcription and Replication are Reduced when the Rabies Virus Nucleoprotein is not Phosphorylated," *J. Virol.*, vol. 76(9):4153-4161, 2002.
Wu et al., "Are All Lyssavirus Genes Equal for Phylogenetic Analyses?" *Virus Res.*, vol. 129:91-103, 2007.
Yamada et al., "Multigenic Relation to the Attenuation of Rabies Virus," *Microbiol. Immunol.*, vol. 50(1):25-32, 2006.
Zhu and Naz, "Fertilization Antigen-1: cDNA Cloning, Testis-Specific Expression, and Immunocontraceptive Effects," *Proc. Natl. Acad. Sci.*, vol. 94:4704-4709, 1997.

* cited by examiner

| Virus # | Description |
|---|---|
| 1 | N-P-M-G3-DZP3-L |
| 2 | N-P-DZP3-M-G3-L |
| 3 | N-G3-P-M--DZP3-L |
| 4 | N-G3-P-M-DZP3/2GnRH-L |
| 5 | N-P-M--G3/GnRH-L |
| 6 | N-P-G3/GnRH-M-L |
| 7 | N-G3-GnRH-P-M-L |
| 8 | N-G3/2GnRH-P-M-L |
| 9 | N-G3/2GnRH-P-M-DZP3/2GnRH-L |

|  | Ecto- | antigenic epitopes | Ecto- |  |  |
|---|---|---|---|---|---|
| SP | II  IIa  WB+ | III | TM  CT | | Glycoprotein |

GnRH   √   ×   √   ×     ×   √

2 GnRH   √   ×   ×   ×     ×   N/T

3' | N | G* | P | M | L | 5' ERAg3p genome

| SP | II | IIa | WB+ | III | TM | CT |

↓ ↓ ↓

ERA-N-GnRH     ERA-IIa-GnRH     ERA-C-GnRH ⎤
ERA-N-2GnRH                                                                               ⎦ Recovered viruses One step virus growth curve

- ERA-N-GnRH
- ERA-N-2GnRH
- ERA-IIa-GnRH
- ERA-C-GnRH

RABIES VIRUS-BASED RECOMBINANT IMMUNOCONTRACEPTIVE COMPOSITIONS AND METHODS OF USE

CROSS REFERENCE TO RELATED APPLICATIONS

This is the U.S. National Stage of International Application No. PCT/US2009/054502, filed Aug. 20, 2009, which was published in English under PCT Article 21(2), which in turn claims the benefit of U.S. Provisional Application No. 61/097,748, filed Sep. 17, 2008, which is herein incorporated by reference in its entirety.

FIELD

This disclosure concerns recombinant rabies viruses as immunocontraceptive compositions for control of wild and domestic animal population growth, as well as protection of animals against rabies virus infection.

BACKGROUND

Rabies is a major threat to public health, causing between 50,000 and 60,000 human deaths each year (World Health Organization, April 2003). Humans get infected with the rabies virus mostly through bites from rabid domestic and wildlife animals. In developing countries, dogs are responsible for about 94% of human rabies deaths. Dog rabies is still epizootic in most countries of Africa, Asia and South America, and in these countries dogs are responsible for most human deaths from the disease. Controlling rabies virus infection in domestic and wildlife animals, therefore, not only reduces the mortality in these animals but also reduces the risks of human exposure.

The rabies virus is transmitted through broken skin by the bite or scratch of an infected animal. Exposure to rabies virus results in its penetration of peripheral, unmyelinated nerve endings, followed by spreading through retrograde axonal transport, replication occurring exclusively in the neurons, and finally arrival in the central nervous system (CNS). Infection of the CNS causes cellular dysfunction and death (Rupprecht and Dietzschold, *Lab Invest.* 57:603, 1987). Since rabies virus spreads directly from cell to cell, it largely evades immune recognition (Clark and Prabhakar, Rabies, In: Olson et al., eds., "Comparative Pathology of Viral Disease," 2:165, Boca Raton, Fla., CRC Press, 1985).

Population control of dogs with outdated methods of capture, restraint and euthanasia are inhumane and not acceptable to the public. Canine rabies prevention and control, and appropriate population management of free-ranging dogs are paramount for eventual disease elimination. Various approaches have been proposed to interrupt canine reproductive cycles, including surgical spay/neuter of animals, chemical sterilization, and immunocontraception. For example, gonadotropin releasing hormone (GnRH) has been considered as one approach as an immunocontraceptive peptide for dogs. However, studies to date have shown that GnRH needs to be synthesized and conjugated with a carrier protein (or adjuvant) to be immunogenic. Necessary scale-up of production may become problematic to meet the regulatory and economic demands for modern vaccine supply. Thus, it is desirable to construct a vaccine that can induce appropriate dual immunological responses against both rabies virus and immunocontraceptive targets, after a single administration in animals.

Moreover, over the past 30 years, immunocontraceptive studies have not generated a single commercial product. Technical limitations are one of the main factors. Therefore, there is a long unfelt need for a novel rabies virus vaccine, engineered with the ability to express a suitable immunocontraceptive gene. This type of vaccine would be an ideal candidate for both rabies prevention and population control of wild and domestic animals, including dogs.

SUMMARY OF THE DISCLOSURE

Recombinant rabies viruses comprising heterologous nucleic acid sequences encoding immunocontraceptive proteins are disclosed herein. The recombinant rabies viruses are recovered using reverse genetics, replicate efficiently in culture, and elicit high titers of rabies virus neutralizing antibodies, elicit immunocontraceptive protein-specific antibodies and confer protection against rabies virus challenge in vaccinated animals.

Provided herein is a recombinant rabies virus in which the genome of the recombinant rabies virus includes a heterologous nucleic acid sequence encoding an immunocontraceptive protein. In some embodiments, the immunocontraceptive protein is gonadotropin-releasing hormone (GnRH) or zona pellucida 3 (ZP3), such as dog ZP3. In some embodiments, the genome of the recombinant rabies virus comprises a nucleic acid sequence encoding ZP3 and a nucleic acid sequence encoding GnRH.

Also provided are immunogenic compositions comprising one or more of the recombinant rabies viruses described herein. Further provided is an immunogenic composition comprising a first recombinant rabies virus and a second recombinant rabies virus, wherein the genome of the first recombinant rabies virus comprises a GnRH nucleic acid sequence and the genome of the second recombinant rabies virus comprises a ZP3 nucleic acid sequence.

Further provided are methods of immunizing a non-human animal against rabies virus infection and inhibiting fertility of the animal, by administering to the animal a therapeutically effective amount of an immunogenic composition comprising one or more of the recombinant rabies viruses disclosed herein.

The foregoing and other features and advantages will become more apparent from the following detailed description of several embodiments, which proceeds with reference to the accompanying figures.

SEQUENCE LISTING

Figure 1:
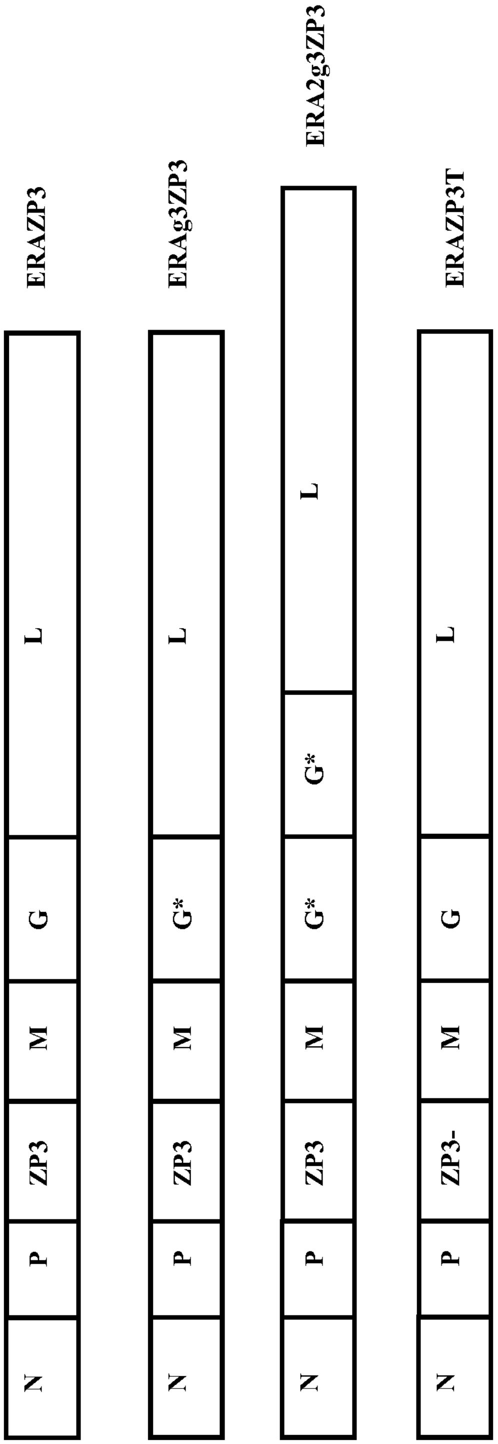
FIG. 1 is a schematic depiction of four recombinant ERAZP3 viruses. G* denotes the mutation at amino acid 333 of glycoprotein (G). ZP—indicates a dog zona pellucida gene.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Feb. 28, 2011, 158 KB, which is incorporated by reference herein. In the accompanying sequence listing:

SEQ ID NO: 1 is the nucleotide sequence of recombinant rabies virus ERA recovered by reverse genetics. Mutation of nucleotides 4370-4372 from aga to gag introduces an Arg to Glu amino acid change in the G protein.

SEQ ID NO: 2 is the amino acid sequence of the rabies virus ERA N protein.

SEQ ID NO: 3 is the amino acid sequence of the rabies virus ERA P protein.

SEQ ID NO: 4 is the amino acid sequence of the rabies virus ERA M protein.

SEQ ID NO: 5 is the amino acid sequence of the rabies virus ERA G protein. An Arg to Glu change at amino acid residue 352 is an attenuating mutation.

SEQ ID NO: 6 is the amino acid sequence of the rabies virus ERA L protein.

SEQ ID NOs: 7 and 8 are the nucleotide and amino acid sequences, respectively, of dog zona pellucida 3 (ZP3).

SEQ ID NOs: 9-26 are the nucleotide sequences of the oligonucleotides use to generate fragment A of dog ZP3.

SEQ ID NOs: 27-46 are nucleotide sequences of the oligonucleotides used to generate fragment B of dog ZP3.

SEQ ID NOs: 47 and 48 are the nucleotide and amino acid sequences, respectively, of GnRH.

SEQ ID NOs: 49 and 50 are the nucleotide and amino acid sequences, respectively, of rabies virus ERA G protein with a single copy of GnRH inserted immediately following the 19 amino acid G protein signal sequence. This construct is referred to as G-N-GnRH.

SEQ ID NOs: 51 and 52 are the nucleotide and amino acid sequences, respectively, of rabies virus ERA G protein with two copies of GnRH inserted immediately following the 19 amino acid G protein signal sequence. This construct is referred to as G-N-2GnRH.

SEQ ID NOs: 53 and 54 are the nucleotide and amino acid sequences, respectively, of rabies virus ERA G protein with a single copy of GnRH inserted immediately following amino acid 221 of the G protein (IIa site). This construct is referred to as GnRH-p3 or G-IIa-GnRH.

SEQ ID NO: 55 is the amino acid sequence of GnRH peptide 1780.

SEQ ID NO: 56 is the amino acid sequence of GnRH peptide 1781.

SEQ ID NO: 57 is the nucleotide sequence of 2GnRH (two tandem copies of the GnRH coding sequence).

SEQ ID NOs: 58 and 59 are the nucleotide sequences of primers used for insertion of the GnRH coding sequence into the rabies virus G gene.

SEQ ID NOs: 60 and 61 are the nucleotide sequences of primers used for insertion of the tandem GnRH (2GnRH) coding sequence into the rabies virus G gene.

SEQ ID NO: 62 is the nucleotide sequence of dog ZP3, deposited under GenBank Accession No. NM_001003224 on Aug. 5, 2004.

SEQ ID NOs: 63 and 64 are the nucleotide and amino acid sequences, respectively, of rabies virus ERA G protein with one copy of GnRH inserted at the junction of the ectodomain and the transmembrane domain (following nucleotide 1374, amino acid 458) of glycoprotein. This construct is referred to as G-C-GnRH.

DETAILED DESCRIPTION

I. Introduction

Rabies is a major public health concern globally. In most instances, humans are infected with rabies virus through the bite of a rabid domestic or wild animal. In developing countries, dogs are responsible for approximately 94% of human deaths due to rabies. Stray or unvaccinated dogs are the primary reservoir for rabies in Latin American, Asian and African countries. Furthermore, in the United States, there are currently millions of stray or feral cats. Thus, there is a global need to both prevent rabies and control the population of rabies susceptible animals, particularly dogs.

Previous methods of animal population control have included the use of immunocontraceptive vaccines. Immunocontraception involves stimulating immune responses against gametes or reproductive hormones to prevent conception. Immunocontraception is a humane method for population control of pest and overabundant populations of mammalian wildlife (such as raccoons or deer). A number of studies have focused on the use of zona pellucida glycoprotein 3 (ZP3), which is the main receptor used by sperm for fertilization of an egg. However, administration of ZP3, or other immunocontraceptive protein, has previously required co-administration of an adjuvant and/or booster doses to elicit a sufficient immune response against the protein such that fertilization is inhibited. Thus, current methods of immunocontraception have significant limitations, particularly for wild animal populations.

The immunogenic compositions and methods disclosed herein provide a means of simultaneously protecting vaccinated animals against rabies and controlling animal populations by inhibiting fertility. Recombinant rabies viruses comprising at least one heterologous nucleic acid sequence encoding an immunocontraceptive protein are described herein. In particular examples, the immunocontraceptive protein is GnRH or ZP3. In some cases, the recombinant rabies viruses comprise both GnRH and ZP3. Alternatively, animals can be immunized with two different recombinant rabies viruses, one comprising GnRH, and a second comprising ZP3. Because the immunocontraceptive protein is encoded in the genome of the rabies virus, when recombinant rabies virus particles are produced, the immunocontraceptive peptides are incorporated into the virion (structural protein) or are contained within the virion (non-structural protein). By incorporating the immunocontraceptive protein into the rabies virus particle, an adjuvant is not required to elicit a sufficient immune response against both rabies virus and the immunocontraceptive protein.

II. Abbreviations

| | |
|---|---|
| CMV | Cytomegalovirus |
| CTVT | Canine transmissible venereal tumor |
| DFA | Direct fluorescent assay |
| DNA | Deoxyribonucleic acid |
| ERA | Evelyn-Rokitnicki-Abelseth |
| FFU | Focus-forming units |
| FITC | Fluorescein isothiocyanate |
| FSH | Follicle stimulating hormone |
| G | Rabies virus glycoprotein |
| G* | Glycoprotein with an Arg to Glu change at residue 333 |
| GnRH | Gonadotropin-releasing hormone |
| HPLC | High performance liquid chromatography |

-continued

| | |
|---|---|
| i.c. | Intracerebral |
| i.m. | Intramuscular |
| IRES | Internal ribosome entry site |
| KLH | Keyhole limpet hemocyanin |
| L | Rabies virus RNA-dependent RNA polymerase |
| LH | Luteinizing hormone |
| M | Rabies virus matrix protein |
| MALDI | Matrix-assisted laser desorption/ionization |
| $MICLD_{50}$ | Mouse intracerebral lethal dose 50 |
| N | Rabies virus nucleoprotein |
| NA | Neutralizing antibody |
| NLS | Nuclear localization signal |
| P | Rabies virus phosphoprotein |
| PAGE | Polyacrylamide gel electrophoresis |
| PVDF | Polyvinylidene diflouride |
| pZP | Porcine zona pellucida |
| RNA | Ribonucleic acid |
| RNP | Ribonucleoprotein |
| RV | Rabies virus |
| SDS | Sodium dodecyl sulfate |
| UV | Ultraviolet |
| VNA | Virus neutralizing antibody |
| ZP | Zona pellucida |

III. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular. In some embodiments described herein, an immunogenic composition is administered to an animal by an oral route.

Animal: Living multi-cellular vertebrate organisms, a category that includes, for example, mammals and birds. The term mammal includes both human and non-human mammals. The term "animal" includes both human and veterinary subjects, for example, humans, non-human primates, dogs, cats, horses, raccoons, bats, rats, mice, foxes, squirrels, opossum, coyotes, wolves and cows. As used herein, "subject" is interchangeable with "animal." As used herein a "domestic animal" refers to any animal that has been tamed by humans, often for use as work animals, a food source or as pets. Many domestic animals are selectively bred such that they differ from animals in the wild. As used herein, "wild animal" refers any animal living in a natural, undomesticated state.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods and compositions of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller ($K_d$) indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope.

In one example, antibody binding affinity is measured by end-point titration in an Ag-ELISA assay. Antibody binding affinity is substantially lowered (or measurably reduced) by the modification and/or substitution of one or more amino acids in the epitope recognized by the antibody paratope if the end-point titer of a specific antibody for the modified/substituted epitope differs by at least 4-fold, such as at least 10-fold, at least 100-fold or greater, as compared to the unaltered epitope.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Attenuated: In the context of a live virus, such as a rabies virus, the virus is attenuated if its ability to infect a cell or subject and/or its ability to produce disease is reduced (for example, eliminated). Typically, an attenuated virus retains at least some capacity to elicit an immune response following administration to an immunocompetent subject. In some cases, an attenuated virus is capable of eliciting a protective immune response without causing any signs or symptoms of infection.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Epitope: An antigenic determinant. These are particular chemical groups, such as contiguous or non-contiguous peptide sequences, on a molecule that are antigenic, that is, that elicit a specific immune response. An antibody binds a particular antigenic epitope based on the three dimensional structure of the antibody and the matching (or cognate) three dimensional structure of the epitope.

Fertility: Refers to the ability of an animal to produce offspring. As used herein "inhibiting fertility" refers to reducing the rate of, or preventing, reproduction.

Fixed: A fixed rabies virus is a strain of rabies virus that has undergone serial passage in a host to stabilize virulence of the virus. Fixed rabies viruses include, but are not limited to CVS, ERA, PV, SAD-B19 and HEP-Flury strains (Anilionis et al., *Nature* 294:275-278, 1981; Morimoto et al., *Viral.* 173:465-477, 1989).

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain to internal stop codons.

Gonadotropin-releasing hormone (GnRH): A peptide hormone responsible for the release of follicle stimulating hormone (FSH) and luteinizing hormone (LH) from the anterior pituitary. GnRH is synthesized and released by the hypothalamus and travels to the pituitary to mediate release of FSH and LH. The GnRH precursor protein is 92 amino acids and is processed to a decapeptide in mammals. GnRH is also known as GNRH1, luteinizing hormone releasing hormone (LHRH), progonadoliberin-1 and progonadoliberin-1 precursor. The term "GnRH" includes GnRH analogs and variants, including GnRH molecules containing substitutions, deletions, or insertions. The nucleotide and amino acid sequences of mammalian GnRH are set forth herein as SEQ ID NOs: 47 and 48, respectively.

Heterologous: As used herein, a "heterologous nucleic acid sequence" is a nucleic acid sequence that is derived from a different source or species. In some embodiments described herein, the heterologous nucleic acid sequence is a nucleic acid sequence encoding ZP3. In other embodiments, the heterologous nucleic acid sequence is a nucleic acid sequence encoding GnRH. In the context of a recombinant rabies virus, a heterologous nucleic acid sequence is any nucleic acid sequence that is not derived from the rabies virus.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between to distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are discussed by Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989, chapters 9 and 11; and Ausubel et al. *Short Protocols in Molecular Biology,* $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

"Specific hybridization" refers to the binding, duplexing, or hybridizing of a molecule only or substantially only to a particular nucleotide sequence when that sequence is present in a complex mixture (for example, total cellular DNA or RNA). Specific hybridization may also occur under conditions of varying stringency.

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

Immunize: To render a subject protected from a disease (for example, an infectious disease), such as by vaccination.

Immunocontraceptive protein: Refers to a protein or protein fragment (also referred to as an "antigen") capable of eliciting an immune response in a subject that results in inhibition or loss of fertility in the subject.

Immunogen: A compound, composition, or substance which is capable, under appropriate conditions, of stimulating an immune response, such as the production of antibodies or a T-cell response in an animal, including compositions that are injected or absorbed into an animal.

Immunogenic composition: A term used herein to mean a composition useful for stimulating or eliciting a specific immune response (or immunogenic response) in a vertebrate. The immunogenic composition includes a recombinant rabies virus, such as a recombinant rabies virus expressing a heterologous protein (such as ZP3 and/or GnRH). In some embodiments, the immunogenic response is protective or provides protective immunity, in that it enables the vertebrate animal to better resist infection with or disease progression from the organism against which the immunogenic composition is directed (e.g., rabies virus). When the immunogenic compositions comprise an immunocontraceptive peptide, the immunogenic response elicited prevents or decreases the risk of pregnancy in female animals.

Without wishing to be bound by a specific theory, it is believed that an immunogenic response induced by an immunogenic composition may arise from the generation of an antibody specific to one or more of the epitopes provided in the immunogenic composition. Alternatively, the response may comprise a T-helper or cytotoxic cell-based response to one or more of the epitopes provided in the immunogenic composition. All three of these responses may originate from naïve or memory cells. One specific example of a type of immunogenic composition is a vaccine.

In some embodiments, an "effective amount" or "immune-stimulatory amount" of an immunogenic composition is an amount which, when administered to a subject, is sufficient to engender a detectable immune response. Such a response may comprise, for instance, generation of an antibody specific to one or more of the epitopes provided in the immunogenic composition. Alternatively, the response may comprise a T-helper or CTL-based response to one or more of the epitopes provided in the immunogenic composition. All three of these responses may originate from naïve or memory cells. In other embodiments, a "protective effective amount" of an immunogenic composition is an amount which, when administered to an animal, is sufficient to confer protective immunity upon the animal.

Inhibiting or treating a disease: Inhibiting the full development of a disease or condition, for example, in a subject who is at risk for a disease. A specific example of diseases is rabies. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

Nucleic acid molecule: A polymeric form of nucleotides, which may include both sense and anti-sense strands of RNA, cDNA, genomic DNA, and synthetic forms and mixed polymers of the above. A nucleotide refers to a ribonucleotide, deoxynucleotide or a modified form of either type of nucleotide. The term "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A polynucleotide may include either or both naturally occurring and modified nucleotides linked together by naturally occurring and/or non-naturally occurring nucleotide linkages.

Open reading frame (ORF): A series of nucleotide triplets (codons) coding for amino acids without any internal termination codons. These sequences are usually translatable into a peptide/polypeptide/protein/polyprotein.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence is the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, proteins or antibodies that bind these proteins, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasmid: A circular nucleic acid molecule capable of autonomous replication in a host cell.

Polypeptide: A polymer in which the monomers are amino acid residues joined together through amide bonds. When the amino acids are alpha-amino acids, either the L-optical isomer or the D-optical isomer can be used, the L-isomers being preferred for many biological uses. The terms "polypeptide" or "protein" as used herein are intended to encompass any amino acid molecule and include modified amino acid molecules. The term "polypeptide" is specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |

-continued

| Original Residue | Conservative Substitutions |
|---|---|
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalalananine, pentafluorophenylalanine, phenylalanine, tryptophan and tyrosine. It is noted that some amino acids are classified in more than one group, for example, histidine, tryptophan, and tyrosine are classified as both polar and aromatic amino acids. Additional amino acids that are classified in each of the above groups are known to those of ordinary skill in the art.

Substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Probes and primers: A probe comprises an isolated nucleic acid molecule attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989 and Ausubel et al. *Short Protocols in Molecular Biology,* $4^{th}$ ed., John Wiley & Sons, Inc., 1999.

Primers are short nucleic acid molecules, for instance DNA oligonucleotides 6 nucleotides or more in length, for example that hybridize to contiguous complementary nucleotides or a sequence to be amplified. Longer DNA oligonucleotides may be about 10, 12, 15, 20, 25, 30, or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Methods for preparing and using nucleic acid probes and primers are described, for example, in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989; Ausubel et al. *Short Protocols in Molecular Biology,* $4^{th}$ ed., John Wiley & Sons, Inc., 1999; and Innis et al. PCR Protocols, *A Guide to Methods and Applications*, Academic Press, Inc., San Diego, Calif., 1990. Amplification primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

Protein: A biological molecule, particularly a polypeptide, expressed by a gene and comprised of amino acids.

Purified: The term "purified" does not require absolute purity; rather, it is intended as a relative term. Thus, for example, a purified protein preparation is one in which the subject protein is more pure than in its natural environment within a cell. Generally, a protein preparation is purified such that the protein represents at least 50% of the total protein content of the preparation.

Rabies virus (RV): A member of the Rhabdoviridae family having a non-segmented RNA genome with negative sense polarity. Rabies virus is the prototype of the *Lyssavirus* genus. The rabies virus Evelyn-Rokitnicki-Abelseth (ERA) strain is a strain derived from the Street-Alabama-Dufferin (SAD) strain, first isolated from a rabid dog in Alabama (USA) in 1935. The ERA strain was derived after multiple passages of SAD RV in mouse brains, baby hamster kidney (BHK) cells, and chicken embryos. The complete genomic sequence of the ERA strain is disclosed in PCT Publication No. WO 2007/047459, and the sequence of the ERA strain recovered by reverse genetics is set forth herein as SEQ ID NO: 1.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In some embodiments, recombinant rabies virus is generated using reverse genetics, such as the reverse genetics system described in PCT Publication No. WO 2007/047459. In some examples, the recombinant rabies viruses comprise one or more mutations in a viral virulence factors, such as glycoprotein. In other examples, the recombinant rabies viruses comprise a heterologous gene, such as a sequence encoding an immunocontraceptive peptide (for example, ZP3 or GnRH).

Reverse genetics: Refers to the process of introducing mutations (such as deletions, insertions or point mutations) into the genome of an organism or virus in order to determine the phenotypic effect of the mutation. For example, introduction of a mutation in a specific viral gene enables one to determine the function of the gene.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (*Gene,* 73:237-44, 1988); Higgins and Sharp (*CABIOS,* 5:151-53, 1989); Corpet et al. (*Nuc. Acids Res.,* 16:10881-90, 1988); Huang et al. (*Comp. Appls. Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.,* 215:403-10, 1990; Gish and States, *Nature Genet.,* 3:266-72, 1993; Madden et al., *Meth. Enzymol.,* 266:131-41, 1996; Altschul et al., *Nucleic Acids Res.,* 25:3389-402, 1997; and Zhang and Madden, *Genome Res.,* 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Therapeutically effective amount: A quantity of a specified agent sufficient to achieve a desired effect in a subject being treated with that agent. For example, this may be the amount of a recombinant rabies virus useful for eliciting an immune response in a subject and/or for preventing infection by rabies virus. Ideally, in the context of the present disclosure, a therapeutically effective amount of a recombinant rabies virus is an amount sufficient to increase resistance to, prevent, ameliorate, and/or treat infection caused by rabies virus in a subject without causing a substantial cytotoxic effect in the subject. The effective amount of a recombinant rabies virus useful for increasing resistance to, preventing, ameliorating, and/or treating infection in a subject will be dependent on, for example, the subject being treated, the manner of administration of the therapeutic composition and other factors. In some embodiments, the recombinant rabies viruses described herein comprise a nucleic acid sequence encoding an immunocontraceptive protein. For these compositions, a therapeutically effective amount may also refer to the amount of the recombinant rabies virus needed to inhibit fertility, such as preventing or reducing the rate of pregnancy in female animals.

Vector: A nucleic acid molecule as introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art.

Virus: Microscopic infectious organism that reproduces inside living cells. A virus typically consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

Zona pellucida 3 (ZP3): A glycoprotein expressed on the surface of an egg that serves as the primary receptor for sperm fertilization. ZP3 is also known as zona pellucida glycoprotein 3, zona pellucida protein C (ZPC), sperm receptor and zona pellucida sperm-binding protein 3. As used herein, ZP3 refers to a ZP3 from any animal species, including, but not limited to human, dog, pig, mouse or rat. Exemplary sequences of ZP3 are provided herein, including dog ZP3 (SEQ ID NO: 7 and SEQ ID NO: 62). The term "ZP3" includes ZP3 analogs and variants, including mutated or truncated ZP3.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

IV. Overview of Several Embodiments

It is disclosed herein that recombinant rabies viruses comprising a heterologous sequence encoding an immunocontraceptive peptide can be successfully recovered using a previously described reverse genetics system. In some examples, the immunocontraceptive peptide is GnRH or ZP3. Studies in non-human animals demonstrate that the recombinant rabies viruses described herein elicit high titers of neutralizing antibody specific for rabies virus, induce immunocontraceptive peptide-specific antibodies, protect animals against rabies virus challenge and produce no adverse side effects. It is believed they will provide contraceptive effects in animals to which they are administered.

Provided herein is a recombinant rabies virus, wherein the genome of the recombinant rabies virus comprises a heterologous nucleic acid sequence encoding an immunocontraceptive protein. In some embodiments, the immunocontraceptive protein is gonadotropin-releasing hormone (GnRH) or zona pellucida 3 (ZP3). In some embodiments, the genome of the recombinant rabies virus comprises a nucleic acid sequence encoding GnRH and a nucleic acid sequence encoding ZP3. Generally, the recombinant rabies viruses are generated using a reverse genetics system, such as the system disclosed in PCT Publication No. WO 2007/047459. However, any recombinant rabies viruses comprising a heterologous nucleic acid sequence encoding an immunocontraceptive peptide is contemplated.

In some embodiments, the genome of the recombinant rabies virus is derived from the rabies virus ERA strain. In particular examples, the ERA strain comprises the nucleotide sequence set forth as SEQ ID NO: 1. Although the ERA strain is exemplified herein, any suitable strain of rabies virus can be used. An appropriate rabies virus strain can be selected by one of skill in the art. Examples of rabies virus strains include, but are not limited to CVS, ERA, PV, SAD-B19 and HEP-Flury, SAG1, SAG2 and RC-HL.

Figure 5A:
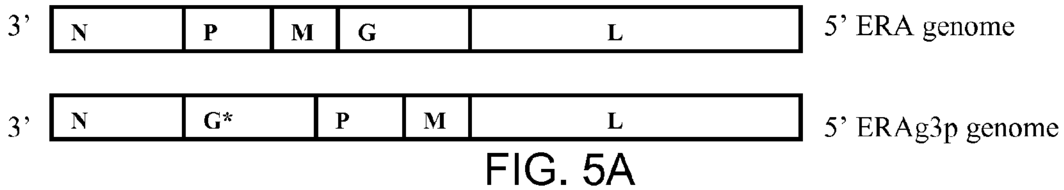
FIG. 5A is a schematic of the parental ERA and rearranged ERAg3p genomes. To generate ERAg3p, the G gene in the ERA genome was relocated ahead of the P gene, and was mutated at amino acid residue 333 from AGA (denoted as G) to GAG (denoted as G*).
Figure 5B:
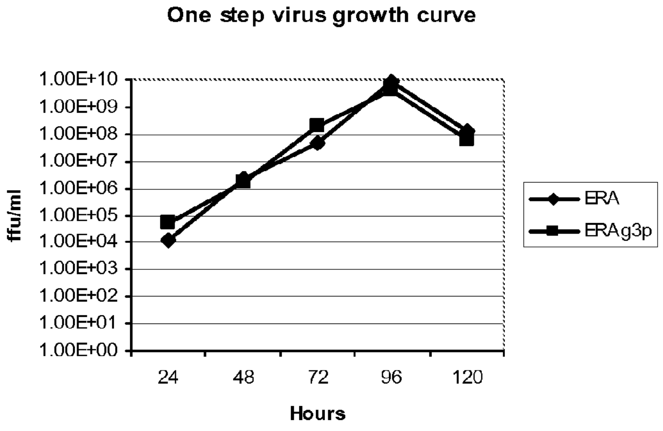
FIG. 5B is a one-step growth curve showing growth characteristics of the rearranged ERAg3p virus. The recovered virus ERAg3p grew as well as the parental ERA virus.
Figure 5C:
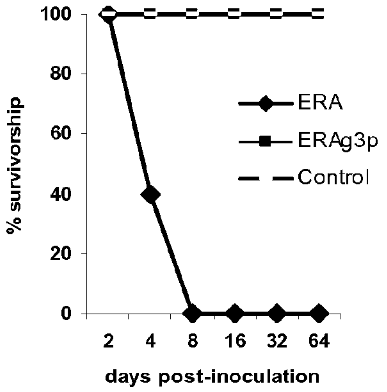
FIG. 5C is a line graph comparing virulence of ERA and ERAg3p. ERAg3p did not cause death in any 3-week old mice after intracerebral injection.

In some embodiments, the genome of the recombinant rabies virus is engineered such that the rabies virus gene sequences are rearranged. In some examples, the glycoprotein (G) gene is relocated between the N and P genes, such that the rabies virus genes are in the following order: 3'-N-G-P-M-L-S' (see FIG. 5A). This type of virus, when derived from the ERA strain, is referred to herein as ERAg3p. Although relocation of the G gene is exemplified herein, any other rearrangements of the rabies virus genes are contemplated, as long as recombinant virus can be recovered using reverse genetics.

In some embodiments, the rabies virus strain is an attenuated strain. In some examples, the glycoprotein of the recombinant rabies virus comprises a Glu at amino acid position 333 (corresponding to residue 352 of SEQ ID NO: 5). Other rabies virus attenuating mutations are known in the art and can be used with the compositions and methods provided herein.

The ZP3 nucleic acid sequence can be a ZP3 sequence from any animal species, such as human, pig, rat, mouse or dog. In some embodiments, the ZP3 nucleic acid sequence is a dog ZP3 nucleic acid sequence. In some examples, the dog ZP3 nucleic acid sequence is SEQ ID NO: 7. In some embodiments, the GnRH nucleic acid sequence is SEQ ID NO: 47. The ZP3 nucleic acid sequence incorporated into the recombinant rabies virus need not be 100% identical to a ZP3 nucleic acid sequence known in the art or disclosed herein. Similarly, the GnRH nucleic acid sequence incorporated into the recombinant rabies virus can be from any animal species, and need not be 100% identical to a GnRH nucleic acid sequence known in the art or disclosed herein. Rather, the ZP3 or GnRH nucleic acid sequence need only be capable of eliciting an immune response in the animal in which the recombinant rabies virus is administered. In some embodiments, the ZP3 nucleic acid sequence is at least 70%, at least 75%, at least 80%, at least 85%, at least 90%, at least 95%, at least 99% or 100% identical to SEQ ID NO: 7. In some embodiments, the GnRH nucleic acid sequence is at least 70%, at least 75%, at least 80%, at least 85%, at least 90%, at least 95%, at least 99% or 100% identical to SEQ ID NO: 47.

In some embodiments, the recombinant rabies viruses comprise a single copy of the ZP3 or GnRH nucleic acid sequence, or a single copy of each sequence. In other embodiments, the recombinant rabies viruses comprise multiple copies of the ZP3 or GnRH nucleic acid sequence (or another immunocontraceptive peptide), such as two, three, four, five, six, seven, eight or nine copies of one or both of the ZP3 and GnRH nucleic acid sequences. When multiple copies of the ZP3 and/or GnRH nucleic acid sequence are used, the copies can be inserted in the genome of the recombinant rabies virus such that the sequences are contiguous. Alternatively, the multiple copies of the ZP3 or GnRH nucleic acid sequences can be inserted at different positions within the rabies virus genome, such as in different genes, or at different sites within the same gene.

Figures 3A, 3B:
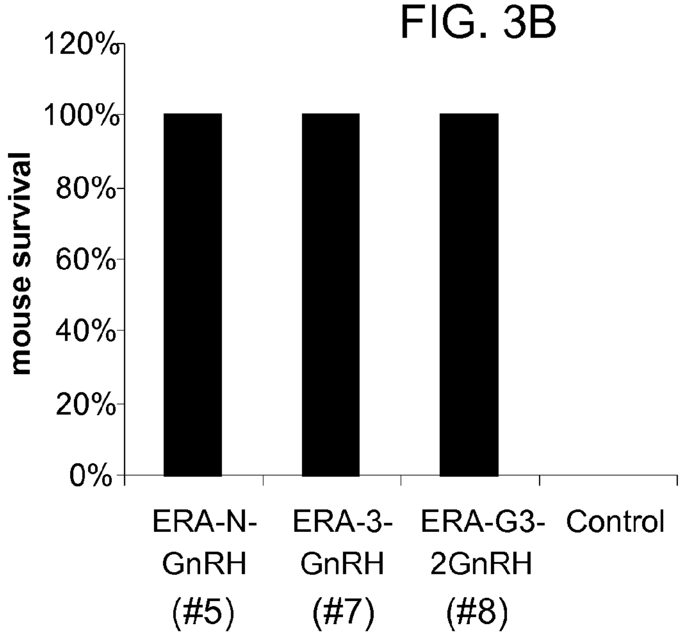
FIG. 3A is a table listing exemplary recombinant rabies viruses comprising dog ZP3 (DZP3), GnRH or both. The virus descriptions indicate the location of insertion of ZP3 and/or GnRH in the virus genome (G3=glycoprotein with the G333 mutation).
FIG. 3B is a graph showing survival of unvaccinated mice (control) or mice vaccinated with either ERA-N-GnRH (virus #5), ERA-3-GnRH (virus #7) or ERA-G3-2GnRH (virus #8). Each group of mice was subsequently challenged with a lethal dose of rabies virus.

In some embodiments, the heterologous sequence encoding the immunocontraceptive peptide is inserted within or adjacent to the rabies virus glycoprotein gene. In particular examples, the heterologous sequence is inserted following the signal sequence of glycoprotein. In other embodiments, the heterologous sequence is inserted at or near (such as immediately following) antigenic site IIa of glycoprotein. In other embodiments, the heterologous sequence is inserted between the ectodomain and transmembrane domain of glycoprotein. In particular examples, the heterologous nucleic acid sequence is inserted following the signal sequence (nucleotides 1-57 of SEQ ID NO: 49) of the glycoprotein gene. In some cases, when the GnRH sequence is inserted at this site, the glycoprotein gene comprises the nucleic acid sequence of SEQ ID NO: 49 (single copy of GnRH) or SEQ ID NO: 51 (two tandem copies of GnRH). In some examples, when the GnRH sequence is inserted at antigenic site IIa (nucleotide 663 of SEQ ID NO: 53) of the glycoprotein gene, the glycoprotein gene comprises the nucleic acid sequence of SEQ ID NO: 53. In some examples, when the GnRH sequence is inserted at the junction of the ectodomain and transmembrane domain of glycoprotein (following nucleotide 1374 of SEQ ID NO: 63), the glycoprotein gene comprises the nucleic acid sequence of SEQ ID NO: 63. In other specific examples, the ZP3 nucleic acid sequence is inserted between the rabies virus P and M genes. In some embodiments, the recombinant rabies virus is a rabies virus listed in FIG. 3A or Table 3.

Also provided herein are immunogenic compositions comprising one or more of the recombinant rabies viruses described herein. Further provided is an immunogenic composition comprising a first recombinant rabies virus and a second recombinant rabies virus, wherein the genome of the first recombinant rabies virus comprises a GnRH nucleic acid sequence and the genome of the second recombinant rabies virus comprises a ZP3 nucleic acid sequence. The first recombinant rabies varies can be any recombinant rabies virus comprising a nucleic acid sequence encoding GnRH, as described herein. The second recombinant rabies virus can be any recombinant rabies virus comprising a nucleic acid sequence encoding ZP3, as described herein. In some embodiments, the immunogenic compositions further comprise a pharmaceutically acceptable carrier. In some embodiments, the immunogenic compositions further comprise an adjuvant.

Also provided is a method of immunizing a non-human animal against rabies virus infection and inhibiting fertility of the animal, comprising administering to the animal a therapeutically effective amount of an immunogenic composition comprising one or more of the recombinant rabies viruses described herein. The composition can be administered using any suitable route. In some embodiments, the immunogenic composition is administered orally, such as through foodbaits. The animal can be any animal susceptible to rabies virus infection for which population control is desired. In some embodiments, the animal is a domestic animal. In other embodiments, the animal is a wild animal. In some embodiments, the animal is a dog, cat, rat, mouse, bat, fox, raccoon, squirrel, opossum, coyote or wolf.

Also provided herein is the use of a composition comprising one or more recombinant rabies viruses with a genome encoding one or more immunocontraceptive peptides in the manufacture of a medicament for immunizing a non-human animal against rabies virus infection and inhibiting fertility of the animal. Further provided are compositions comprising one or more recombinant rabies viruses with a genome encoding one or more immunocontraceptive peptides for use in a method of immunizing a non-human animal against rabies virus infection and inhibiting fertility of the animal.

V. Determinants of Rabies Virus Pathogenicity

The rabies virus (RV) is a rhabdovirus—a non-segmented RNA virus with negative sense polarity. Within the Rhabdoviridae family, rabies virus is the prototype of the *Lyssavirus* genus. RV is composed of two major structural components, a nucleocapsid or ribonucleoprotein (RNP), and an envelope in the form of a bilayer membrane surrounding the RNP core. The infectious component of all rhabdoviruses is the RNP core, which consists of the negative strand RNA genome encapsidated by nucleoprotein (N) in combination with RNA-dependent RNA-polymerase (L) and phosphoprotein (P). The membrane surrounding the RNP contains two proteins, the trans-membrane glycoprotein (G) and the matrix (M) protein, located at the inner site of the membrane. Thus, the viral genome codes for these five proteins: the three proteins in the RNP (N, L and P), the matrix protein (M), and the glycoprotein (G).

The molecular determinants of pathogenicity of various rabies virus strains have not been fully elucidated. RV pathogenicity was attributed to multigenic events (Yamada et al., *Microbiol. Immunol.* 50:25-32, 2006). For example, some positions in the RV genome if mutated, affect viral transcription or replication, reducing virulence. Mutations at serine residue 389 of the phosphorylation site in the N gene (Wu et al., *J. Virol.* 76:4153-4161, 2002) or GDN core sequence of the highly conserved C motif in the L gene (Schnell and Conzelmann, *Virol.* 214:522-530, 1995) dramatically reduced RV transcription and replication.

The G protein, also referred to as spike protein, is involved in cell attachment and membrane fusion of RV. The amino acid region at position 330 to 340 (referred to as antigenic site III) of the G protein has been identified as important for virulence of certain strains of RV. Several studies support the concept that the pathogenicity of fixed RV strains is determined by the presence of arginine or lysine at amino acid residue 333 of the glycoprotein (Dietzschold et al., *Proc. Natl. Acad. Sci. USA* 80: 70-74, 1983; Tuffereau et al., *Virol.* 172: 206-212, 1989).

This phenomenon seems to apply at least to fixed rabies viruses such as CVS, ERA, PV, SAD-B19 and HEP-Flury strains (Anilionis et al., *Nature* 294:275-278, 1981; Morimoto et al., *Virol.* 173:465-477, 1989). For example, rabies vaccine viruses possessing an amino acid differing from Arg at position 333 of the glycoprotein are described, for instance, in WO 00/32755 (describing RV mutants in which all three nucleotides in the G protein $Arg_{333}$ codon are altered compared to the parent virus, such that the Arg at position 333 is substituted with another amino acid); European Patent 350398 (describing an avirulent RV mutant SAG1 derived from the Bern SAD strain of RV, in which the Arg at position 333 of the glycoprotein has been substituted to Ser); and European patent application 583998 (describing an attenuated RV mutant, SAG2, in which the Arg at position 333 in the G protein has been substituted by Glu).

Other strains, such as the RC-HL strain, possess an arginine residue at position 333 of the G, but do not cause lethal infection in adult mice (Ito et al., *Microl. Immunol.* 38:479-482, 1994; Ito et al., *J. Virol.* 75:9121-9128, 2001). As such, the entire G may contribute to the virulence of RV, although the determinants or regions have not previously been identified.

The G gene encodes the only protein that induces viral neutralizing antibodies. At least three states of RV glycoprotein are known: the native state (N) being responsible for receptor binding; an active hydrophobic state (A) necessary in the initial step in membrane fusion process (Gaudin, *J. Cell Biol.* 150:601-612, 2000), and a fusion inactive conformation (I). Correct folding and maturation of the G protein play important roles for immune recognition. The three potential glycosylated positions in ERA G extracellular domain occur at $Asn^{37}$, $Asn^{247}$ and $Asn^{319}$ residues (Wojczyk et al., *Glycobiology.* 8: 121-130, 1998). Nonglycosylation of G not only affects conformation, but also inhibits presentation of the protein at the cell surface.

It has been previously demonstrated (see PCT Publication No. WO 2007/047459) that expression of G enhances the anti-RV immune response. In addition, introduction of an Arg to Glu mutation at amino acid position 333 of RV ERA glycoprotein results in an attenuated virus (referred to as ERAg3). This attenuated virus is capable of eliciting significant titers of neutralizing antibodies in animals and conferring protection against wild-type virus challenge. Furthermore, as described in PCT Publication No. WO 2007/047459, a recombinant RV comprising two copies of glycoprotein with the G333 mutation is particularly useful as a vaccine due to its ability to elicit high titers of neutralizing antibodies without morbidity or mortality. In some examples herein, a recombinant rabies virus comprising the G333 mutation in glycoprotein is used to engineer immunocontraceptive compositions comprising ZP3 and/or GnRH. However, one of ordinary skill in the art will recognize that any one of a number of recombinant rabies viruses can be used to incorporate heterologous sequences using the reverse genetics systems disclosed in PCT Publication No. WO 2007/047459, and as summarized below.

VI. Rabies Virus Reverse Genetics System

RNA cannot readily be manipulated directly by molecular biological methods. Traditional RNA virus vaccines are from naturally attenuated isolates, which are difficult to control and provide unpredictable results. Reverse genetics technology makes it possible to manipulate RNA viruses as DNA, which can be mutated, deleted or reconstructed according to deliberate designs. Every gene function can be studied carefully, independently, and in concert, which benefits vaccine development. Reverse genetics involves reverse transcription of the RNA viral genome into cDNA, and cloning into a vector, such as a plasmid. After transfection of host cells, the vector is transcribed into RNA, to be encapsidated by viral structural proteins, which can also be supplied by plasmids. The encapsidated RNA forms a ribonucleoprotein complex, which results in virions that can be recovered.

An efficient reverse genetics system based on the rabies virus ERA strain is described in PCT Publication No. WO 2007/047459. This rabies reverse genetics system is useful for a variety of purposes, including to attenuate ERA virus in a defined manner for vaccine development and to produce ERA virus vectors for expression of heterologous proteins, such as proteins for immunocontraception, including ZP3 and GnRH.

The reverse genetics system disclosed in PCT Publication No. WO 2007/047459 is based on a full length transcription plasmid plus a plurality of helper plasmids (e.g., five helper plasmids). The helper plasmids encode the N, P, L proteins, and optionally the G protein, as well as the T7 polymerase. Although the G protein is not necessary for virus rescue, it improves virus recovery efficiency or virus budding when included in transfection.

Transcription involves both cellular RNA-dependent RNA polymerase II, which is available in mammalian cells, and T7 RNA polymerase, which is supplied by pNLST7 plasmids. The dual polymerases result in virus recovery efficiency that is both high and stable.

In the transcription plasmid, hammerhead and hepatitis delta virus ribozymes flank a rabies virus (e.g., ERA strain) antigenomic cDNA, enabling the production of authentic 5' and 3' ends of antigenomic viral RNA by transcription. The first ten nucleotides of the hammerhead sequence are designed to be complementary to the first ten nucleotides of the antisense genomic sequence.

Two modified T7 RNA polymerase constructs support virus recovery more efficiently than the wild type T7 RNA polymerase applied previously. One T7 RNA polymerase has been mutated from the first ATG to AT. The second T7 RNA polymerase has an eight amino acid nuclear localization signal (NLS) derived from the SV40 virus large T antigen fused after the first ATG from the parental T7. Addition of the NLS results in the T7 RNA polymerase being present predominantly in the nucleus. Following transfection mechanism of the NLS modified plasmid, the DNA/transfection reagent complex binds to the surface of the cell. Through endocytosis, the complex is taken into the endosome/lysosome, and the DNA is released into the cytosol. In the absence of the NLS, the majority of the transfected plasmids are retained in the cytosol and only a small percentage of the released DNA reaches the nucleus, where it is transcribed into RNA. After protein synthesis, the NLST7 RNA polymerase is transported back to the cell nucleus, and the helper plasmids (with T7/CMV promoters) in the nucleus will be transcribed by both NLST7 and cellular polymerase II. Thus, more mRNAs of the helper plasmids and cRNA of the full-length pTMF or its derivatives are synthesized and result in high efficiency of virus recovery.

After the initial expression of NLST7 by CMV promoter, NLST7 polymerase binds to pT7 for transcription of NLST7 gene. Through modification of the transcripts in the nucleus, more NLST7 mRNA is synthesized, resulting in more expression of NLST7 polymerase. The pT7 of the NLST7 polymerase as well as of the full length antigenomic transcription unit is under the control of the NLST7 polymerase, which acts as an "autogene." After expression of T7 RNA polymerase in the nucleus, the transfected T7 constructs continue to transcribe full length RNA template for N protein encapsidation and/or L protein binding, enhancing virus recovery efficiency.

The T7 polymerase, and all other plasmids, except the N protein encoding plasmid pTN, are placed under control of both CMV and T7 transcriptional regulatory elements. The N protein encoding nucleic acid is under the control of a T7 promoter and is translated in cap-independent manner based on an IRES (internal ribosome entry site). Cellular RNA polymerase II alone can help the recovery of RV if all the plasmids were cloned under the control of the CMV promoter. In the ERA reverse genetics system disclosed in PCT Publication No. WO 2007/047459, only pTN is under the control of the T7 promoter and is translated in a cap-independent manner. All other constructs are under control of both CMV and the T7 transcriptional regulatory elements. Typically, in RV, N synthesis is abundant and the ratio among N, P and L is approximately 50:25:1. To mimic the wild type viral transcription and assembly in RV reverse genetics, N expression should be the highest. With the aid of NLST7 polymerase and IRES translation mode, N protein is expressed efficiently after plasmid transfection. This reduces competition for transcription with house keeping genes in host cells, because the T7 transcription initiation signal does not exist in mammalian cells, and results in increased efficiency of T7 transcription.

In addition, as described in PCT Publication No. WO 2007/047459, to enhance production of viral proteins, the helper plasmids can be constructed to incorporate a Kozak sequence that has been optimized for the translation efficiency for each protein encoding sequence. After five days post-transfection in the ERA reverse genetics system, the rescued viruses reliably and repeatably grew to $10^7$ FFU/ml without further amplification.

Recombinant rabies viruses with favorable properties for vaccination can be designed using, for example, the reverse genetics system disclosed in PCT Publication No. WO 2007/047459. Modified strains having mutated glycoproteins are particularly suited for use as immunogenic compositions. This RV reverse genetics system also enables a rabies virus vector system for foreign (heterologous) gene expression. An extra transcription unit was demonstrated to be functional in two different locations after incorporation into the ERA RV genome. Thus, the RV reverse genetics system provides a means for introducing heterologous proteins that serve as immunocontraceptives. In some examples, the heterologous protein is ZP3, GnRH, or both.

VII. Immunocontraception

Provided herein are recombinant rabies viruses comprising within their genome heterologous nucleic acid sequences encoding one or more immunocontraceptive proteins. An immunocontraceptive protein refers to any protein or protein fragment (also referred to as an "antigen") capable of eliciting an immune response in a subject that results in inhibition or loss of fertility in the subject to which the antigen is administered. The recombinant rabies viruses described herein are contemplated for vaccination of non-human animals.

Immunocontraception involves vaccination against sperm, eggs or reproductive hormones to prevent fertilization or the production of gametes (Cooper and Larsen, *Reproduction* 132:821-828, 2006). Immunogens previously tested as immunocontraceptives include sperm antigens, whole sperm, lactate dehydrogenase (LDH-C4; a sperm-specific protein), fertilization antigen-1 (FA-1; a sperm-specific antigen), sperm protein 56 (sp56), eppin (a testis/epididymis protein), oocyte antigens (such as zona pellucida), gonadotropin riboflavin carrier protein, prolactin, proliferin, gonadotropins and gonadotropin releasing hormones (Delves et al., *Trends Immunol.* 23:213-219, 2002; O'Hern et al., *Vaccine* 15(16): 1761-1766, 1997; Zhu and Naz, *Proc. Natl. Acad. Sci.* 94(9): 4704-4709, 1997; Hardy and Mobbs, *Mol. Reprod. Dev.* 52(2):216-224, 1999; Hardy et al., *Reproduction Supplement* 60:19-30, 2002; O'Rand et al., *Science* 306:1189-1190, 2004; Cooper and Larsen, *Reproduction* 132:821-828, 2006).

A number of immunocontraceptive studies have focused on the use of either zona pellucida (ZP) or GnRH. However, in every case, it was necessary to administer an adjuvant with the ZP or GnRH proteins in order to elicit a sufficient immune response to inhibit fertility of the treated animals. It is disclosed herein that recombinant rabies viruses comprising ZP and/or GnRH can be used as immunocontraceptive compositions. The super-antigen like features of the rabies virus particle allow for the use of recombinant rabies viruses comprising an immunocontraceptive protein in the absence of an adjuvant.

Gonadotropin-Release Hormone (GnRH)

GnRH (also known as luteinizing hormone releasing hormone, or LHRH) has long been recognized as playing a central role in the regulation of fertility in animals. The fully processed form of GnRH is a decapeptide which has the same amino acid sequence in all mammals (SEQ ID NO: 48). Closely related GnRH compounds have also been identified in other non-mammals, including fowl, and receptors for GnRH have been identified in reptiles and amphibians. In males and females, GnRH is released from the hypothalamus into the bloodstream and travels via the blood to the pituitary, where it induces the release of the gonadotropins, luteinizing hormone (LH) and follicle stimulating hormone (FSH). These two gonadotropins in turn act upon the gonads, inducing steroidogenesis and gametogenesis. In growing male animals, the gonadotropins stimulate the development of the testes and the synthesis of testicular steroids. In the growing female animal, the development of the ovaries is stimulated and therein follicle development, synthesis of ovarian steroids and ovulation. Steroids released from the gonads into the circulation also act upon various other tissues (U.S. Patent Publication No. 2006/0013821).

A variety of GnRH immunogenic analogs have also been described and are suitable for use with the compositions and methods provided herein. Immunogenic analogs of GnRH include compounds containing a substitution, deletion, or insertion of between one and five amino acid residues in the GnRH amino acid sequence, as well as dimers or polymers thereof, which compound retains the ability to induce or stimulate the production in an animal of antibodies specific for GnRH. The substitutions and insertions can be accomplished with natural or non-natural amino acids, and substitutions are preferably conservative substitutions made with amino acids which maintain substantially the same charge and hydrophobicity as the original amino acid. Immunogenic analogs of GnRH include those described in, for example, U.S. Pat. Nos. 5,484,592; 6,284,733; 4,608,251; 5,759,551; and 5,403,586, and PCT Publication No. WO 88/05308.

Zona Pellucida (ZP)

ZP is a non-cellular glycoprotein coat surrounding mammalian eggs which regulates sperm-egg interactions during fertilization. The structure of ZP makes it an ideal candidate for a contraceptive target, since altering its structure can prevent pregnancy (U.S. Patent Publication No. 2004/0202674).

ZP immunization has been effective in lowering fertilization rates of many mammals (Willis et al., *J. Equine Vet. Sci.* 14:364-370, 1994; Brown et al., *J. Reprod. Immunol.* 35:43-51, 1997; Brown et al., *J. Reprod. Immunol.* 35:53-64, 1997; U.S. Pat. No. 6,027,727). Two independent reports indicated that pig zona pellucida (pZP) is an effective immunocontraceptive in domestic cats, however multiple boosters are required (Ivanova et al., *Theriogenology* 43:969-981, 1995; Bradley et al., *J. Biotechnol.* 73:91-101, 1999).

Porcine zona pellucida has also been used in liposome-based immunocontraceptive vaccines for reducing fertility of certain mammals by 90-100% with a multi-year efficacy (PCT Publication NO. WO 93/25231). However, use of pZP in such a liposome-based vaccine as a single administration vaccine is ineffective in cats (Gorman et al., *Theriogenology* 58:135-149, 2002).

ZP3 sequences from a variety of different species are well known in the art, including dog ZP3 (Genbank Accession No. NM_001003224, deposited on Aug. 5, 2004); porcine ZP3 (Genbank Accession No. D45065, deposited on Jan. 24, 1995; Genbank Accession No. NM 213893, deposited on May 20, 2004); mouse ZP3 (Genbank Accession No. BC103585, deposited on Aug. 22, 2005; Genbank Accession No. BC099465, deposited on Jul. 21, 2005; Genbank Accession No. BC103584, deposited on Aug. 22, 2005); rat ZP3 (Genbank Accession No. BC127488, deposited on Dec. 22, 2006); and human ZP3 (Genbank Accession No. BC113949, deposited on Feb. 25, 2006; Genbank Accession No. X56777, deposited on Jun. 16, 1993; Genbank Accession No. M60504, deposited on Aug. 4, 1993; Genbank Accession No. A18567, deposited on Jul. 21, 1994). Each of the above-listed Genbank Accession numbers is herein incorporated by reference. In specific examples herein, the ZP3 sequence is a dog ZP3 sequence (SEQ ID NO: 7). However, any ZP3 sequence capable of eliciting an immune response in the animal to be vaccinated can be used with the compositions and methods provided herein.

VIII. Administration and Use of Rabies Virus Immunocontraceptive Compositions The recombinant rabies viruses provided herein comprise at least one heterologous nucleic acid sequence encoding an immunocontraceptive protein. Thus, immunocontraceptive compositions comprising such recombinant rabies viruses have a dual function: (i) to protect vaccinated animals against rabies virus infection and (ii) to control animal population growth by inhibiting fertility of the animals. Accordingly, the immunocontraceptive compositions provided herein are contemplated for use with non-human animals. In some cases, the recombinant rabies virus is administered to domestic animals. In other cases, the recombinant rabies virus is administered to wild animals. Non-human animals for which the rabies virus immunocontraceptive compositions will be useful may include, but is not limited to, dogs, cats, rats, mice, bats, foxes, raccoons, squirrels, opossum, coyotes or wolves. Particularly with wild animals, it is preferred to administer the immunogenic composition orally, such as through food-baits.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immunogenic compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes. In preferred embodiments, the immunogenic compositions are administered orally. In some examples, oral administration comprises administering the compositions in food-baits.

The volume of administration will vary depending on the route of administration. Those of ordinary skill in the art will know appropriate volumes for different routes of administration.

Administration can be accomplished by single or multiple doses. The dose administered to an animal in the context of the present disclosure should be sufficient to induce a beneficial therapeutic response over time, such as to prevent RV infection and prevent reproduction. The dose required will vary depending on, for example, the species of animal.

The amount of immunogenic composition in each dose is selected as an amount that induces an immunostimulatory or immunoprotective response without significant, adverse side effects. Such amount will vary depending upon which specific composition is employed and how it is administered. Initial doses may range from about 1 μg to about 1 mg, with some embodiments having a range of about 10 μg to about 800 μg, and still other embodiments a range of from about 25 μg to about 500 μg. Following an initial administration of the immunogenic composition, subjects may receive one or several booster administrations, adequately spaced. Booster administrations may range from about 1 μg to about 1 mg, with other embodiments having a range of about 10 μg to about 750 μg, and still others a range of about 50 μg to about 500 μg. Periodic boosters at intervals of 1-5 years, for instance three years, may be desirable to maintain the desired levels of protective immunity. In preferred embodiments, animals receive a single dose of an immunogenic composition.

The preparation of food-baits containing immunogenic compositions is also within the ordinary skill of those in the art. For example, the preparation of food-baits containing live RV vaccines is disclosed in Wandeler et al. (*Rev. Infect. Dis.* 10 (suppl. 4):649-653, 1988), Aubert et al. (pp. 219-243, in *Lyssaviruses* (Rupprecht et al., eds.), Springer-Verlag, New York, 1994), and Fu et al. (pp. 607-617, in New Generation Vaccines ($2^{nd}$ Edit.) (Levine et al., eds.), Marcel Dekker, Inc., New York, 1997).

Provided herein are pharmaceutical compositions (also referred to as immunogenic or immunostimulatory compositions) which include a therapeutically effective amount of a recombinant RV alone or in combination with a pharmaceutically acceptable carrier. In some embodiments, the recombinant RV comprises a heterologous protein, such as ZP3 and/or GnRH.

Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The recombinant RVs described herein can be administered alone or in combination with other therapeutic agents to enhance antigenicity. For example, the recombinant viruses can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

The following examples are provided to illustrate certain particular features and/or embodiments. These examples should not be construed to limit the disclosure to the particular features or embodiments described.

EXAMPLES

Example 1

Rabies Virus ERA-Based Immunocontraceptive Studies Using Dog ZP3

This example describes the development of an immunocontraceptive composition comprising a recombinant rabies virus ERA strain and dog zona pellucida 3 (ZP3). Immunocontraceptive studies based on porcine zona pellucida (pZP) glycoprotein have been attempted in different animals, including dogs. The pZP complex was reported to be effective in a number of species as an immunocontraceptive. However, because the pZP complex is a mixture of whole porcine ovary, adverse reactions are not uncommon. Therefore, a canine ZP3 glycoprotein was expressed in *E. coli* and a dog ZP3 gene was cloned as a DNA vaccine candidate. The rationale was to develop a rabies virus ERA-based immunocontraceptive vaccine that can control rabies virus and dog population simultaneously. Rabies virus ERA has proved to be an ideal vector for expression of heterologous genes. Furthermore, it has been demonstrated that modified ERA virus is effective as an oral vaccine candidate in various animal species (see PCT Publication No. WO 2007/047459).

Full length dog ZP3 was synthesized chemically and assembled by polymerase chain reaction (PCR). Dog ZP3 is 1278 base pairs in length and encodes a protein of 426 amino acids. The synthesized gene is set forth herein as SEQ ID NO: 7; the amino acid sequence is set forth as SEQ ID NO: 8. To synthesize the dog ZP3 gene, the full length dog ZP3 gene was divided into two fragments for synthesis, which are referred to as the A and B fragments. Fragment A (619 base pairs), which starts from the ATG start codon and ends with the unique NdeI recognition site, was assembled with 18 oligonucleotides (Table 1). Fragment B (670 base pairs) starts from unique NdeI recognition site and continues to the stop codon (TAA) and was assembled by 20 oligonucleotides (Table 1). The method for designing the oligonucleotides was based on "inside-out gene synthesis" using the DNAWorks program (Hoover and Lubkowski, *Nucleic Acids Res.* 30(10): e43, 2002).

After the A and B fragments were successfully synthesized, they were sequenced carefully to correct any potential mutations introduced during the PCR reactions. One silent mutation (which does not change the amino acids sequence) from C to T was purposely maintained to distinguish the synthesized gene from the template gene (Genbank Accession Number NM_001003224, deposited on Aug. 5, 2004, SEQ ID NO: 62). The oligonucleotides for synthesis of the A and B fragments are shown in Table 1.

TABLE 1

Oligonucleotides for synthesis of dog ZP3

| OLIGO | SEQUENCE | SEQ ID NO: |
|---|---|---|
| 1A | AAAACTGCAGCCACCATG | 9 |
| 2A | AACTGCAGCCACCATGGGGCTGAGCTATGGA ATTTTCATCTGTTTTCTGCTCCT | 10 |
| 3A | TTTCATCTGTTTTCTGCTCCTGGGAGGCATGG AGCTGTGCTGCCCCCAGACCAT | 11 |
| 4A | CTGCCCCCAGACCATCTGGCCAACTGAGACC TACTACCCATTGACATCTAGGCC | 12 |
| 5A | CCCATTGACATCTAGGCCCCCAGTAATGGTG GACTGTCTGGAGTCCCAGCTGGT | 13 |
| 6A | GGAGTCCCAGCTGGTGGTCACTGTCAGCAAA GACCTTTTTGGTACTGGGAAGCT | 14 |
| 7A | CTTTTTGGTTACGGGAAGCTCATCAGGCCAG CAGACCTCACCCTGGGTCCAGAG | 15 |
| 8A | CACCCTGGGTCCAGAGAACTGTGAGCCCCTG GTCTCCATGGACACGGATGATGT | 16 |
| 9A | CATGGACACGGATGATGTGGTCAGGTTTGAG GTTGGGCTGCACGAGTGTGGCAG | 17 |
| 10A | GTGCTGTACACCAGAGCATTGTCAGTCACCT GCACCCTGCTGCCACACTCGTGC | 18 |
| 11A | CAGGTTGCCCGCAGGGCGGGGGCTGTGGATC AGGAAGGTGCTGTACACCAGAGC | 19 |
| 12A | ACTCGATGGGGACCTCGGCACGATTAGTTCT CAGGATGGACAGGTTGCCCGCAG | 20 |
| 13A | GGCCTGGCTGCTCACATTGCTGTGCCTGGGG TAGTGGCACTCGATGGGGACCTC | 21 |
| 14A | AGAGCATTGTGGTCCTGAAGGGCACCCAAGT GGGCAGGATGGCCTGGCTGCTCA | 22 |
| 15A | CCATTAGGCGGAGAGAGAAAACTAGCTTCTC CTCGAAGAGCATTGTGGTCCTGA | 23 |
| 16A | ATGTGGGGGATTGCTTCTCGGAGCCCCAGTC CTCCTCCATTAGGCGGAGAGAGA | 24 |
| 17A | CTTCAGCCTGGAGGTGGGCTATGTCTCCCAG CTGGAATGTGGGGGATTGCTTCT | 25 |
| 18A | ACAAAAAGTCGCAGTGGCATATGGCTGCCAG TGTGGACTTCAGCCTGGAGGTG | 26 |
| 1B | TGGCAGCCATATGCCACTGCGACTTTTTGTG GACCACTGT | 27 |
| 2B | GACTTTTTGTGGACCACTGTGTGGCCACGCT GACACCAGATCGGAATGCCTTCC | 28 |
| 3B | CAGATCGGAATGCCTTCCCTCATCACAAAAT TGTGGACTTCCATGGCTGTCTTG | 29 |

TABLE 1-continued

Oligonucleotides for synthesis of dog ZP3

| OLIGO | SEQUENCE | SEQ ID NO: |
|---|---|---|
| 4B | GACTTCCATGGCTGTCTTGTGGATGGTCTCTA CAATTCCTCTTCAGCCTTCAAA | 30 |
| 5B | AATTCCTCTTCAGCCTTCAAAGCCCCCAGAC CCAGGCCAGAGACTCTTCAGTTC | 31 |
| 6B | GCCAGAGACTCTTCAGTTCACAGTGGATGTT TTCCACTTTGCTAAGGACTCAAG | 32 |
| 7B | CCACTTTGCTAAGGACTCAAGAAACACGATC TATATCACCTGCCATCTGAAGGT | 33 |
| 8B | ACCTGCCATCTGAAGGTCACTCCGGCTGACC GAGTCCCAGACCAGCTAAACAAA | 34 |
| 9B | CCCAGACCAGCTAAACAAAGCTTGTTCCTTC ATCAAGTCTACCAAGAGGTCCTA | 35 |
| 10B | CAAGTCTACCAAGAGGTCCTACCCTGTAGAA GGCTCGGCTGATATTTGTCGCTG | 36 |
| 11B | ACCGGCCTGGAAGGCCACAGCTGCCTTTGTT ACAACAGCGACAAATATCAGCCG | 37 |
| 12B | GACCTGCGCCACCCTCTCTCTAGGTGGGACA GCCTCCTGGACCGGCCTGGAAGG | 38 |
| 13B | TTCTTCAGTCACGTGCCTGCGATTTCTAGTGT GGGAAACAGACCTGCGCCACCC | 39 |
| 14B | TTCCCAGGAAGATCAGAGGCCCCACGGTGAT CTCTGCTTCTTCAGTCACGTGCC | 40 |
| 15B | AGAGGTTGACCCCTCTATACCATGATCACTA GCCTTTCCCAGGAAGATCAGAGG | 41 |
| 16B | CCAGGCCTAAGCCCAACATCACAGAGGTGTG AGGAGAGGTTGACCCCTCTATAC | 42 |
| 17B | CCAGGACAATGGTAGCTAGAGTCAGGGATAC CACCGTGGCCAGGCCTAAGCCCA | 43 |
| 18B | GGGTGGGAAGCAGTACGATGCCTCTTGGCAA GGACCAGGACAATGGTAGCTAGA | 44 |
| 19B | CGGTACCTTATTGGGAGACAGATGCAGGGCA TATCACAGGGTGGGAAGCAGTAC | 45 |
| 20B | GACGGCGGTACCTTATTGGGAGAC | 46 |

After synthesis of the dog ZP3 gene, it was cloned into the pTMF construct (ERA full genomic cDNA construct, see PCT Publication No. WO 2007/047459) at the P-M intergenic region for virus recovery. Four recombinant ERA-dogZP3 viruses (ERAZP3, ERAg3ZP3, ERA2g3ZP3 and ERAZP3T; see FIG. 1) were recovered by an established reverse genetics system for vaccine studies (PCT Publication No. WO 2007/047459). ERAZP3 contains the ZP3 sequence and a wild-type ERA G protein coding sequence. ERAg3ZP3 and ERA2g3 contain the ZP3 sequence and one or two copies (respectively) of the G333 mutant glycoprotein coding sequence. ERAZP3T contains a truncated ZP3 and the wild-type ERA G protein coding sequence. Truncated ZP3 comprises a deletion of nucleotides 79 to 1044 of ZP3 (SEQ ID NO: 7).

The four recombinant ERA-dogZP3 virus strains grew like wild type ERA virus in both baby hamster kidney (BHK) and BSR cells (a clone of BHK-21 cells), except for ERA2g3ZP3, which grew slower in the first three rounds of infection, relative to wild type ERA virus. Primary neutralization test from infected mice showed that ERAZP3T produced neutralizing antibody (NA) titer as high as 714.

In order to express the dog ZP3 gene in both prokaryotic and eukaryotic systems for immunologic studies, dog ZP3 was cloned into the pEF vector (for mammalian cell expression; Invitrogen) and pET28 vector (for prokaryotic expression; Novagen). Primary data by indirect fluorescence assay (IFA) showed that dog ZP3 was expressed well in BSR cells, demonstrated by His-tag monoclonal antibody staining.

The results of in vitro and in vivo studies using rabies virus ERA-based dog ZP3 recombinant virus are summarized as follows. ERAZP3 virus grew to $10^9$ focus forming units (FFU)/ml in bioreactors, and replicated as well as parental ERA. Dog ZP3 was expressed as a non-structural protein in the purified ERAZP3 virion. ERAZP3 rabies virus, grown to $10^9$ FFU/ml in BSR cells, was purified by gradient ultra-centrifugation. The purified recombinant virus was analyzed by SDS-PAGE. Five viral structural protein bands were clearly shown. The ZP3 protein was expressed as a nonstructural protein in recombinant ERAZP3 rabies virus. To detect ZP3 antibodies in ERAZP3 virus-immunized mice, Western blots using pcDNA/ZP3 expression protein were performed. BSR cells were transfected with pcDNA/ZP3 plasmids. After 48 hours, the transfected BSR cells were harvested and lysed. The supernatants were analyzed by SDS-PAGE, followed by protein transfer to nitrocellulose membranes. A standard Western-blot protocol was applied for analysis. The specific protein band with a molecular weight of 50 kD was detected, which corresponds to the size of ZP3.

In a mouse model, ERAZP3 induced a strong immune response against rabies virus when administrated either intramuscularly or orally. The immunized mice were protected against virus challenge, while the controls succumbed. Dog ZP3 antibodies were detected by indirect fluorescent staining Approximately 60 mice were injected intramuscularly with 50 μl of the recombinant virus ($5\times10^6$ FFU per mouse). The mice were boosted at intervals of 7, 14 and 28 days. Rabies virus antibody response was evaluated. Rabies virus neutralization antibodies were very high, reaching more than 5 IU. The mice were euthanized and sera were collected for IFA and Western blot against ZP3 proteins. Positive results were observed in both tests.

In a hamster model, ERAZP3 administered intramuscularly induced a strong immune response against rabies virus. The immunized hamsters were protected when challenged. Dog ZP3 antibodies were detected by IFA. No adverse effects were observed in either mouse or hamster models.

Example 2

Rabies Virus ERA-Based Immunocontraceptive Pilot Studies Using GnRH

This example describes the development and testing of recombinant rabies viruses containing the gonadotropin-releasing hormone (GnRH) sequence inserted at various positions relative to the rabies virus glycoprotein (G).

GnRH has been proven to be efficient as an immunocontraceptive peptide for dogs. However, previously it has been necessary to link GnRH with a carrier protein (or adjuvant) to be immunogenic. The scale-up of the products to meet massive vaccination and quality control makes the synthetic chemical method unacceptable for commercial applications.

Through peptide analysis in vitro, appropriate positions for incorporation of GnRH into the glycoprotein can be applied for recombinant vaccine studies. There is no need for adjuvant because of the super-antigen-like properties of rabies virus particles. Since rabies virus grows efficiently in cell culture, scale-up of production is not limiting. Therefore, rabies virus engineered to include GnRH is an ideal candidate for simultaneous control of rabies and dog populations.

The GnRH peptide was tested in vitro to be immunogenic against rabbit anti-GnRH serum. Multiple locations in the rabies virus glycoprotein were chosen for insertion of the GnRH sequence (SEQ ID NO: 47) (see FIG. 2). The N terminus, antigenic site IIa, and the junction between the ectodomain and cytoplasmic domains were identified as ideal insertion sites for virus recovery. All recombinant viruses were recovered through an established reverse genetics system (PCT Publication No. WO 2007/047459). Rescued viruses were named ERA-N-GnRH, ERA-IIa-GnRH, and ERA-C-GnRH, according to the GnRH insertion site. These three viruses replicated as well as the parental wild type ERA, reaching titers of $10^9$ FFU/ml in cell culture, with the exception of the ERA-IIa-GnRH virus. The inserted GnRH was stable in the glycoprotein gene after virus passage. Preliminary experiments in dogs using intramuscular administration demonstrated sufficient immune responses against rabies with no detectable adverse effects.

To increase the immunogenicity of the GnRH peptide, two copies of the GnRH gene aligned in tandem were cloned to the N (ERA-N-2GnRH) and IIa (ERA-GnRH-p3) sites. In the ERA-N-GnRH virus, the GnRH sequence (SEQ ID NO: 47) was inserted immediately after the 19 amino acid signal sequence of the rabies virus glycoprotein. The nucleotide and amino acid sequence of ERA-N-GnRH are set forth as SEQ ID NOs: 49 and 50, respectively. To create ERA-N-2GnRH, two copies of the GnRH in tandem were inserted immediately after the 19 amino acid signal sequence of the rabies virus glycoprotein (SEQ ID NOs: 51 and 52). To generate ERA-GnRH-p3, the GnRH sequence was inserted after amino acid residue 221 (IIa antigenic site) in rabies virus glycoprotein (SEQ ID NOs: 53 and 54). All three viruses were successfully recovered by reverse genetics, and the GnRH gene was stably expressed in all the constructs by Northern-blot. In addition, all of the constructs grew as well as parental rabies virus, with the exception of ERA-GnRH-p3, with grew slower. The ERA-N-GnRH virus was tested in dogs after intramuscular injection with no adverse effects. These results demonstrate that the N-terminus, just after the signal sequence in rabies virus glycoprotein, is an ideal location for insertion of GnRH.

To determine whether recombinant rabies viruses comprising GnRH are capable of eliciting protective immunity against rabies virus infection, wild-type rabies virus challenge studies were performed. Mice were injected i.m. with $5\times10^5$ FFU of either ERA-N-GnRH, ERA-3-GnRH(N-G3-GnRH-P-M-L) or ERA-G3-2GnRH(N-G3/2GnRH-P-M-L) and subsequently challenged with a lethal dose of rabies virus (FIG. 3). All vaccinated animals survived rabies virus challenge. In contrast, none of the control mice (unvaccinated naïve mice) survived rabies virus challenge. These results demonstrate that recombinant rabies virus-based immunocontraceptive vaccines are effective at eliciting a protective rabies virus immune response in animals.

Example 3

Combined Vaccines for Rabies Virus and Immunocontraception

This example describes the construction and characterization of recombinant ERA rabies viruses encoding GnRH.

Materials and Methods

Synthesis and Conjugation of GnRH Peptide to Keyhole Limpet Hemocyanin (KLH)

The decapeptide of GnRH (peptide 1780, GnRH; SEQ ID NO: 55), and two copies of the GnRH in tandem (peptide 1781, 2GnRH; SEQ ID NO: 56) were synthesized chemically, and purified by high performance liquid chromatography (HPLC). After verification, peptides 1780 and 1781 were conjugated to KLH. KLH was purchased from Sigma-Aldrich (St. Louis, Mo.) and conjugation efficiency was analyzed through SDS-PAGE. Protein Marker SeeBlue™ and Marker 12 were purchased from Invitrogen (Carlsbad, Calif.). The Precision Plus protein ladder was obtained from Bio-Rad (Hercules, Calif.). The proteins were separated on 4-12% SDS-PAGE gels.

Relocation of the G Gene Ahead of the P Gene in the RV ERA Genome and Pathogenicity of the Rearranged Virus The rearranged RV ERA genome with the G gene relocated ahead of the P gene was constructed similarly to the previously described reverse genetics method (Wu and Rupprecht, *Virus Res.* 131: 95-99, 2008; Wu et al., Virus Res. 129: 91-103, 2007). The amino acid residue at position 333 (corresponding to residue 352 of SEQ ID NO: 5) of the RV G was changed from arginine (AGA) to glutamic acid (GAG) through mutagenesis (Wu et al., *J. Virol.* 76: 4153-61, 2002). The engineered virus was named ERAg3p. The growth characteristics of the mutated virus were determined in cell culture. BSR cells (a clone of BHK cell line) were grown in Dulbecco's minimal essential medium supplemented with 10% fetal bovine serum (Atlanta Biologicals, Lawrenceville, Ga.). RV ERAg3p-infected BSR cells were incubated at 34° C., in a 5% $CO_2$ incubator. The CELLine-1000 Bioreactor was from INTEGRA Bioscience AG (Switzerland). The stability of mutation at the defined position and the rearranged RV genome were verified through reverse transcription (RT)-polymerase chain reaction (PCR) by more than 100 continuous passages of infection in BSR cells. RV ERA or ERAg3p was injected intracerebrally (i.c) into ten three-week old ICR female mice (Charles River Laboratory). Ten healthy mice of the same species and age served as uninfected controls with injection of PBS buffer (0.01M, pH 7.4) by the same route. The virulence of RV ERAg3p was compared in parallel with that of parental ERA species. Animals were checked and recorded daily for signs of illness. Sick animals were euthanized by $CO_2$ intoxication, followed by cervical dislocation. The mouse brain was removed for RV diagnosis.

Insertion of the Coding Sequence of GnRH into Various Locations of the G Gene in RV ERAg3p Virus The coding sequence of GnRH (or 2GnRH) was inserted into 6 different locations of the G gene in RV ERAg3p. The G gene with the defined mutation in RV ERAg3p was denoted as G*. The primer sequences used for insertion of the GnRH or 2GnRH into the G* are shown in Table 2. Mutagenesis was performed as described previously (Wu and Rupprecht, *Virus Res.* 131: 95-99, 2008). The final 12 G* gene constructs were verified by sequencing using the ABI 3730 DNA Analyzer.

TABLE 2

Primers for insertion of GnRH or 2GnRH into G*

| Insert | Primer | Sequence | SEQ ID NO: |
|---|---|---|---|
| GnRH | GNRH15 (Forward) | CCAACCTGTCAGGGTTCTCCGAACA CTGGAGCTACGGTTTGAGACCCGGG TACATGGAACTTAAAGTTG | 58 |
| GnRH | GNRH13 (Reverse) | GGAGAACCCTGACAGGTTGGTGCAT CCTTCGTCCTCCAC | 59 |

TABLE 2-continued

Primers for insertion of GnRH or 2GnRH into G*

| Insert | Primer | Sequence | SEQ ID NO: |
|---|---|---|---|
| 2GnRH | 2GNRHN5 (Forward) | GGTTTTTCCATTGTGTTTTGGGGAAC ACTGGAGCTACGGTTTGAGACCCGG GGAACACTGGAGCTACGGTTTGAGA CCCGGGAAATTCCCTATTTACACG | 60 |
| 2GnRH | 2GNRHN3 (Reverse) | CCCAAAACACAATGGAAAAACCAG AAGGGGTACAAACAGG | 61 |

Recovery and Characterization of the GnRH-Carrying ERAg3p Viruses

The 12 constructs with GnRH (or 2GnRH) in-frame fused to the G* gene were applied for virus recovery following a previous reported protocol (Wu and Rupprecht, *Virus Res.* 131: 95-99, 2008; Wu et al., *Virus Res.* 129: 91-103, 2007). If virus could not be rescued in the first round transfection, two additional trials were repeated. A negative result by direct fluorescent assay (DFA) was interpreted as an indication of a non-optimal site in the G gene for GnRH insertion. The rescued viruses were further grown in the BSR cells to high titers using bioreactor incubation for characterization.

Expression of GnRH in RV ERAg3p Viruses

Total RNA from the GnRH-carrying ERAg3p virus-infected BSR cells was extracted using TRIZOL™ Reagent (Invitrogen, Carlsbad, Calif.). Digoxigenin (Dig)-labeled antisense oligonucleotide GnRH probe was synthesized according to standard methods. The Dig nucleic acid detection kit was purchased from Roche (Roche Diagnostics GmbH, Roche Applied Science, Penzberg, Germany). The protocol for Northern blotting has been previously described (Wu and Rupprecht, *Virus Res.* 131: 95-99, 2008; Wu et al., *Virus Res.* 129: 91-103, 2007; Wu et al., *J. Virol.* 76: 4153-61, 2002). The RNA molecular weight marker 1 was obtained from Roche (Roche, Indianapolis, Ind.). The procedure for purification of RV from infected cell culture supernatants was modified from previous descriptions (Thomas et al., *Virology* 25: 271-275, 1965; Sokol et al., *J. Virol.* 2: 836-849, 1968). Briefly, about 200 ml of virus supernatant from cell culture was filtered (0.22 μm pore diameter) to remove possible cell debris. The virions were pelleted through ultra centrifugation at 22,500×g for 1 hour (Beckman, SW 28). The pellet was resuspended overnight at 4° C. in 2 ml of 0.5 mM Tris buffer (pH 7.2), and was loaded to sucrose gradients for centrifugation at 24,000×g for 1 hour (Beckman, SW 41). The virus band in the gradient was collected for SDS-PAGE analysis. The pre-stained protein molecular weight standard was purchased from GIBCO (Carlsbad, Calif.).

Safety and Potency Against Rabies Using the GnRH-Carrying RV ERAg3p Viruses in a Mouse Model Three-week old ICR female mice (Charles River Laboratory) were divided into four groups of 10 animals each. Group 1 was inoculated with RV ERA-N-2GnRH, group 2 with ERA-N-GnRH, group 3 with ERA-IIa-GnRH, and group 4 (as control) with PBS buffer (0.01 M, pH 7.4). Per mouse, 50 μl of each virus ($6.0 \times 10^6$ FFU) or PBS buffer (0.01 M, pH 7.4, the controls) was injected intramuscularly (i.m) in the gestrocnemius muscle in the left leg. Three weeks after inoculation, surviving animals were challenged i.m by the same route in the right leg with a lethal dose of 50 μl of about 2.5-10.0 $MICLD_{50}$ dog/coyote street RV (MD5951). The safety and potency of the viruses for the animals was analyzed two months after challenge.

Reaction of Serum from Immunized Mouse Using the GnRH-Carrying RV ERAg3p Viruses Against GnRH-KLH and 2GnRH-KLH Conjugates Ten 3-week old ICR female mice (Charles River Laboratory) were immunized i.m in the gestrocnemius muscle of the left leg with 50 μl ($6.0 \times 10^6$ FFU) of ERA-N-2GnRH, ERA-N-GnRH or ERA-IIa-GnRH. Three weeks post-vaccination, serum was collected by the retro orbital route after sedation of the animals. Serum was maintained at −20° C. for further analysis. The GnRH-KLH and 2GnRH-KLH conjugates were separated on 4-12% SDS-PAGE gels, and were transferred to polyvinylidene diflouride (PVDF) membrane (Sigma-Aldrich, St. Louis, Mo.) for Western blotting against the immunized mouse serum. Briefly, after gel electrophoresis, GnRH-KLH and 2GnRH-KLH were transferred to the PVDF membrane for blocking in 1× casein buffer (Vector Laboratories Inc, Burlingame, Calif.) at room temperature for 30 minutes. The immunized mouse serum (1:200 dilution in 1× casein reagent) was incubated with the membrane at room temperature for 30 minutes. After three washes (3 minutes each) in 1× casein Tris buffer, biotinylated anti-mouse IgG (H+L) (Vector Laboratories Inc, Burlingame, Calif.) at 1:1000 was added for another incubation of 30 minutes at room temperature. The staining kit was the ABC system from Vector Laboratories Inc. (Burlingame, Calif.).

Reaction of GonaCon™ Immunized Rabbit Serum Against the GnRH-Carrying RV ERAg3p Viruses GonaCon™ immunized rabbit serum was obtained from the National Wildlife Research Center, USDA. The indirect fluorescent assay (IFA) for detection of GnRH peptide in recombinant RV-ERAg3p viruses was performed as follows. In one six-well-plate (Becton Dickinson Labware, N.J.), the ERA-N-2GnRH, ERA-N-GnRH or ERA-IIa-GnRH virus-infected BSR cells (37° C. for 48 h) were fixed in 4% formalin PBS (Protocol Formalin®, Fisher Scientific Company LLC, Kalamazoo, Inc) at room temperature for 30 minutes. The GonaCon™ immunized rabbit serum at a dilution of 1:200 in PBS (0.01 M, pH 7.4) was added to the fixed BSR cells, and incubated at 37° C. for 30 minutes. After three washes in the same PBS (3 minutes each), the FITC-conjugated goat anti-rabbit IgG (H+L) at 1:200 dilution (Vector Laboratories Inc, Burlingame, Calif.) was added, and incubated at 37° C. for 30 minutes. The staining results were recorded under UV microscopy. For Western blot using the GonaCon™ immunized rabbit serum against purified GnRH-carrying RV ERA viruses, the same protocol described above was followed.

Results

Synthesis and Conjugation of GnRH Peptide to KLH

Figure 4:
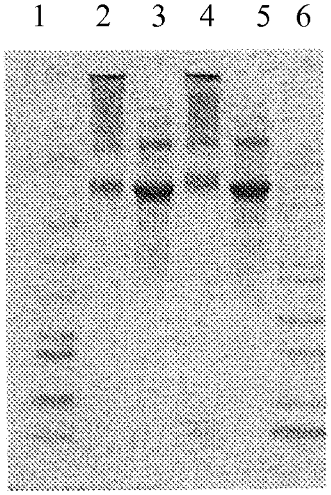
FIG. 4 is an image of a protein gel showing GnRH or 2GnRH peptide conjugated to keyhole limpet hemocyanin (KLH). The proteins were separated on 4-12% SDS-PAGE gels. GnRH-KLH and 2GnRH-KLH are shown in lanes 2 and 4, respectively. Lanes 1 and 6 contain molecular weight markers. Lanes 3 and 5 show KLH standard.

The GnRH peptide (in bold): NH2—CEHWSYGLRPG-COOH (SEQ ID NO: 55), and 2GnRH peptide (in bold): NH2-CEHWSYGLRPGEHWSYGLRPG-COOH (SEQ ID NO: 56) were synthesized with an extra cysteine (C, italic in the sequence) at the amino terminus. The purity of peptides 1780 and 1781 were verified using Micro HPLC and MALDI mass spectrometric analyses. KLH was then conjugated through the extra amino terminal C residue to the 1780 and 1781 peptides. The conjugation efficiency was verified through SDS-PAGE (FIG. 4).

Growth Characteristics and Pathogenicity of the Rearranged RV ERAg3p

Figure 2A:
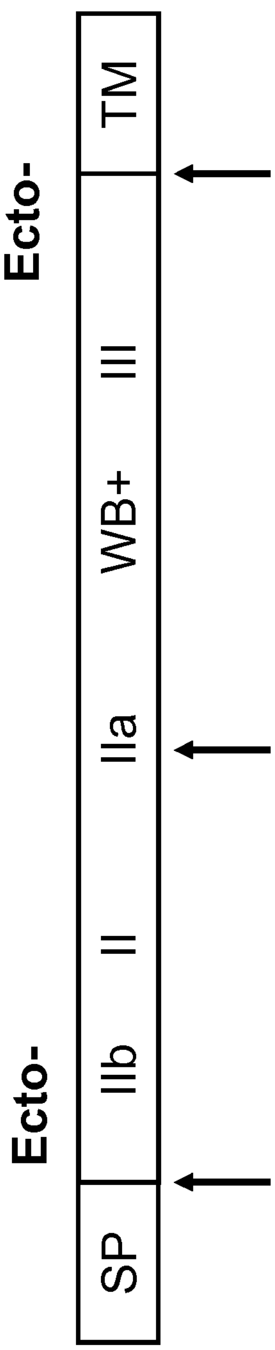
FIG. 2A is a schematic depiction of the rabies virus glycoprotein. Arrows indicate locations where either one or two copies of GnRH were inserted. Recombinant viruses with GnRH inserted at each of these locations were successfully recovered by reverse genetics (Ecto=ectodomain; SP=signal peptide; TM=transmembrane; IIb, II, IIa, WB+ and III refer to antigenic sites).
Figure 2B:
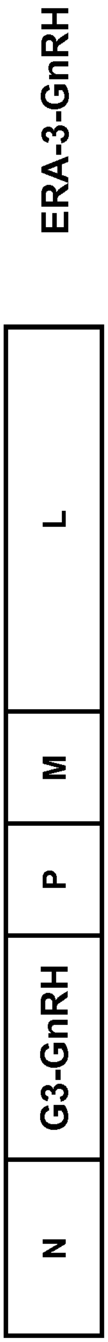
FIG. 2B is a schematic depiction of recombinant rabies virus ERA-3-GnRH.

The rearranged ERA genome with the G gene relocated ahead of the P gene was constructed similarly to the previously described method of Wu et al. (*Virus Res.* 129: 91-103, 2007). Mutagenesis of the G gene at amino acid residue 333 from AGA to GAG was described elsewhere (Wu and Rupprecht, *Virus Res.* 131: 95-99, 2008). The recovered ERAg3p grew as well as parental ERA virus, reaching $4.2 \times 10^9$ FFU/ml in infected BSR cells in bioreactor incubation (FIG. 2B). Intracranial inoculation of the ERAg3p into 3-week old mice did not cause any signs of rabies, or other adverse side-effects. However, parental ERA virus killed all the mice inoculated by the same route (FIG. 2C). Therefore, the attenuated ERAg3p virus was used as a backbone for subsequent insertion of the GnRH coding sequence in immunocontraceptive studies.

Figure 6:
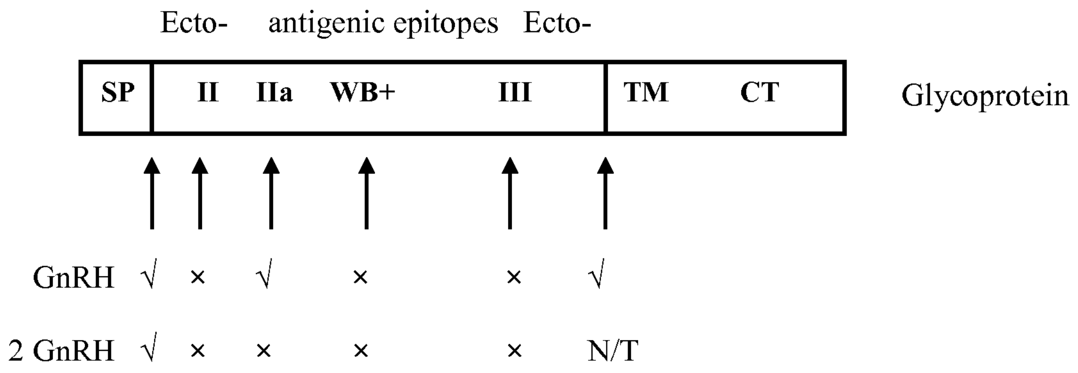
FIG. 6 is a schematic showing insertion sites of GnRH or 2GnRH coding sequence into the G gene in ERAg3p rabies virus. SP=signal peptide; TM=transmembrane; CT=cytoplasmic tail; N=amino terminus of glycoprotein; and C=carboxyl-terminus of glycoprotein.

Insertion of the Coding Sequence of GnRH into Various Locations of the G Gene in RV ERAg3p Virus Six locations of the G* gene in RV ERAg3p were selected for insertion of GnRH coding sequence based upon previously identified antigenic epitopes: immediately after signal sequence; antigenic site II; antigenic site IIa; antigenic site WB+; antigenic site III; and the junction between the ecto- and transmembrane domains (see FIG. 6) (Coulon et al., *J. Gen. Virol.* 64: 693-696, 1983; Seif et al., *J. Virol.* 53: 926-934, 1985; Prehaud et al., *J. Virol.* 62: 1-7, 1988). The coding sequence for GnRH (GAACACTGGAGCTACGGTTTGAGACCCGGG; SEQ ID NO: 47) was introduced into the above 6 locations through mutagenesis. The 2GnRH coding sequence linked in tandem (GAACACTGGAGCTACGGTTTGAGACCCGGGGAACACTGGAGCTACG GTTTGAGACCCGGG; SEQ ID NO: 57) was also incorporated into the G* gene in a similar way. The final 12 G* gene constructs were verified by DNA sequencing, and were successfully cloned into the RV ERAg3p full length plasmid for virus recovery. The nucleotide and amino acid sequences of the four G* gene constructs that were recovered in recombinant rabies viruses (see Table 3) are set forth as SEQ ID NOs: 49 and 50 (G-N-GnRH); SEQ ID NOs: 51 and 52 (G-N-2GnRH); SEQ ID NOs: 53 and 54 (G-IIa-GnRH); and SEQ ID NOs: 63 and 64 (G-C-GnRH).

Recovery and Characterization of the GnRH-Carrying ERAg3p Viruses

Figure 7A:
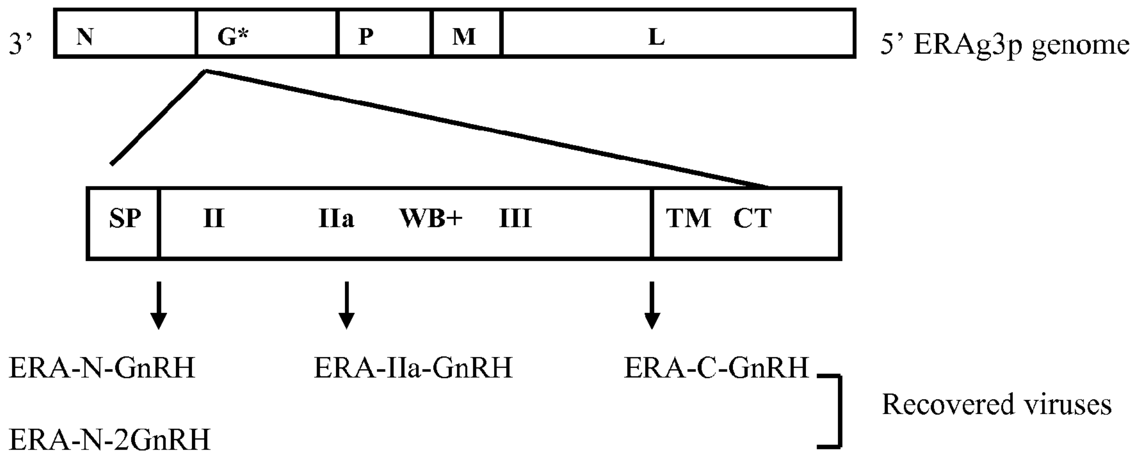
FIG. 7A is a schematic showing insertion sites of GnRH into the ERAg3p genome to generate ERA-N-GnRH, ERA-N-2GnRH, ERA-IIa-GnRH and ERA-C-GnRH.
Figure 7B:
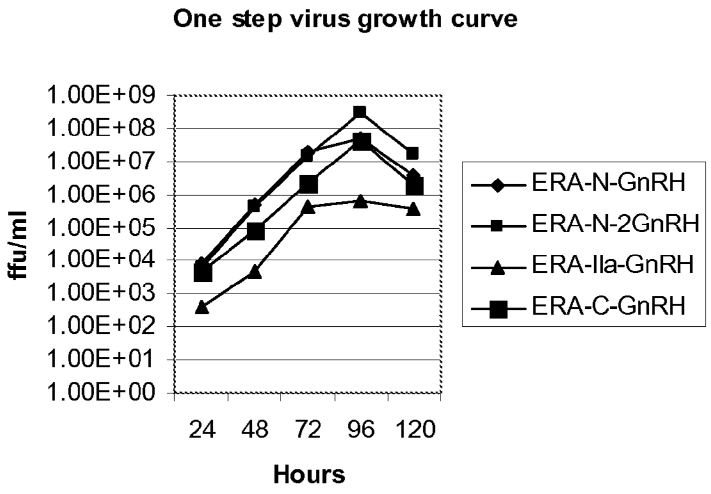
FIG. 7B is a line graph showing recovery and growth characteristics of the GnRH-carrying ERAg3p viruses. Recombinant virus was successfully recovered from 4 out of the 12 constructs. Recovered viruses contained GnRH inserted at the amino terminus immediate after the signal sequence, the IIa antigenic site, or the junction between the ectodomain and transmembrane domain of glycoprotein.

Each of the 12 G* constructs (FIG. 6) with GnRH or (2GnRH) in-frame fused to the G gene was successfully cloned ahead of the P gene in the RV ERAg3p genome. The full-length sequence of each construct was confirmed to be correct before virus recovery. Recombinant virus was successfully recovered from 4 out of the 12 constructs in which the GnRH was inserted at amino terminus immediately after the signal sequence (the recovered virus was named RV ERA-N-GnRH or ERA-N-2GnRH), IIa site (RV ERA-IIa-GnRH), or the junction between the ecto- and transmembrane domains (RV ERA-C-GnRH) of the glycoprotein (see Table 3 below). Plasmid transfection tests for virus rescue were repeated in two separate trials if no virus was detected in the first round of recovery. The recovered RV ERA-N-GnRH, ERA-N-2GnRH and ERA-C-GnRH grew well in cell culture, but the ERA-IIa-GnRH virus did not grow efficiently, and the titer was about 100 times lower than its counterparts (FIG. 7B).

TABLE 3

Recovery of GnRH-carrying ERAg3p viruses

| Virus construct | G gene construct | Virus recovered |
|---|---|---|
| ERA-N-GnRH | G-N-GnRH | Yes |
| ERA-N-2GnRH | G-N-2GnRH | Yes |
| ERA-II-GnRH | G-II-GnRH | No |
| ERA-II-2GnRH | G-II-2GnRH | No |
| ERA-IIa-GnRH | G-IIa-GnRH | Yes |
| ERA-IIa-2GnRH | G-IIa-2GnRH | No |
| ERA-WB + GnRH | G-WB + GnRH | No |
| ERA-WB + 2GnRH | G-WB + 2GnRH | No |
| ERA-III-GnRH | G-III-GnRH | No |
| ERA-III-2GnRH | G-III-2GnRH | No |
| ERA-C-GnRH | G-C-GnRH | Yes |
| ERA-C-2GnRH | G-C-2GnRH | Not tested |

Expression of GnRH in the RV ERAg3p Viruses

Figure 8A:
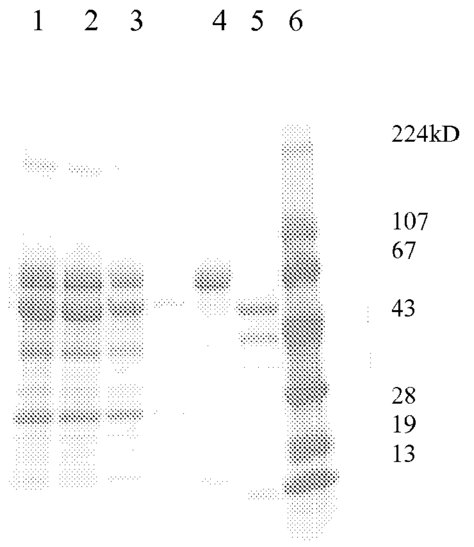
FIG. 8A is an image of an electrophoretic gel showing purified ERA-N-2GnRH (lane 1), ERA-N-GnRH (lane 2) and ERA-IIa-GnRH (lane 3). Purified virus was separated on 4-12% SDS-PAGE gels. Lanes 4 and 5 contain purified glycoprotein and purified nucleoprotein from rabies virus ERA as controls.
Figure 8B:
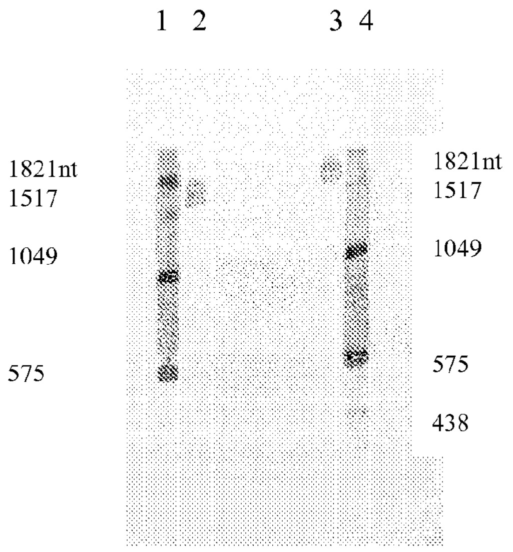
FIG. 8B is an image of a Northern blot of purified ERA-N-2GnRH (lane 2) and ERA-N-GnRH (lane 3). Lanes 1 and 4 contain RNA molecular weight marker.

The GnRH inserted between the ecto- and transmembrane domains of the G protein may not be in an optimal position for exposure to the virus surface. Thus, the following studies described herein focused on RV ERA-N-2GnRH, ERA-N-GnRH and ERA-IIa-GnRH. Through SDS-PAGE of purified viruses, a typical 5-band pattern was stained by Coomassie blue (FIG. 8A). The G protein bands from RV ERA-N-GnRH and ERA-N-2GnRH were excised from the gel for protein sequence analysis. The amino terminus of the G protein was verified to be blocked after fusion to the GnRH peptide in three independent trials. However, GnRH was detected in the fused G mRNA using Northern-blot in both ERA-N-2GnRH and ERA-N-GnRH viruses (FIG. 8B).

Figure 9:
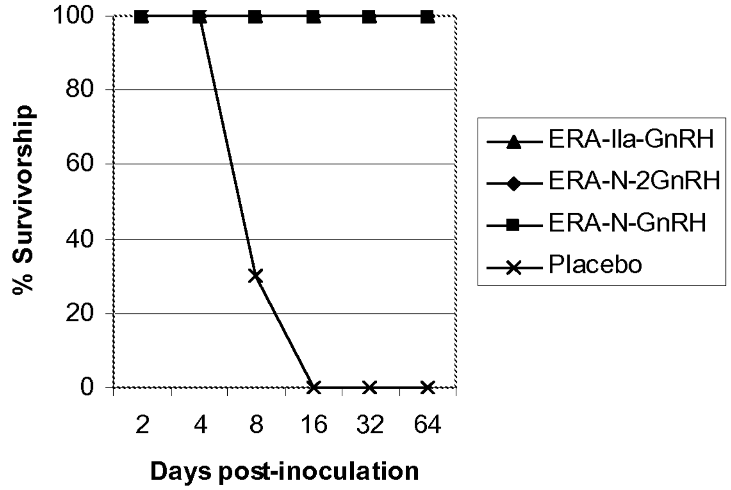
FIG. 9 is a line graph showing safety and potency of the GnRH-carrying ERAg3p viruses in a mouse model. No obvious side-effects were observed after intramuscular injection of ERA-N-2GnRH, ERA-N-GnRH or ERA-IIa-GnRH in mice. Three weeks post-inoculation, all mice survived challenge with a lethal dose of approximately 2.5-10.0 $MICLD_{50}$ dog/coyote street rabies virus. The control mice (placebo injected) died between 8 and 10 days after challenge. The surviving mice remained healthy before termination of the experiment at 2 months.

Safety and Potency Against Rabies Using the GnRH-Carrying RV ERAg3p Viruses in a Mouse Model No obvious side-effects or behavior changes were observed in mice inoculated with RV ERA-N-2GnRH, ERA-N-GnRH or ERA-IIa-GnRH. Surviving animals were challenged 3 weeks post-inoculation with a lethal dose of about 2.5-10.0 $MICLD_{50}$ dog/coyote street RV. All control mice developed typical rabies signs, and were euthanized between 8 and 10 days. RV antigen was detected in the brain by DFA. The surviving mice in the GnRH-carrying RV ERAg3p groups did not develop any signs of rabies, and remained healthy before termination of the experiment in 2 months (FIG. 9).

Figures 10A, 10B, 10C, 10D:
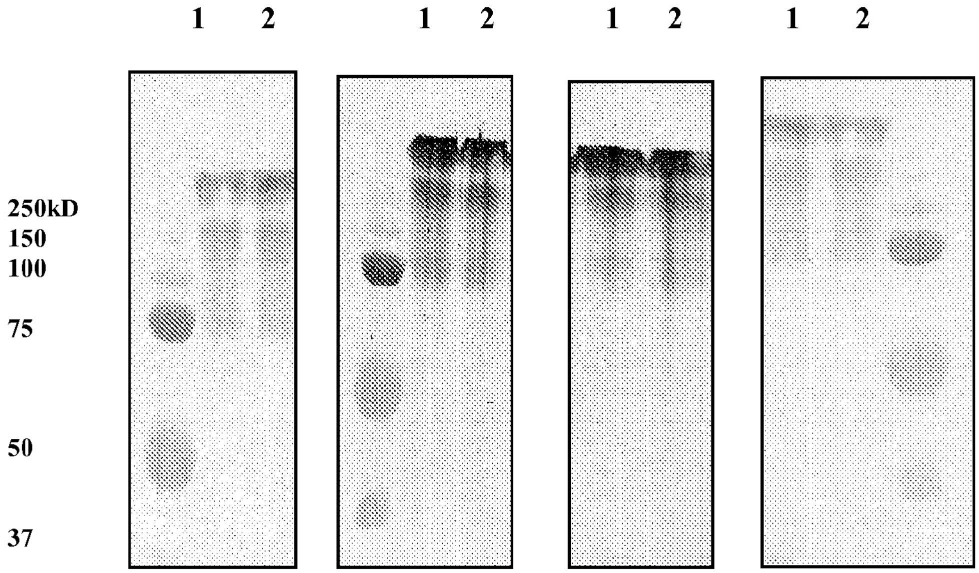
FIGS. 10A-10D are Western blots showing reaction of GnRH-KLH and 2GnRH-KLH conjugates against mouse serum immunized with GnRH-carrying ERA viruses and GonaCon™ serum. For each blot, Lanes 1 and 2 contain GnRH-KLH and 2GnRH-KLH, respectively. Shown are mouse serum from rabies virus ERA-IIa-GnRH immunization (A); mouse serum from RV ERA-N-GnRH immunization (B); mouse serum from ERA-N-2GnRH immunization (C); and rabbit serum against GonaCon™ (D). No differences were detected between mouse and rabbit serum against the GnRH conjugates.

Reaction of Immunized Mouse Serum Using the GnRH-Carrying RV ERAg3p Viruses Against GnRH-KLH and 2GnRH-KLH Conjugates To compare the reactivity of immunized mouse serum using the GnRH-carrying RV ERA viruses with that of GonaCon™ immunized rabbit serum (from the USDA) against GnRH-KLH and 2GnRH-KLH, the peptide conjugates were separated on 4-12% SDS-PAGE gels. In Western blotting, both GnRH-carrying RV ERA immunized mouse serum and GonaCon™ immunized rabbit serum recognized the GnRH-KLH and 2GnRH-KLH conjugates (FIG. 10). However, each conjugate presented several bands in serology, indicating an un-unified or uncontrollable process in peptide linkage.

Reaction of GonaCon™ Immunized Rabbit Serum Against the GnRH-Carrying RV ERAg3p Viruses In the IFA, typical cell membrane florescence was observed in the ERA-N-2GnRH, ERA-N-GnRH and ERA-IIa-GnRH infected BSR cells. The staining pattern was compatible with that of rabies G protein in RV-infected cells. In the Western blot using purified virus against GonaCon™ immunized rabbit serum, the G protein band was stained, which is an indication of fusion of the GnRH peptide with RV glycoprotein.

Example 4

In Vivo Studies of ERA-GnRH in Canines

This example describes the testing of ERA-GnRH vaccine constructs (such as those disclosed herein) in dogs to establish safety and efficacy. Recombinant ERA-GnRH virus will be tested in dogs for dual evaluation of rabies efficacy and immunocontraceptive effects for population control. It is hypothesized that ERA-GnRH will elicit rabies virus neutralizing antibody and stabilize the population of the immunized dogs within 3 years after one dose. ERA-GnRH will be administered to approximately 100 dogs (50 male and 50 female) and another 20 dogs will serve as controls. Recombinant rabies viruses will be administrated intramuscularly at a dose of approximately $10^7$ FFU/ml, or will be administered orally at a dose of approximately $10^8$ FFU/ml. It is believed that around 70% of the immunized animals will remain sterile for a year, and the litter number will drop at least 50%.

Example 5

Vaccination of Dogs with a Rabies Virus-Based Immunocontraceptive

This example describes a rabies virus-based immunocontraceptive vaccination study to be carried out on rabies virus naïve dogs. Seven groups of stray, fully reproductive adult, rabies naïve dogs will be included in this experiment. The absence of rabies virus neutralizing antibodies (VNAs) in serum will be used to corroborate that the animals are rabies naïve. Groups will consist of 20 animals, each with a 1:1 male to female ratio to ensure that statistical significance for males and females within each group is achievable. Pregnancy will be ruled out before the start of the experiment. In addition, canine transmissible venereal tumor must be discarded in both males and females. All animals will be quarantined (at least 40 days) and undergo mandatory full de-worming.

Two groups (20 animals each) will be vaccinated with 1 mL of recombinant rabies virus (as disclosed herein) on day 0, and administered a single booster on day 21. One group will be vaccinated intramuscularly (i.m) and the other group orally. Two other groups (20 animals each) will be vaccinated with a single dose of 1 mL of recombinant rabies virus by i.m or oral administration on day 0. Control groups (20 animals each) will receive placebo (cell culture media, the same that was used in the virus propagation) intramuscularly or orally (by instillation). A third group, the contraception control group, will receive GonaCon™ (a GnRH immunocontraceptive vaccine) by i.m. injection. All groups will be labeled accordingly (such as by using different color collars or with a tattoo indicating the group number). The test and control groups are summarized below.

Group 1: 20 animals (10 males and 10 females) inoculated with 1 mL of construct by i.m. route, at day 0 and 21.

Group 2: 20 animals (10 males and 10 females) inoculated with 1 mL of construct by oral route, at day 0 and 21.

Group 3: 20 animals (10 males and 10 females) inoculated with 1 mL of construct once, i.m. route at day 0.

Group 4: 20 animals (10 males and 10 females) inoculated with 1 mL of construct once, oral route at day 0.

Group 5: 20 animals (10 males and 10 females) inoculated with 1 mL of cell culture media by i.m. route.

Group 6: 20 animals (10 males and 10 females) inoculated with 1 mL of cell culture media by oral route.

Group 7: Contraception control group with 20 animals (10 males and 10 females) inoculated with 1 mL of GonaCon™ by i.m. route.

Caging

For confinement purposes, big cages or kennels (e.g., 5 meters×5 meters) will be used to confine up to 10 dogs each. Males and females will be separated at all times to avoid fighting among males when females are in heat. In addition, the kennels or cages will be sufficient to protect all dogs from sun and rain. Fresh water will be available all the times.

Sampling Schedule and Monitoring

Serum samples will be taken from vaccination candidates for screening purposes (up to 200 or more dogs will be tested if necessary) in order to select the 140 appropriate animals (dogs of both genders in reproductive age) with no anti-rabies antibodies (see Table 4).

Serum samples will be taken from all 120 dogs (groups 1 to 6) every week during the entire experiment (days 0, 7, 14, 28, and if possible, 6 months later) to measure the titers of VNA and immunocontraceptive responses.

Contraception Challenge

Animals in all groups will mate with healthy reproductive adults. Ideally, in groups 3 and 4, mating will occur 4 weeks after vaccination (day 28). For animals that receive a booster immunization at day 21, animals should mate between 14 to 21 days after the booster. One healthy stud will be used for every five bitches. Males in placebo control groups can be used as studs for vaccinated dogs and female dogs in these groups will also be mated.

TABLE 4

Schedule Prior to the Study (Weeks 1-8)

| | Time in Weeks | | | | | | | |
|---|---|---|---|---|---|---|---|---|
| Activity | 1 | 2 | 3 | 4 | 5 | 6 | 7 | 8 |
| Recruiting process (gathering dogs, potential candidates) | X | X | X | | | | | |
| Pregnancy and CTVT tests | X | X | X | | | | | |
| De-worming | X | X | X | | X | | | |
| Preventive vaccinations | X | X | X | | | | | |
| Preventive vaccinations and treatment booster | | | | | X | | | |
| Bleeding | X | X | X | | | | | |
| Shipping sera samples to CDC | | | | X | | | | |
| Quarantine | X | X | X | X | X | X | X | |
| Detection of RVNA at CDC, screening process | | | | | | X | X | |
| Selection of 120 animals about 50% males and 50% females | | | | | | | | X |

TABLE 5

Schedule for the Study (Weeks 9-24 and up to 6 months)

| | Time in Weeks | | | | | | | | | | | | | | |
|---|---|---|---|---|---|---|---|---|---|---|---|---|---|---|---|
| Activity | 9 | 10 | 11 | 12 | 13 | 14 | 17 | 18 | 19 | 20 | 21 | 22 | 23 | 24 | Up to 6 months |
| Immunization with RABV[1] constructs group 3 and 4 | X | | | | | | | | | | | | | | |
| Inoculation of placebo to groups 5 and 6 | X | | | | | | | | | | | | | | |

TABLE 5-continued

| Schedule for the Study (Weeks 9-24 and up to 6 months) | | | | | | | | | | | | | | | |
|---|---|---|---|---|---|---|---|---|---|---|---|---|---|---|---|
| | Time in Weeks | | | | | | | | | | | | | | |
| Activity | 9 | 10 | 11 | 12 | 13 | 14 | 17 | 18 | 19 | 20 | 21 | 22 | 23 | 24 | Up to 6 months |
| Bleeding for all groups, serum separation and storage at −20° C. | X | X | X | X | X | X | X | X | X | X | | | | | |
| Booster with RABV constructs groups 1 and 2 | | | | X | | | | | | | | | | | |
| Shipping sera samples to CDC[2] | | | | | X | | | | X | | | | X | | |
| Detection of RVNA[3] at CDC | X | X | X | X | X | X | X | | | | | | | | |
| Fertility test for both genders | X | X | X | X | X | X | X | X | | X | | | | | X |
| Mating | | | | X | X | | X | X | | | | | | X | X |
| Pregnancy tests | | | | | | | | X | X | | X | X | | | |

[1]Recombinant rabies virus;
[2]Centers for Disease Control and Prevention;
[3]Rabies virus neutralizing antibody It is anticipated that approximately 70% of the immunized animals will remain sterile for a year, and the litter number will drop at least 50%. It is further believed that more than 80% of the animals will survive lethal doses of rabies virus challenge at the end of the study.

Example 6

In Vivo Safety, Immunogenicity and Efficacy Evaluation of Recombinant Rabies Virus Immunocontraceptive Vaccines in a Rodent Model The first phase of this study will test the efficacy of the rabies virus immunocontraceptive (GnRH) vaccines against rabies virus infections in mice. Twenty 4-week old mice will be divided into groups of males (n=10) and females (n=10) (20 mice for each vaccine, GonaCon™ and combination of vaccines and GonaCon™), and receive an experimental biologic on day 0 (50 μl via intramuscular injection into the left gastrocnemius muscle). On days 7, 14 and 28, blood will be collected from all mice by the submandibular collection technique and tested for the presence of rabies virus neutralizing antibodies (VNA), antibodies against GnRH, and testosterone and estrogens. Mice with detectable levels of rabies virus neutralizing antibodies will be challenged with rabies virus in the right gastrocnemius muscle on day 28 after vaccination. Animals will be euthanized at the first clinical signs of rabies. Brain and reproductive organs will be collected for histological examination.

Groups: 1) live recombinant vaccine with 1-8 copies of incorporated GnRH (8×20 mice); 2) inactivated recombinant vaccine with incorporated GnRH (20 mice); 3) commercial vaccine (20 mice); 4) GonaCon™ (20 mice); 5) live recombinant vaccine with incorporated GnRH (20 mice)+GonaCon™; 6) commercial vaccine+GonaCon™ (20 mice); 7) inactivated recombinant vaccine with incorporated GnRH (20 mice)+GonaCon™; 8) control group administered PBS (10 mice).

Expected Outcome: By the end of a 3-month observation period, at least 80% of immunized animals are expected to survive without sign of rabies.

Example 7

Intramuscular Contraception Trial in Rodents

Vaccination will be conducted as described above. Each group will contain 10 mice of each sex. Animals will be bled on days 7, 14, and 28 after vaccination to measure VNA against rabies virus and GnRH, as well as progesterone in female mice and testosterone in male mice. Each mouse in the recombinant vaccine groups will be matched with a control mouse of the opposite sex (non-vaccinated, fertile) in new housing on day 30 (total 40 mice per group). These 20 pairs will be kept for observation. Females will be checked for pregnancy every 2 days following matching.

To measure longevity of induced immune responses and correlation with infertility, mouse pairs will be kept together for an additional 6 months (or until females are pregnant), if females do not become pregnant within the first 18 days. Mice will be bled via the submandibular route bi-weekly. Female sex organs will be examined for pregnancy after euthanasia.

Expected Outcomes: By the end of 3 months, at least 80% of females are expected not to be pregnant and at least 80% of males are expected not to impregnate non-immunized females. Serological responses will correlate with fertility ratios. Two or more recombinant rabies viruses will be selected for oral contraceptive investigations.

If efficacy (infertility in vaccinated animals of both sexes) is achieved by the intramuscular route, the immunogenicity and efficacy of the vaccine by oral administration will be evaluated. Experimental design will be similar to the i.m. contraception trial.

Example 8

In Vivo Immunogenicity and Safety Study in a Dog Model

Efficacy trial (intramuscular administration): Efficacy of the recombinant immunocontraceptive vaccines against rabies virus infections and their ability to induce immune responses against the GnRH will be tested in male and female dogs. Each group will consist of 8 animals (4 males and 4 females). In the first phase, various selected vaccines, proven to be efficacious and immunogenic in rodent model, will be administered i.m. Blood will be collected on day 0 and subsequently once or twice a week for the first two months and monthly thereafter. Serum will be tested for the presence of rabies virus neutralizing antibodies and antibodies against GnRH. Levels of GnRH, progesterone and testosterone also will be measured. A control group of 4 dogs will receive a placebo injection. Four animals in each group (previously vaccinated with one of the generated rabies vaccine constructs with proven titer of rabies virus neutralizing antibodies) will be inoculated with rabies virus in the right gastrocnemius muscle on day 28 after vaccination. Animals will be observed and euthanized (intravenous injection of a barbituric acid derivative) at the first clinical signs of rabies. Brain and reproductive organs will be collected for histological examinations. Design of experimental groups will depend upon results from trials of these vaccines in rodent models. Given previous vaccination, survival of all experimental animals is expected.

Groups (8 Dogs Each): 1) live recombinant vaccine with incorporated GnRH; 2) inactivated recombinant vaccine with incorporated GnRH; 3) commercial vaccine; 4) GonaCon™; 5) rabies vaccine+GonaCon™; 6) APHIS/NWRC recombinant GnRH-VLP; and 7) control group (4 dogs). Phase 1 of the immunocontraceptive vaccine experiment would require a maximum of 52-60 animals. Depending upon the results of the safety, immunogenicity, and efficacy experiments with the vaccines administered i.m., oral administration of selected live attenuated vaccines with incorporated GnRH will be tested as well.

Expected Outcomes: By the end of a 1 year observation period, at least 80% of immunized animals are expected to survive without any sign of rabies, and at least some experimental groups are expected to have significant titers of anti-GnRH antibodies and significantly decreased levels of progesterone and testosterone.

Contraception Trial in Dogs: Efficacy of the best experimental vaccine with incorporated GnRH, proven immunogenic in efficacy trials above in rodents and dogs, will be tested for its ability to induce infertility in female dogs following intramuscular administration. The treated and control groups will consist of 10 and 5 animals, respectively.

Expected Outcomes: By the end of a 1 year observation period, at least 80% of immunized animals are expected to remain infertile, with significant titers of anti-GnRH antibodies and decreased levels of progesterone and testosterone. At least 50% of control animals are expected to successfully breed.

This disclosure provides recombinant rabies viruses comprising immunocontraceptive proteins. The disclosure further provides methods of simultaneously protecting non-human animals from rabies virus infection and inhibiting fertility of the animal. It will be apparent that the precise details of the methods described may be varied or modified without departing from the spirit of the described disclosure. We claim all such modifications and variations that fall within the scope and spirit of the claims below.

The invention claimed is:

1. A recombinant rabies virus, wherein the genome of the recombinant rabies virus comprises rabies virus nucleoprotein (N), phosphoprotein (P), matrix protein (M), glycoprotein (G) and RNA-dependent RNA polymerase (L) genes and a heterologous nucleic acid sequence encoding a gonadotropin-releasing hormone (GnRH) protein, wherein the heterologous nucleic acid sequence encoding the GnRH protein is at least 95% identical to SEQ ID NO: 47.

2. The recombinant rabies virus of claim 1, wherein the G gene is relocated between the N gene and the P gene in the genome of the recombinant rabies virus.

3. The recombinant rabies virus of claim 1, wherein the rabies virus glycoprotein comprises a Glu at amino acid position 333.

4. The recombinant rabies virus of claim 1, comprising two copies of the heterologous nucleic acid sequence encoding the GnRH protein.

5. The recombinant rabies virus of claim 1, wherein the heterologous nucleic acid molecule encoding the GnRH protein is inserted within the rabies virus glycoprotein gene.

6. The recombinant rabies virus of claim 5, wherein the heterologous nucleic acid sequence encoding the GnRH protein is inserted following the signal sequence (nucleotides 1-57 of SEQ ID NO: 49) of the glycoprotein gene.

7. The recombinant rabies virus of claim 6, wherein the glycoprotein gene comprises the nucleic acid sequence of SEQ ID NO: 49 or SEQ ID NO: 51.

8. The recombinant rabies virus of claim 5, wherein the heterologous nucleic acid sequence encoding the GnRH protein is inserted immediately following antigenic site Ha (nucleotide 663 of SEQ ID NO: 53) of the glycoprotein gene.

9. The recombinant rabies virus of claim 8, wherein the glycoprotein gene comprises the nucleic acid sequence of SEQ ID NO: 53.

10. The recombinant rabies virus of claim 5, wherein the heterologous nucleic acid sequence encoding the GnRH protein is inserted at the junction of the ectodomain and transmembrane domain (following nucleotide 1374 of SEQ ID NO: 63) of the glycoprotein gene.

11. The recombinant rabies virus of claim 10, wherein the glycoprotein gene comprises the nucleic acid sequence of SEQ ID NO: 63.

12. An immunogenic composition comprising the recombinant rabies virus of claim 1 and a pharmaceutically acceptable carrier, an adjuvant, or both.

13. A method of immunizing a non-human animal against rabies virus infection and inhibiting fertility of the animal, comprising administering to the animal a therapeutically effective amount of the immunogenic composition of claim 12.

14. The method of claim 13, wherein the animal is a dog, cat, rat, mouse, bat, fox, raccoon, squirrel, opossum, coyote or wolf.

15. The method of claim 13, wherein the immunogenic composition is administered orally.

16. The method of claim 13, wherein the immunogenic composition is administered through food-baits.

17. The method of claim 13, wherein the animal is a domestic animal.

18. The method of claim 13, wherein the animal is a wild animal.

* * * * *

UNITED STATES PATENT AND TRADEMARK OFFICE

CERTIFICATE OF CORRECTION

PATENT NO. : 8,524,247 B2
APPLICATION NO. : 13/062680
DATED : September 3, 2013
INVENTOR(S) : Wu et al.

It is certified that error appears in the above-identified patent and that said Letters Patent is hereby corrected as shown below:

In the Specification:

Column 4, line 27, "use to" should read –used to–

Column 13, line 25, "phenylalanine Examples" should read –phenylalanine. Examples–

Column 18, lines 2-3, "3′-N-G-P-M-L-S′" should read –3′-N-G-P-M-L-5′–

Column 24, line 43, "NM 213893" should read –NM_213893–

Column 32, line 34, "(i.c)" should read –(i.c.)–

Column 33, line 61, "(i.m)" should read –(i.m.)–

Column 33, line 62, "gestrocnemius" should read –gastrocnemius–

Column 34, line 5, "i.m in the gestrocnemius" should read –i.m. in the gastrocnemius–

Column 34, line 49, "CEHWSYGLRPG" should read –*C*EHWSYGLRPG–

Column 34, line 51, "CEHWSYGLRPGEHWSYGLRPG" should read –*C*EHWSYGLRPGEHWSYGLRPG–

Column 37, line 34, "(i.m)" should read –(i.m.)–

Column 37, line 36, "i.m" should read –i.m.–

In the Claims:

Claim 8, column 134, line 47, "site Ha" should read –site IIa–

Signed and Sealed this
Thirteenth Day of October, 2015

Michelle K. Lee
*Director of the United States Patent and Trademark Office*

SEQUENCE LISTING

```
<160> NUMBER OF SEQ ID NOS: 64

<210> SEQ ID NO 1
<211> LENGTH: 11930
<212> TYPE: DNA
<213> ORGANISM: Artificial Sequence
<220> FEATURE:
<223> OTHER INFORMATION: Recombinant Rabies Virus ERA Genome
<220> FEATURE:
<221> NAME/KEY: misc_feature
<222> LOCATION: (1)..(58)
<223> OTHER INFORMATION: Leader region
<220> FEATURE:
<221> NAME/KEY: CDS
<222> LOCATION: (71)..(1420)
<223> OTHER INFORMATION: N gene
<220> FEATURE:
<221> NAME/KEY: CDS
<222> LOCATION: (1514)..(2404)
<223> OTHER INFORMATION: P gene
<220> FEATURE:
<221> NAME/KEY: CDS
<222> LOCATION: (2496)..(3101)
<223> OTHER INFORMATION: M gene
<220> FEATURE:
<221> NAME/KEY: CDS
<222> LOCATION: (3317)..(4888)
<223> OTHER INFORMATION: G gene
<220> FEATURE:
<221> NAME/KEY: misc_feature
<222> LOCATION: (4370)..(4370)
<223> OTHER INFORMATION: n = a or g
<220> FEATURE:
<221> NAME/KEY: misc_feature
<222> LOCATION: (4371)..(4371)
<223> OTHER INFORMATION: n = g or a
<220> FEATURE:
<221> NAME/KEY: misc_feature
<222> LOCATION: (4372)..(4372)
<223> OTHER INFORMATION: n = a or g
```

```
<220> FEATURE:
<221> NAME/KEY: misc_feature
<222> LOCATION: (4963)..(5361)
<223> OTHER INFORMATION: Psi region
<220> FEATURE:
<221> NAME/KEY: CDS
<222> LOCATION: (5416)..(11796)
<223> OTHER INFORMATION: L gene
<220> FEATURE:
<221> NAME/KEY: misc_feature
<222> LOCATION: (11861)..(11930)
<223> OTHER INFORMATION: Trailer region

<400> SEQUENCE: 1

acgcttaaca accagatcaa agaaaaaaca gacattgtca attgcaaagc aaaaatgtaa      60

cacccctaca atg gat gcc gac aag att gta ttc aaa gtc aat aat cag       109
           Met Asp Ala Asp Lys Ile Val Phe Lys Val Asn Asn Gln
           1               5                   10

gtg gtc tct ttg aag cct gag att atc gtg gat caa cat gag tac aag      157
Val Val Ser Leu Lys Pro Glu Ile Ile Val Asp Gln His Glu Tyr Lys
    15                  20                  25

tac cct gcc atc aaa gat ttg aaa aag ccc tgt ata acc cta gga aag      205
Tyr Pro Ala Ile Lys Asp Leu Lys Lys Pro Cys Ile Thr Leu Gly Lys
30                  35                  40                  45

gct ccc gat tta aat aaa gca tac aag tca gtt ttg tca ggc atg agc      253
Ala Pro Asp Leu Asn Lys Ala Tyr Lys Ser Val Leu Ser Gly Met Ser
                50                  55                  60

gcc gcc aaa ctt gat cct gac gat gta tgt tcc tat ttg gca gcg gca      301
Ala Ala Lys Leu Asp Pro Asp Asp Val Cys Ser Tyr Leu Ala Ala Ala
            65                  70                  75

atg cag ttt ttt gag ggg aca tgt ccg gaa gac tgg acc agc tat gga      349
Met Gln Phe Phe Glu Gly Thr Cys Pro Glu Asp Trp Thr Ser Tyr Gly
        80                  85                  90

atc gtg att gca cga aaa gga gat aag atc acc cca ggt tct ctg gtg      397
Ile Val Ile Ala Arg Lys Gly Asp Lys Ile Thr Pro Gly Ser Leu Val
    95                  100                 105

gag ata aaa cgt act gat gta gaa ggg aat tgg gct ctg aca gga ggc      445
Glu Ile Lys Arg Thr Asp Val Glu Gly Asn Trp Ala Leu Thr Gly Gly
110                 115                 120                 125

atg gaa ctg aca aga gac ccc act gtc cct gag cat gcg tcc tta gtc      493
Met Glu Leu Thr Arg Asp Pro Thr Val Pro Glu His Ala Ser Leu Val
                130                 135                 140

ggt ctt ctc ttg agt ctg tat agg ttg agc aaa ata tcc ggg caa aac      541
Gly Leu Leu Leu Ser Leu Tyr Arg Leu Ser Lys Ile Ser Gly Gln Asn
            145                 150                 155

act ggt aac tat aag aca aac att gca gac agg ata gag cag att ttt      589
Thr Gly Asn Tyr Lys Thr Asn Ile Ala Asp Arg Ile Glu Gln Ile Phe
        160                 165                 170

gag aca gcc cct ttt gtt aaa atc gtg gaa cac cat act cta atg aca      637
Glu Thr Ala Pro Phe Val Lys Ile Val Glu His His Thr Leu Met Thr
    175                 180                 185

act cac aaa atg tgt gct aat tgg agt act ata cca aac ttc aga ttt      685
Thr His Lys Met Cys Ala Asn Trp Ser Thr Ile Pro Asn Phe Arg Phe
190                 195                 200                 205

ttg gcc gga acc tat gac atg ttt ttc tcc cgg att gag cat cta tat      733
Leu Ala Gly Thr Tyr Asp Met Phe Phe Ser Arg Ile Glu His Leu Tyr
                210                 215                 220

tca gca atc aga gtg ggc aca gtt gtc act gct tat gaa gac tgt tca      781
Ser Ala Ile Arg Val Gly Thr Val Val Thr Ala Tyr Glu Asp Cys Ser
            225                 230                 235

gga ctg gta tca ttt act ggg ttc ata aaa caa atc aat ctc acc gct      829
Gly Leu Val Ser Phe Thr Gly Phe Ile Lys Gln Ile Asn Leu Thr Ala
        240                 245                 250
```

-continued

```
aga gag gca ata cta tat ttc ttc cac aag aac ttt gag gaa gag ata      877
Arg Glu Ala Ile Leu Tyr Phe Phe His Lys Asn Phe Glu Glu Glu Ile
    255                 260                 265

aga aga atg ttt gag cca ggg cag gag aca gct gtt cct cac tct tat      925
Arg Arg Met Phe Glu Pro Gly Gln Glu Thr Ala Val Pro His Ser Tyr
270                 275                 280                 285

ttc atc cac ttc cgt tca cta ggc ttg agt ggg aaa tct cct tat tca      973
Phe Ile His Phe Arg Ser Leu Gly Leu Ser Gly Lys Ser Pro Tyr Ser
                290                 295                 300

tca aat gct gtt ggt cac gtg ttc aat ctc att cac ttt gta gga tgc     1021
Ser Asn Ala Val Gly His Val Phe Asn Leu Ile His Phe Val Gly Cys
            305                 310                 315

tat atg ggt caa gtc aga tcc cta aat gca acg gtt att gct gca tgt     1069
Tyr Met Gly Gln Val Arg Ser Leu Asn Ala Thr Val Ile Ala Ala Cys
        320                 325                 330

gct cct cat gaa atg tct gtt cta ggg ggc tat ctg gga gag gaa ttc     1117
Ala Pro His Glu Met Ser Val Leu Gly Gly Tyr Leu Gly Glu Glu Phe
    335                 340                 345

ttc ggg aaa ggg aca ttt gaa aga aga ttc ttc aga gat gag aaa gaa     1165
Phe Gly Lys Gly Thr Phe Glu Arg Arg Phe Phe Arg Asp Glu Lys Glu
350                 355                 360                 365

ctt caa gaa tac gag gcg gct gaa ctg aca aag act gac gta gca ctg     1213
Leu Gln Glu Tyr Glu Ala Ala Glu Leu Thr Lys Thr Asp Val Ala Leu
                370                 375                 380

gca gat gat gga act gtc aac tct gac gac gag gac tac ttc tca ggt     1261
Ala Asp Asp Gly Thr Val Asn Ser Asp Asp Glu Asp Tyr Phe Ser Gly
            385                 390                 395

gaa acc aga agt ccg gag gct gtt tat act cga atc atg atg aat gga     1309
Glu Thr Arg Ser Pro Glu Ala Val Tyr Thr Arg Ile Met Met Asn Gly
        400                 405                 410

ggt cga cta aag aga tct cac ata cgg aga tat gtc tca gtc agt tcc     1357
Gly Arg Leu Lys Arg Ser His Ile Arg Arg Tyr Val Ser Val Ser Ser
    415                 420                 425

aat cat caa gcc cgt cca aac tca ttc gcc gag ttt cta aac aag aca     1405
Asn His Gln Ala Arg Pro Asn Ser Phe Ala Glu Phe Leu Asn Lys Thr
430                 435                 440                 445

tat tcg agt gac tca taagaagttg aacaacaaaa tgccggaaat ctacggattg     1460
Tyr Ser Ser Asp Ser
                450

tgtatatcca tcatgaaaaa aactaacacc cctcctttcg aaccatccca aac atg      1516
                                                           Met

agc aag atc ttt gtc aat cct agt gct att aga gcc ggt ctg gcc gat     1564
Ser Lys Ile Phe Val Asn Pro Ser Ala Ile Arg Ala Gly Leu Ala Asp
            455                 460                 465

ctt gag atg gct gaa gaa act gtt gat ctg atc aat aga aat atc gaa     1612
Leu Glu Met Ala Glu Glu Thr Val Asp Leu Ile Asn Arg Asn Ile Glu
        470                 475                 480

gac aat cag gct cat ctc caa ggg gaa ccc ata gaa gtg gac aat ctc     1660
Asp Asn Gln Ala His Leu Gln Gly Glu Pro Ile Glu Val Asp Asn Leu
    485                 490                 495

cct gag gat atg ggg cga ctt cac ctg gat gat gga aaa tcg ccc aac     1708
Pro Glu Asp Met Gly Arg Leu His Leu Asp Asp Gly Lys Ser Pro Asn
500                 505                 510                 515

cct ggt gag atg gcc aag gtg gga gaa ggc aag tat cga gag gac ttt     1756
Pro Gly Glu Met Ala Lys Val Gly Glu Gly Lys Tyr Arg Glu Asp Phe
                520                 525                 530

cag atg gat gaa gga gag gat ctt agc ttc ctg ttc cag tca tac ctg     1804
Gln Met Asp Glu Gly Glu Asp Leu Ser Phe Leu Phe Gln Ser Tyr Leu
            535                 540                 545
```

-continued

```
gaa aat gtt gga gtc caa ata gtc aga caa atg agg tca gga gag aga     1852
Glu Asn Val Gly Val Gln Ile Val Arg Gln Met Arg Ser Gly Glu Arg
        550                 555                 560

ttt ctc aag ata tgg tca cag acc gta gaa gag att ata tcc tat gtc     1900
Phe Leu Lys Ile Trp Ser Gln Thr Val Glu Glu Ile Ile Ser Tyr Val
    565                 570                 575

gcg gtc aac ttt ccc aac cct cca gga aag tct tca gag gat aaa tca     1948
Ala Val Asn Phe Pro Asn Pro Pro Gly Lys Ser Ser Glu Asp Lys Ser
580                 585                 590                 595

acc cag act act ggc cga gag ctc aag aag gag aca aca ccc act cct     1996
Thr Gln Thr Thr Gly Arg Glu Leu Lys Lys Glu Thr Thr Pro Thr Pro
                600                 605                 610

tct cag aga gaa agc caa tca tcg aaa gcc agg atg gcg gct caa att     2044
Ser Gln Arg Glu Ser Gln Ser Ser Lys Ala Arg Met Ala Ala Gln Ile
            615                 620                 625

gct tct ggc cct cca gcc ctt gaa tgg tcg gcc acc aat gaa gag gat     2092
Ala Ser Gly Pro Pro Ala Leu Glu Trp Ser Ala Thr Asn Glu Glu Asp
        630                 635                 640

gat cta tca gtg gag gct gag atc gct cac cag att gca gaa agt ttc     2140
Asp Leu Ser Val Glu Ala Glu Ile Ala His Gln Ile Ala Glu Ser Phe
    645                 650                 655

tcc aaa aaa tat aag ttt ccc tct cga tcc tca ggg ata ctc ttg tat     2188
Ser Lys Lys Tyr Lys Phe Pro Ser Arg Ser Ser Gly Ile Leu Leu Tyr
660                 665                 670                 675

aat ttt gag caa ttg aaa atg aac ctt gat gat ata gtt aaa gag gca     2236
Asn Phe Glu Gln Leu Lys Met Asn Leu Asp Asp Ile Val Lys Glu Ala
                680                 685                 690

aaa aat gta cca ggt gtg acc cgt tta gcc cat gac ggg tcc aaa ctc     2284
Lys Asn Val Pro Gly Val Thr Arg Leu Ala His Asp Gly Ser Lys Leu
            695                 700                 705

ccc cta aga tgt gta ctg gga tgg gtc gct ttg gcc aac cct aag aaa     2332
Pro Leu Arg Cys Val Leu Gly Trp Val Ala Leu Ala Asn Pro Lys Lys
        710                 715                 720

ttc cag ttg tta gtc gaa tcc gac aag ctg agt aaa atc atg caa gat     2380
Phe Gln Leu Leu Val Glu Ser Asp Lys Leu Ser Lys Ile Met Gln Asp
    725                 730                 735

gac ttg aat cgc tat aca tct tgc taaccgaacc tctccactca gtccctctag    2434
Asp Leu Asn Arg Tyr Thr Ser Cys
740                 745

acaataaagt ccgagatgtc ctaaagtcaa catgaaaaaa acaggcaaca ccactgataa   2494

a atg aac ttt cta cgt aag ata gtg aaa aat tgc agg gac gag gac act   2543
  Met Asn Phe Leu Arg Lys Ile Val Lys Asn Cys Arg Asp Glu Asp Thr
          750                 755                 760

caa aaa ccc tct ccc gtg tca gcc cct ctg gat gac gat gac ttg tgg     2591
Gln Lys Pro Ser Pro Val Ser Ala Pro Leu Asp Asp Asp Asp Leu Trp
    765                 770                 775

ctt cca ccc cct gaa tac gtc ccg ctg aaa gaa ctt aca agc aag aag     2639
Leu Pro Pro Pro Glu Tyr Val Pro Leu Lys Glu Leu Thr Ser Lys Lys
780                 785                 790                 795

aac atg agg aac ttt tgt atc aac gga ggg gtt aaa gtg tgt agc ccg     2687
Asn Met Arg Asn Phe Cys Ile Asn Gly Gly Val Lys Val Cys Ser Pro
                800                 805                 810

aat ggt tac tcg ttc agg atc ctg cgg cac att ctg aaa tca ttc gac     2735
Asn Gly Tyr Ser Phe Arg Ile Leu Arg His Ile Leu Lys Ser Phe Asp
            815                 820                 825

gag ata tat tct ggg aat cat agg atg atc ggg tta gcc aaa gta gtt     2783
Glu Ile Tyr Ser Gly Asn His Arg Met Ile Gly Leu Ala Lys Val Val
        830                 835                 840

att gga ctg gct ttg tca gga tct cca gtc cct gag ggc atg aac tgg     2831
Ile Gly Leu Ala Leu Ser Gly Ser Pro Val Pro Glu Gly Met Asn Trp
```

-continued

```
    845                 850                 855

gta tac aaa ttg agg aga acc ttt atc ttc cag tgg gct gat tcc agg      2879
Val Tyr Lys Leu Arg Arg Thr Phe Ile Phe Gln Trp Ala Asp Ser Arg
860                 865                 870                 875

ggc cct ctt gaa ggg gag gag ttg gaa tac tct cag gag atc act tgg      2927
Gly Pro Leu Glu Gly Glu Glu Leu Glu Tyr Ser Gln Glu Ile Thr Trp
              880                 885                 890

gat gat gat act gag ttc gtc gga ttg caa ata aga gtg att gca aaa      2975
Asp Asp Asp Thr Glu Phe Val Gly Leu Gln Ile Arg Val Ile Ala Lys
            895                 900                 905

cag tgt cat atc cag ggc aga atc tgg tgt atc aac atg aac ccg aga      3023
Gln Cys His Ile Gln Gly Arg Ile Trp Cys Ile Asn Met Asn Pro Arg
        910                 915                 920

gca tgt caa cta tgg tct gac atg tct ctt cag aca caa agg tcc gaa      3071
Ala Cys Gln Leu Trp Ser Asp Met Ser Leu Gln Thr Gln Arg Ser Glu
    925                 930                 935

gag gac aaa gat tcc tct ctg ctt cta gaa taatcagatt atatcccgca        3121
Glu Asp Lys Asp Ser Ser Leu Leu Leu Glu
940                 945

aatttatcac ttgtttacct ctggaggaga gaacatatgg gctcaactcc aacccttggg   3181

agcaatataa caaaaaacat gttatggtgc cattaaaccg ctgcatttca tcaaagtcaa   3241

gttgattacc tttacatttt gatcctcttg gatgtgaaaa aaactattaa catccctcaa   3301

aagactcaag gaaag atg gtt cct cag gct ctc ctg ttt gta ccc ctt ctg     3352
                 Met Val Pro Gln Ala Leu Leu Phe Val Pro Leu Leu
                 950                 955                 960

gtt ttt cca ttg tgt ttt ggg aaa ttc cct att tac acg ata cca gac      3400
Val Phe Pro Leu Cys Phe Gly Lys Phe Pro Ile Tyr Thr Ile Pro Asp
            965                 970                 975

aag ctt ggt ccc tgg agc ccg att gac ata cat cac ctc agc tgc cca      3448
Lys Leu Gly Pro Trp Ser Pro Ile Asp Ile His His Leu Ser Cys Pro
        980                 985                 990

aac aat ttg gta gtg gag gac  gaa gga tgc acc aac  ctg tca ggg ttc    3496
Asn Asn Leu Val Val Glu Asp  Glu Gly Cys Thr Asn  Leu Ser Gly Phe
    995                 1000                 1005

tcc  tac atg gaa ctt aaa  gtt gga tac atc tta  gcc ata aaa atg      3541
Ser  Tyr Met Glu Leu Lys  Val Gly Tyr Ile Leu  Ala Ile Lys Met
1010                 1015                 1020

aac  ggg ttc act tgc aca  ggc gtt gtg acg gag  gct gaa acc tat      3586
Asn  Gly Phe Thr Cys Thr  Gly Val Val Thr Glu  Ala Glu Thr Tyr
1025                 1030                 1035

act  aac ttc gtt ggt tat  gtc aca acc acg ttc  aaa aga aag cat      3631
Thr  Asn Phe Val Gly Tyr  Val Thr Thr Thr Phe  Lys Arg Lys His
1040                 1045                 1050

ttc  cgc cca aca cca gat  gca tgt aga gcc gcg  tac aac tgg aag      3676
Phe  Arg Pro Thr Pro Asp  Ala Cys Arg Ala Ala  Tyr Asn Trp Lys
1055                 1060                 1065

atg  gcc ggt gac ccc aga  tat gaa gag tct cta  cac aat ccg tac      3721
Met  Ala Gly Asp Pro Arg  Tyr Glu Glu Ser Leu  His Asn Pro Tyr
1070                 1075                 1080

cct  gac tac cac tgg ctt  cga act gta aaa acc  acc aag gag tct      3766
Pro  Asp Tyr His Trp Leu  Arg Thr Val Lys Thr  Thr Lys Glu Ser
1085                 1090                 1095

ctc  gtt atc ata tct cca  agt gtg gca gat ttg  gac cca tat gac      3811
Leu  Val Ile Ile Ser Pro  Ser Val Ala Asp Leu  Asp Pro Tyr Asp
1100                 1105                 1110

aga  tcc ctt cac tcg agg  gtc ttc cct agc ggg  aag tgc tca gga      3856
Arg  Ser Leu His Ser Arg  Val Phe Pro Ser Gly  Lys Cys Ser Gly
1115                 1120                 1125
```

```
gta  gcg gtg tct tct acc  tac tgc tcc act aac  cac gat tac acc      3901
Val  Ala Val Ser Ser Thr  Tyr Cys Ser Thr Asn  His Asp Tyr Thr
1130                 1135                 1140

att  tgg atg ccc gag aat  ccg aga cta ggg atg  tct tgt gac att      3946
Ile  Trp Met Pro Glu Asn  Pro Arg Leu Gly Met  Ser Cys Asp Ile
1145                 1150                 1155

ttt  acc aat agt agg ggg  aag aga gca tcc aaa  ggg agt gag act      3991
Phe  Thr Asn Ser Arg Gly  Lys Arg Ala Ser Lys  Gly Ser Glu Thr
1160                 1165                 1170

tgc  ggc ttt gta gat gaa  aga ggc cta tat aag  tct tta aaa gga      4036
Cys  Gly Phe Val Asp Glu  Arg Gly Leu Tyr Lys  Ser Leu Lys Gly
1175                 1180                 1185

gca  tgc aaa ctc aag tta  tgt gga gtt cta gga  ctt aga ctt atg      4081
Ala  Cys Lys Leu Lys Leu  Cys Gly Val Leu Gly  Leu Arg Leu Met
1190                 1195                 1200

gat  gga aca tgg gtc gcg  atg caa aca tca aat  gaa acc aaa tgg      4126
Asp  Gly Thr Trp Val Ala  Met Gln Thr Ser Asn  Glu Thr Lys Trp
1205                 1210                 1215

tgc  ccc ccc gat cag ttg  gtg aac ctg cac gac  ttt cgc tca gac      4171
Cys  Pro Pro Asp Gln Leu  Val Asn Leu His Asp  Phe Arg Ser Asp
1220                 1225                 1230

gaa  att gag cac ctt gtt  gta gag gag ttg gtc  agg aag aga gag      4216
Glu  Ile Glu His Leu Val  Val Glu Glu Leu Val  Arg Lys Arg Glu
1235                 1240                 1245

gag  tgt ctg gat gca cta  gag tcc atc atg aca  acc aag tca gtg      4261
Glu  Cys Leu Asp Ala Leu  Glu Ser Ile Met Thr  Thr Lys Ser Val
1250                 1255                 1260

agt  ttc aga cgt ccc agt  cat tta aga aaa ctt  gtc cct ggg ttt      4306
Ser  Phe Arg Arg Pro Ser  His Leu Arg Lys Leu  Val Pro Gly Phe
1265                 1270                 1275

gga  aaa gca tat acc ata  ttc aac aag acc ttg  atg gaa gcc gat      4351
Gly  Lys Ala Tyr Thr Ile  Phe Asn Lys Thr Leu  Met Glu Ala Asp
1280                 1285                 1290

gct  cac tac aag tca gtc  nnn act tgg aat gag  atc ctc cct tca      4396
Ala  His Tyr Lys Ser Val  Xaa Thr Trp Asn Glu  Ile Leu Pro Ser
1295                 1300                 1305

aaa  ggg tgt tta aga gtt  ggg ggg agg tgt cat  cct cat gtg aac      4441
Lys  Gly Cys Leu Arg Val  Gly Gly Arg Cys His  Pro His Val Asn
1310                 1315                 1320

ggg  gtg ttt ttc aat ggt  ata ata tta gga cct  gac ggc aat gtc      4486
Gly  Val Phe Phe Asn Gly  Ile Ile Leu Gly Pro  Asp Gly Asn Val
1325                 1330                 1335

tta  atc cca gag atg caa  tca tcc ctc ctc cag  caa cat atg gag      4531
Leu  Ile Pro Glu Met Gln  Ser Ser Leu Leu Gln  Gln His Met Glu
1340                 1345                 1350

ttg  ttg gaa tcc tcg gtt  atc ccc ctt gtg cac  ccc ctg gca gac      4576
Leu  Leu Glu Ser Ser Val  Ile Pro Leu Val His  Pro Leu Ala Asp
1355                 1360                 1365

ccg  tct acc gtt ttc aag  gac ggt gac gag gct  gag gat ttt gtt      4621
Pro  Ser Thr Val Phe Lys  Asp Gly Asp Glu Ala  Glu Asp Phe Val
1370                 1375                 1380

gaa  gtt cac ctt ccc gat  gtg cac aat cag gtc  tca gga gtt gac      4666
Glu  Val His Leu Pro Asp  Val His Asn Gln Val  Ser Gly Val Asp
1385                 1390                 1395

ttg  ggt ctc ccg aac tgg  ggg aag tat gta tta  ctg agt gca ggg      4711
Leu  Gly Leu Pro Asn Trp  Gly Lys Tyr Val Leu  Leu Ser Ala Gly
1400                 1405                 1410

gcc  ctg act gcc ttg atg  ttg ata att ttc ctg  atg aca tgt tgt      4756
Ala  Leu Thr Ala Leu Met  Leu Ile Ile Phe Leu  Met Thr Cys Cys
1415                 1420                 1425
```

```
aga  aga gtc aat cga tca  gaa cct acg caa cac  aat ctc aga ggg      4801
Arg  Arg Val Asn Arg Ser  Glu Pro Thr Gln His  Asn Leu Arg Gly
1430                1435                1440

aca  ggg agg gag gtg tca  gtc act ccc caa agc  ggg aag atc ata      4846
Thr  Gly Arg Glu Val Ser  Val Thr Pro Gln Ser  Gly Lys Ile Ile
1445                1450                1455

tct  tca tgg gaa tca cac  aag agt ggg ggt gag  acc aga ctg          4888
Ser  Ser Trp Glu Ser His  Lys Ser Gly Gly Glu  Thr Arg Leu
1460                1465                1470

tgaggactgg ccgtcctttc aacgatccaa gtcctgaaga tcacctcccc ttggggggtt   4948

ctttttgaaa aaaacctggg ttcaatagtc ctcctcgaac tccatgcaac tgggtagatt   5008

caagagtcat gagattttca ttaatcctct cagttgatca agcaagatca tgtagattct   5068

cataataggg gagatcttct agcagtttca gtgactaacg gtactttcat tctccaggaa   5128

ctgacaccaa cagttgtaga caaaccacgg ggtgtctcgg gtgactctgt gcttgggcac   5188

agacaaaggt catggtgtgt tccatgatag cggactcagg atgagttaat tgagagaggc   5248

agtcttcctc ccgtgaagga cataagcagt agctcacaat catcccgcgt ctcagcaaag   5308

tgtgcataat tataaagtgc tgggtcatct aagcttttca gtcgagaaaa aaacattaga   5368

tcagaagaac aactggcaac acttctcaac ctgagaccta cttcaag atg ctc  gat    5424
                                                    Met Leu  Asp
                                                        1475

cct gga gag gtc  tat gat gac cct att  gac cca atc gag tta  gag      5469
Pro Gly Glu Val  Tyr Asp Asp Pro Ile  Asp Pro Ile Glu Leu  Glu
            1480                 1485                 1490

gat gaa ccc aga  gga acc ccc act gtc  ccc aac atc ttg agg  aac      5514
Asp Glu Pro Arg  Gly Thr Pro Thr Val  Pro Asn Ile Leu Arg  Asn
            1495                 1500                 1505

tct gac tac aat  ctc aac tct cct ttg  ata gaa gat cct gct  aga      5559
Ser Asp Tyr Asn  Leu Asn Ser Pro Leu  Ile Glu Asp Pro Ala  Arg
            1510                 1515                 1520

cta atg tta gaa  tgg tta aaa aca ggg  aat aga cct tat cgg  atg      5604
Leu Met Leu Glu  Trp Leu Lys Thr Gly  Asn Arg Pro Tyr Arg  Met
            1525                 1530                 1535

act cta aca gac  aat tgc tcc agg tct  ttc aga gtt ttg aaa  gat      5649
Thr Leu Thr Asp  Asn Cys Ser Arg Ser  Phe Arg Val Leu Lys  Asp
            1540                 1545                 1550

tat ttc aag aag  gta gat ttg ggt tct  ctc aag gtg ggc gga  atg      5694
Tyr Phe Lys Lys  Val Asp Leu Gly Ser  Leu Lys Val Gly Gly  Met
            1555                 1560                 1565

gct gca cag tca  atg att tct ctc tgg  tta tat ggt gcc cac  tct      5739
Ala Ala Gln Ser  Met Ile Ser Leu Trp  Leu Tyr Gly Ala His  Ser
            1570                 1575                 1580

gaa tcc aac agg  agc cgg aga tgt ata  aca gac ttg gcc cat  ttc      5784
Glu Ser Asn Arg  Ser Arg Arg Cys Ile  Thr Asp Leu Ala His  Phe
            1585                 1590                 1595

tat tcc aag tcg  tcc ccc ata gag aag  ctg ttg aat ctc acg  cta      5829
Tyr Ser Lys Ser  Ser Pro Ile Glu Lys  Leu Leu Asn Leu Thr  Leu
            1600                 1605                 1610

gga aat aga ggg  ctg aga atc ccc cca  gag gga gtg tta agt  tgc      5874
Gly Asn Arg Gly  Leu Arg Ile Pro Pro  Glu Gly Val Leu Ser  Cys
            1615                 1620                 1625

ctt gag agg gtt  gat tat gat aat gca  ttt gga agg tat ctt  gcc      5919
Leu Glu Arg Val  Asp Tyr Asp Asn Ala  Phe Gly Arg Tyr Leu  Ala
            1630                 1635                 1640

aac acg tat tcc  tct tac ttg ttc ttc  cat gta atc acc tta  tac      5964
Asn Thr Tyr Ser  Ser Tyr Leu Phe Phe  His Val Ile Thr Leu  Tyr
            1645                 1650                 1655
```

```
atg aac gcc cta  gac tgg gat gaa gaa  aag acc atc cta gca  tta      6009
Met Asn Ala Leu  Asp Trp Asp Glu Glu  Lys Thr Ile Leu Ala  Leu
            1660                 1665                 1670

tgg aaa gat tta  acc tca gtg gac atc  ggg aag gac ttg gta  aag      6054
Trp Lys Asp Leu  Thr Ser Val Asp Ile  Gly Lys Asp Leu Val  Lys
            1675                 1680                 1685

ttc aaa gac caa  ata tgg gga ctg ccg  atc gtg aca aag gac  ttt      6099
Phe Lys Asp Gln  Ile Trp Gly Leu Pro  Ile Val Thr Lys Asp  Phe
            1690                 1695                 1700

gtt tac tcc caa  agt tcc aat tgt ctt  ttt gac aga aac tac  aca      6144
Val Tyr Ser Gln  Ser Ser Asn Cys Leu  Phe Asp Arg Asn Tyr  Thr
            1705                 1710                 1715

ctt atg cta aaa  gaa ctt ttc ttg tct  cgc ttc aac tcc tta  atg      6189
Leu Met Leu Lys  Glu Leu Phe Leu Ser  Arg Phe Asn Ser Leu  Met
            1720                 1725                 1730

gtc ttg ctc tct  ccc cca gag ccc cga  tac tca gat gac ttg  ata      6234
Val Leu Leu Ser  Pro Pro Glu Pro Arg  Tyr Ser Asp Asp Leu  Ile
            1735                 1740                 1745

tct caa cta tgc  cag ctg tac att gct  ggg gat caa gtc ttg  tct      6279
Ser Gln Leu Cys  Gln Leu Tyr Ile Ala  Gly Asp Gln Val Leu  Ser
            1750                 1755                 1760

atg tgt gga aac  tcc ggc tat gaa gtc  atc aaa ata ttg gag  cca      6324
Met Cys Gly Asn  Ser Gly Tyr Glu Val  Ile Lys Ile Leu Glu  Pro
            1765                 1770                 1775

tat gtc gtg aat  agt tta gtc cag aga  gca gaa aag ttt agg  cct      6369
Tyr Val Val Asn  Ser Leu Val Gln Arg  Ala Glu Lys Phe Arg  Pro
            1780                 1785                 1790

ctc att cat tcc  ttg gga gac ttt cct  gta ttt ata aaa gac  aag      6414
Leu Ile His Ser  Leu Gly Asp Phe Pro  Val Phe Ile Lys Asp  Lys
            1795                 1800                 1805

gta agt caa ctt  gaa gag acg ttc ggt  ccc tgt gca aga agg  ttc      6459
Val Ser Gln Leu  Glu Glu Thr Phe Gly  Pro Cys Ala Arg Arg  Phe
            1810                 1815                 1820

ttt agg gct ctg  gat caa ttc gac aac  ata cat gac ttg gtt  ttt      6504
Phe Arg Ala Leu  Asp Gln Phe Asp Asn  Ile His Asp Leu Val  Phe
            1825                 1830                 1835

gtg tat ggc tgt  tac agg cat tgg ggg  cac cca tat ata gat  tat      6549
Val Tyr Gly Cys  Tyr Arg His Trp Gly  His Pro Tyr Ile Asp  Tyr
            1840                 1845                 1850

cga aag ggt ctg  tca aaa cta tat gat  cag gtt cac att aaa  aaa      6594
Arg Lys Gly Leu  Ser Lys Leu Tyr Asp  Gln Val His Ile Lys  Lys
            1855                 1860                 1865

gtg ata gat aag  tcc tac cag gag tgc  tta gca agc gac cta  gcc      6639
Val Ile Asp Lys  Ser Tyr Gln Glu Cys  Leu Ala Ser Asp Leu  Ala
            1870                 1875                 1880

agg agg atc ctt  aga tgg ggt ttt gat  aag tac tcc aag tgg  tat      6684
Arg Arg Ile Leu  Arg Trp Gly Phe Asp  Lys Tyr Ser Lys Trp  Tyr
            1885                 1890                 1895

ctg gat tca aga  ttc cta gcc cga gac  cac ccc ttg act ccc  tat      6729
Leu Asp Ser Arg  Phe Leu Ala Arg Asp  His Pro Leu Thr Pro  Tyr
            1900                 1905                 1910

atc aaa acc caa  aca tgg cca ccc aaa  cat att gta gac ttg  gtg      6774
Ile Lys Thr Gln  Thr Trp Pro Pro Lys  His Ile Val Asp Leu  Val
            1915                 1920                 1925

ggg gat aca tgg  cac aag ctc ccg atc  acg cag atc ttt gag  att      6819
Gly Asp Thr Trp  His Lys Leu Pro Ile  Thr Gln Ile Phe Glu  Ile
            1930                 1935                 1940

cct gaa tca atg  gat ccg tca gaa ata  ttg gat gac aaa tca  cat      6864
Pro Glu Ser Met  Asp Pro Ser Glu Ile  Leu Asp Asp Lys Ser  His
            1945                 1950                 1955
```

-continued

```
tct ttc acc aga  acg aga cta gct tct  tgg ctg tca gaa aac  cga      6909
Ser Phe Thr Arg  Thr Arg Leu Ala Ser  Trp Leu Ser Glu Asn  Arg
            1960                 1965                 1970

ggg gga cct gtt  cct agc gaa aaa gtt  att atc acg gcc ctg  tct      6954
Gly Gly Pro Val  Pro Ser Glu Lys Val  Ile Ile Thr Ala Leu  Ser
            1975                 1980                 1985

aag ccg cct gtc  aat ccc cga gag ttt  ctg agg tct ata gac  ctc      6999
Lys Pro Pro Val  Asn Pro Arg Glu Phe  Leu Arg Ser Ile Asp  Leu
            1990                 1995                 2000

gga gga ttg cca  gat gaa gac ttg ata  att ggc ctc aag cca  aag      7044
Gly Gly Leu Pro  Asp Glu Asp Leu Ile  Ile Gly Leu Lys Pro  Lys
            2005                 2010                 2015

gaa cgg gaa ttg  aag att gaa ggt cga  ttc ttt gct cta atg  tca      7089
Glu Arg Glu Leu  Lys Ile Glu Gly Arg  Phe Phe Ala Leu Met  Ser
            2020                 2025                 2030

tgg aat cta aga  ttg tat ttt gtc atc  act gaa aaa ctc ttg  gcc      7134
Trp Asn Leu Arg  Leu Tyr Phe Val Ile  Thr Glu Lys Leu Leu  Ala
            2035                 2040                 2045

aac tac atc ttg  cca ctt ttt gac gcg  ctg act atg aca gac  aac      7179
Asn Tyr Ile Leu  Pro Leu Phe Asp Ala  Leu Thr Met Thr Asp  Asn
            2050                 2055                 2060

ctg aac aag gtg  ttt aaa aag ctg atc  gac agg gtc acc ggg  caa      7224
Leu Asn Lys Val  Phe Lys Lys Leu Ile  Asp Arg Val Thr Gly  Gln
            2065                 2070                 2075

ggg ctt ttg gac  tat tca agg gtc aca  tat gca ttt cac ctg  gac      7269
Gly Leu Leu Asp  Tyr Ser Arg Val Thr  Tyr Ala Phe His Leu  Asp
            2080                 2085                 2090

tat gaa aag tgg  aac aac cat caa aga  tta gag tca aca gag  gat      7314
Tyr Glu Lys Trp  Asn Asn His Gln Arg  Leu Glu Ser Thr Glu  Asp
            2095                 2100                 2105

gta ttt tct gtc  cta gat caa gtg ttt  gga ttg aag aga gtg  ttt      7359
Val Phe Ser Val  Leu Asp Gln Val Phe  Gly Leu Lys Arg Val  Phe
            2110                 2115                 2120

tct aga aca cac  gag ttt ttt caa aag  gcc tgg atc tat tat  tca      7404
Ser Arg Thr His  Glu Phe Phe Gln Lys  Ala Trp Ile Tyr Tyr  Ser
            2125                 2130                 2135

gac aga tca gac  ctc atc ggg tta cgg  gag gat caa ata tac  tgc      7449
Asp Arg Ser Asp  Leu Ile Gly Leu Arg  Glu Asp Gln Ile Tyr  Cys
            2140                 2145                 2150

tta gat gcg tcc  aac ggc cca acc tgt  tgg aat ggc cag gat  ggc      7494
Leu Asp Ala Ser  Asn Gly Pro Thr Cys  Trp Asn Gly Gln Asp  Gly
            2155                 2160                 2165

ggg cta gaa ggc  tta cgg cag aag ggc  tgg agt cta gtc agc  tta      7539
Gly Leu Glu Gly  Leu Arg Gln Lys Gly  Trp Ser Leu Val Ser  Leu
            2170                 2175                 2180

ttg atg ata gat  aga gaa tct caa atc  agg aac aca aga acc  aaa      7584
Leu Met Ile Asp  Arg Glu Ser Gln Ile  Arg Asn Thr Arg Thr  Lys
            2185                 2190                 2195

ata cta gct caa  gga gac aac cag gtt  tta tgt ccg aca tat  atg      7629
Ile Leu Ala Gln  Gly Asp Asn Gln Val  Leu Cys Pro Thr Tyr  Met
            2200                 2205                 2210

ttg tcg cca ggg  cta tct caa gag ggg  ctc ctc tat gaa ttg  gag      7674
Leu Ser Pro Gly  Leu Ser Gln Glu Gly  Leu Leu Tyr Glu Leu  Glu
            2215                 2220                 2225

aga ata tca agg  aat gca ctt tcg ata  tac aga gcc gtc gag  gaa      7719
Arg Ile Ser Arg  Asn Ala Leu Ser Ile  Tyr Arg Ala Val Glu  Glu
            2230                 2235                 2240

ggg gca tct aag  cta ggg ctg atc acc  aag aaa gaa gag acc  atg      7764
Gly Ala Ser Lys  Leu Gly Leu Ile Thr  Lys Lys Glu Glu Thr  Met
            2245                 2250                 2255
```

-continued

```
tgt agt tat gac  ttc ctc atc tat gga  aaa acc cct ttg ttt  aga       7809
Cys Ser Tyr Asp  Phe Leu Ile Tyr Gly  Lys Thr Pro Leu Phe  Arg
            2260                 2265                 2270

ggt aac ata ttg  gtg cct gag tcc aaa  aga tgg gcc aga gtc  tct       7854
Gly Asn Ile Leu  Val Pro Glu Ser Lys  Arg Trp Ala Arg Val  Ser
            2275                 2280                 2285

tgc gtc tct aat  gac caa ata gtc aac  ctc gcc aat ata atg  tcg       7899
Cys Val Ser Asn  Asp Gln Ile Val Asn  Leu Ala Asn Ile Met  Ser
            2290                 2295                 2300

aca gtg tcc acc  aat gcg cta aca gtg  gca caa cac tct caa  tct       7944
Thr Val Ser Thr  Asn Ala Leu Thr Val  Ala Gln His Ser Gln  Ser
            2305                 2310                 2315

ttg atc aaa ccg  atg ggg gat ttt ctg  ctc atg tca gta cag  gca       7989
Leu Ile Lys Pro  Met Gly Asp Phe Leu  Leu Met Ser Val Gln  Ala
            2320                 2325                 2330

gtc ttt cac tac  ctg cta ttt agc cca  atc tta aag gga aga  gtt       8034
Val Phe His Tyr  Leu Leu Phe Ser Pro  Ile Leu Lys Gly Arg  Val
            2335                 2340                 2345

tac aag att ctg  agc gct gaa ggg gat  agc ttt ctc cta gcc  atg       8079
Tyr Lys Ile Leu  Ser Ala Glu Gly Asp  Ser Phe Leu Leu Ala  Met
            2350                 2355                 2360

tca agg ata atc  tat cta gat cct tct  ttg gga ggg gta tct  gga       8124
Ser Arg Ile Ile  Tyr Leu Asp Pro Ser  Leu Gly Gly Val Ser  Gly
            2365                 2370                 2375

atg tcc ctc gga  aga ttc cat ata cga  cag ttc tca gac cct  gtc       8169
Met Ser Leu Gly  Arg Phe His Ile Arg  Gln Phe Ser Asp Pro  Val
            2380                 2385                 2390

tct gaa ggg tta  tcc ttc tgg aga gag  atc tgg tta agc tcc  cac       8214
Ser Glu Gly Leu  Ser Phe Trp Arg Glu  Ile Trp Leu Ser Ser  His
            2395                 2400                 2405

gag tcc tgg gtt  cac gcg ttg tgt caa  gag gct gga aac cca  gat       8259
Glu Ser Trp Val  His Ala Leu Cys Gln  Glu Ala Gly Asn Pro  Asp
            2410                 2415                 2420

ctt gga gag aga  aca ctc gag agc ttc  act cgc ctt cta gaa  gat       8304
Leu Gly Glu Arg  Thr Leu Glu Ser Phe  Thr Arg Leu Leu Glu  Asp
            2425                 2430                 2435

cct acc acc tta  aat atc aga gga ggg  gcc agt cct acc att  cta       8349
Pro Thr Thr Leu  Asn Ile Arg Gly Gly  Ala Ser Pro Thr Ile  Leu
            2440                 2445                 2450

ctc aag gat gca  atc aga aag gct tta  tat gac gag gtg gac  aag       8394
Leu Lys Asp Ala  Ile Arg Lys Ala Leu  Tyr Asp Glu Val Asp  Lys
            2455                 2460                 2465

gtg gag aat tca  gag ttt cga gag gca  atc ctg ttg tcc aag  acc       8439
Val Glu Asn Ser  Glu Phe Arg Glu Ala  Ile Leu Leu Ser Lys  Thr
            2470                 2475                 2480

cat aga gat aat  ttt ata ctc ttc tta  aca tct gtt gag cct  ctg       8484
His Arg Asp Asn  Phe Ile Leu Phe Leu  Thr Ser Val Glu Pro  Leu
            2485                 2490                 2495

ttt cct cga ttt  ctc agt gag cta ttc  agt tcg tct ttt ttg  gga       8529
Phe Pro Arg Phe  Leu Ser Glu Leu Phe  Ser Ser Ser Phe Leu  Gly
            2500                 2505                 2510

atc ccc gag tca  atc att gga ttg ata  caa aac tcc cga acg  ata       8574
Ile Pro Glu Ser  Ile Ile Gly Leu Ile  Gln Asn Ser Arg Thr  Ile
            2515                 2520                 2525

aga agg cag ttt  aga aag agt ctc tca  aaa act tta gaa gaa  tcc       8619
Arg Arg Gln Phe  Arg Lys Ser Leu Ser  Lys Thr Leu Glu Glu  Ser
            2530                 2535                 2540

ttc tac aac tca  gag atc cac ggg att  agt cgg atg acc cag  aca       8664
Phe Tyr Asn Ser  Glu Ile His Gly Ile  Ser Arg Met Thr Gln  Thr
            2545                 2550                 2555
```

-continued

```
cct cag agg gtt  ggg ggg gtg tgg cct  tgc tct tca gag agg  gca      8709
Pro Gln Arg Val  Gly Gly Val Trp Pro  Cys Ser Ser Glu Arg  Ala
            2560                 2565                 2570

gat cta ctt agg  gag atc tct tgg gga  aga aaa gtg gta ggc  acg      8754
Asp Leu Leu Arg  Glu Ile Ser Trp Gly  Arg Lys Val Val Gly  Thr
            2575                 2580                 2585

aca gtt cct cac  cct tct gag atg ttg  ggg tta ctt ccc aag  tcc      8799
Thr Val Pro His  Pro Ser Glu Met Leu  Gly Leu Leu Pro Lys  Ser
            2590                 2595                 2600

tct att tct tgc  act tgt gga gca aca  gga gga ggc aat cct  aga      8844
Ser Ile Ser Cys  Thr Cys Gly Ala Thr  Gly Gly Gly Asn Pro  Arg
            2605                 2610                 2615

gtt tct gta tca  gta ctc ccg tcc ttt  gat cag tca ttt ttt  tca      8889
Val Ser Val Ser  Val Leu Pro Ser Phe  Asp Gln Ser Phe Phe  Ser
            2620                 2625                 2630

cga ggc ccc cta  aag ggg tac ttg ggc  tcg tcc acc tct atg  tcg      8934
Arg Gly Pro Leu  Lys Gly Tyr Leu Gly  Ser Ser Thr Ser Met  Ser
            2635                 2640                 2645

acc cag cta ttc  cat gca tgg gaa aaa  gtc act aat gtt cat  gtg      8979
Thr Gln Leu Phe  His Ala Trp Glu Lys  Val Thr Asn Val His  Val
            2650                 2655                 2660

gtg aag aga gct  cta tcg tta aaa gaa  tct ata aac tgg ttc  att      9024
Val Lys Arg Ala  Leu Ser Leu Lys Glu  Ser Ile Asn Trp Phe  Ile
            2665                 2670                 2675

act aga gat tcc  aac ttg gct caa gct  cta att agg aac att  atg      9069
Thr Arg Asp Ser  Asn Leu Ala Gln Ala  Leu Ile Arg Asn Ile  Met
            2680                 2685                 2690

tct ctg aca ggc  cct gat ttc cct cta  gag gag gcc cct gtc  ttc      9114
Ser Leu Thr Gly  Pro Asp Phe Pro Leu  Glu Glu Ala Pro Val  Phe
            2695                 2700                 2705

aaa agg acg ggg  tca gcc ttg cat agg  ttc aag tct gcc aga  tac      9159
Lys Arg Thr Gly  Ser Ala Leu His Arg  Phe Lys Ser Ala Arg  Tyr
            2710                 2715                 2720

agc gaa gga ggg  tat tct tct gtc tgc  ccg aac ctc ctc tct  cat      9204
Ser Glu Gly Gly  Tyr Ser Ser Val Cys  Pro Asn Leu Leu Ser  His
            2725                 2730                 2735

att tct gtt agt  aca gac acc atg tct  gat ttg acc caa gac  ggg      9249
Ile Ser Val Ser  Thr Asp Thr Met Ser  Asp Leu Thr Gln Asp  Gly
            2740                 2745                 2750

aag aac tac gat  ttc atg ttc cag cca  ttg atg ctt tat gca  cag      9294
Lys Asn Tyr Asp  Phe Met Phe Gln Pro  Leu Met Leu Tyr Ala  Gln
            2755                 2760                 2765

aca tgg aca tca  gag ctg gta cag aga  gac aca agg cta aga  gac      9339
Thr Trp Thr Ser  Glu Leu Val Gln Arg  Asp Thr Arg Leu Arg  Asp
            2770                 2775                 2780

tct acg ttt cat  tgg cac ctc cga tgc  aac agg tgt gtg aga  ccc      9384
Ser Thr Phe His  Trp His Leu Arg Cys  Asn Arg Cys Val Arg  Pro
            2785                 2790                 2795

att gac gac gtg  acc ctg gag acc tct  cag atc ttc gag ttt  ccg      9429
Ile Asp Asp Val  Thr Leu Glu Thr Ser  Gln Ile Phe Glu Phe  Pro
            2800                 2805                 2810

gat gtg tcg aaa  aga ata tcc aga atg  gtt tct ggg gct gtg  cct      9474
Asp Val Ser Lys  Arg Ile Ser Arg Met  Val Ser Gly Ala Val  Pro
            2815                 2820                 2825

cac ttc cag agg  ctt ccc gat atc cgt  ctg aga cca gga gat  ttt      9519
His Phe Gln Arg  Leu Pro Asp Ile Arg  Leu Arg Pro Gly Asp  Phe
            2830                 2835                 2840

gaa tct cta agc  ggt aga gaa aag tct  cac cat atc gga tca  gct      9564
Glu Ser Leu Ser  Gly Arg Glu Lys Ser  His His Ile Gly Ser  Ala
            2845                 2850                 2855
```

-continued

```
cag ggg ctc tta  tac tca atc tta gtg  gca att cac gac tca  gga      9609
Gln Gly Leu Leu  Tyr Ser Ile Leu Val  Ala Ile His Asp Ser  Gly
            2860                 2865                 2870

tac aat gat gga  acc atc ttc cct gcc  aac ata tac ggc aag  gtt      9654
Tyr Asn Asp Gly  Thr Ile Phe Pro Ala  Asn Ile Tyr Gly Lys  Val
            2875                 2880                 2885

tcc cct aga gac  tat ttg aga ggg ctc  gca agg gga gta ttg  ata      9699
Ser Pro Arg Asp  Tyr Leu Arg Gly Leu  Ala Arg Gly Val Leu  Ile
            2890                 2895                 2900

gga tcc tcg att  tgc ttc ttg aca aga  atg aca aat atc aat  att      9744
Gly Ser Ser Ile  Cys Phe Leu Thr Arg  Met Thr Asn Ile Asn  Ile
            2905                 2910                 2915

aat aga cct ctt  gaa ttg atc tca ggg  gta atc tca tat att  ctc      9789
Asn Arg Pro Leu  Glu Leu Ile Ser Gly  Val Ile Ser Tyr Ile  Leu
            2920                 2925                 2930

ctg agg cta gat  aac cat ccc tcc ttg  tac ata atg ctc aga  gaa      9834
Leu Arg Leu Asp  Asn His Pro Ser Leu  Tyr Ile Met Leu Arg  Glu
            2935                 2940                 2945

ccg tct ctt aga  gga gag ata ttt tct  atc cct cag aaa atc  ccc      9879
Pro Ser Leu Arg  Gly Glu Ile Phe Ser  Ile Pro Gln Lys Ile  Pro
            2950                 2955                 2960

gcc gct tat cca  acc act atg aaa gaa  ggc aac aga tca atc  ttg      9924
Ala Ala Tyr Pro  Thr Thr Met Lys Glu  Gly Asn Arg Ser Ile  Leu
            2965                 2970                 2975

tgt tat ctc caa  cat gtg cta cgc tat  gag cga gag ata atc  acg      9969
Cys Tyr Leu Gln  His Val Leu Arg Tyr  Glu Arg Glu Ile Ile  Thr
            2980                 2985                 2990

gcg tct cca gag  aat gac tgg cta tgg  atc ttt tca gac ttt  aga     10014
Ala Ser Pro Glu  Asn Asp Trp Leu Trp  Ile Phe Ser Asp Phe  Arg
            2995                 3000                 3005

agt gcc aaa atg  acg tac cta acc ctc  att act tac cag tct  cat     10059
Ser Ala Lys Met  Thr Tyr Leu Thr Leu  Ile Thr Tyr Gln Ser  His
            3010                 3015                 3020

ctt cta ctc cag  agg gtt gag aga aac  cta tct aag agt atg  aga     10104
Leu Leu Leu Gln  Arg Val Glu Arg Asn  Leu Ser Lys Ser Met  Arg
            3025                 3030                 3035

gat aac ctg cga  caa ttg agt tcc ttg  atg agg cag gtg ctg  ggc     10149
Asp Asn Leu Arg  Gln Leu Ser Ser Leu  Met Arg Gln Val Leu  Gly
            3040                 3045                 3050

ggg cac gga gaa  gat acc tta gag tca  gac gac aac att caa  cga     10194
Gly His Gly Glu  Asp Thr Leu Glu Ser  Asp Asp Asn Ile Gln  Arg
            3055                 3060                 3065

ctg cta aaa gac  tct tta cga agg aca  aga tgg gtg gat caa  gag     10239
Leu Leu Lys Asp  Ser Leu Arg Arg Thr  Arg Trp Val Asp Gln  Glu
            3070                 3075                 3080

gtg cgc cat gca  gct aga acc atg act  gga gat tac agc ccc  aac     10284
Val Arg His Ala  Ala Arg Thr Met Thr  Gly Asp Tyr Ser Pro  Asn
            3085                 3090                 3095

aag aag gtg tcc  cgt aag gta gga tgt  tca gaa tgg gtc tgc  tct     10329
Lys Lys Val Ser  Arg Lys Val Gly Cys  Ser Glu Trp Val Cys  Ser
            3100                 3105                 3110

gct caa cag gtt  gca gtc tct acc tca  gca aac ccg gcc cct  gtc     10374
Ala Gln Gln Val  Ala Val Ser Thr Ser  Ala Asn Pro Ala Pro  Val
            3115                 3120                 3125

tcg gag ctt gac  ata agg gcc ctc tct  aag agg ttc cag aac  cct     10419
Ser Glu Leu Asp  Ile Arg Ala Leu Ser  Lys Arg Phe Gln Asn  Pro
            3130                 3135                 3140

ttg atc tcg ggc  ttg aga gtg gtt cag  tgg gca acc ggt gct  cat     10464
Leu Ile Ser Gly  Leu Arg Val Val Gln  Trp Ala Thr Gly Ala  His
            3145                 3150                 3155
```

-continued

```
tat aag ctt aag  cct att cta gat gat  ctc aat gtt ttc ccc  tct     10509
Tyr Lys Leu Lys  Pro Ile Leu Asp Asp  Leu Asn Val Phe Pro  Ser
            3160                 3165                 3170

ctc tgc ctt gta  gtt ggg gac ggg tca  ggg ggg ata tca agg  gca     10554
Leu Cys Leu Val  Val Gly Asp Gly Ser  Gly Gly Ile Ser Arg  Ala
            3175                 3180                 3185

gtc ctc aac atg  ttt cca gat gcc aag  ctt gtg ttc aac agt  ctc     10599
Val Leu Asn Met  Phe Pro Asp Ala Lys  Leu Val Phe Asn Ser  Leu
            3190                 3195                 3200

tta gag gtg aat  gac ctg atg gct tcc  gga aca cat cca ctg  cct     10644
Leu Glu Val Asn  Asp Leu Met Ala Ser  Gly Thr His Pro Leu  Pro
            3205                 3210                 3215

cct tca gca atc  atg agg gga gga aat  ggt atc gtc tcc aga  gtg     10689
Pro Ser Ala Ile  Met Arg Gly Gly Asn  Gly Ile Val Ser Arg  Val
            3220                 3225                 3230

ata gat ttt gac  tca atc tgg gaa aaa  ccg tcc gac ttg aga  aac     10734
Ile Asp Phe Asp  Ser Ile Trp Glu Lys  Pro Ser Asp Leu Arg  Asn
            3235                 3240                 3245

ttg gca acc tgg  aaa tac ttc cag tca  gtc caa aag cag gtc  aac     10779
Leu Ala Thr Trp  Lys Tyr Phe Gln Ser  Val Gln Lys Gln Val  Asn
            3250                 3255                 3260

atg tcc tat gac  ctc att att tgc gat  gca gaa gtt act gac  att     10824
Met Ser Tyr Asp  Leu Ile Ile Cys Asp  Ala Glu Val Thr Asp  Ile
            3265                 3270                 3275

gca tct atc aac  cgg ata acc ctg tta  atg tcc gat ttt gca  ttg     10869
Ala Ser Ile Asn  Arg Ile Thr Leu Leu  Met Ser Asp Phe Ala  Leu
            3280                 3285                 3290

tct ata gat gga  cca ctc tat ttg gtc  ttc aaa act tat ggg  act     10914
Ser Ile Asp Gly  Pro Leu Tyr Leu Val  Phe Lys Thr Tyr Gly  Thr
            3295                 3300                 3305

atg cta gta aat  cca aac tac aag gct  att caa cac ctg tca  aga     10959
Met Leu Val Asn  Pro Asn Tyr Lys Ala  Ile Gln His Leu Ser  Arg
            3310                 3315                 3320

gcg ttc ccc tcg  gtc aca ggg ttt atc  acc caa gta act tcg  tct     11004
Ala Phe Pro Ser  Val Thr Gly Phe Ile  Thr Gln Val Thr Ser  Ser
            3325                 3330                 3335

ttt tca tct gag  ctc tac ctc cga ttc  tcc aaa cga ggg aag  ctt     11049
Phe Ser Ser Glu  Leu Tyr Leu Arg Phe  Ser Lys Arg Gly Lys  Leu
            3340                 3345                 3350

ttc aga gat gct  gag tac ttg acc tct  tcc acc ctt cga gaa  atg     11094
Phe Arg Asp Ala  Glu Tyr Leu Thr Ser  Ser Thr Leu Arg Glu  Met
            3355                 3360                 3365

agc ctt gtg tta  ttc aat tgt agc agc  ccc aag agt gag atg  cag     11139
Ser Leu Val Leu  Phe Asn Cys Ser Ser  Pro Lys Ser Glu Met  Gln
            3370                 3375                 3380

aga gct cgt tcc  ttg aac tat cag gat  ctt gtg aga gga ttt  cct     11184
Arg Ala Arg Ser  Leu Asn Tyr Gln Asp  Leu Val Arg Gly Phe  Pro
            3385                 3390                 3395

gaa gaa atc ata  tca aat cct tac aat  gag atg atc ata act  ctg     11229
Glu Glu Ile Ile  Ser Asn Pro Tyr Asn  Glu Met Ile Ile Thr  Leu
            3400                 3405                 3410

att gac agt gat  gta gaa tct ttt cta  gtc cac aag atg gtt  gat     11274
Ile Asp Ser Asp  Val Glu Ser Phe Leu  Val His Lys Met Val  Asp
            3415                 3420                 3425

gat ctt gag tta  cag agg gga act ctg  tct aaa gtg gct atc  att     11319
Asp Leu Glu Leu  Gln Arg Gly Thr Leu  Ser Lys Val Ala Ile  Ile
            3430                 3435                 3440

ata gcc atc atg  ata gtt ttc tcc aac  aga gtc ttc aac gtt  tcc     11364
Ile Ala Ile Met  Ile Val Phe Ser Asn  Arg Val Phe Asn Val  Ser
            3445                 3450                 3455
```

```
aaa ccc cta act  gac ccc ttg ttc tat  cca ccg tct gat ccc  aaa      11409
Lys Pro Leu Thr  Asp Pro Leu Phe Tyr  Pro Pro Ser Asp Pro  Lys
            3460                 3465                 3470

atc ctg agg cac  ttc aac ata tgt cgc  agt act atg atg tat  cta      11454
Ile Leu Arg His  Phe Asn Ile Cys Arg  Ser Thr Met Met Tyr  Leu
            3475                 3480                 3485

tct act gct tta  ggt gac gtc cct agc  ttc gca aga ctt cac  gac      11499
Ser Thr Ala Leu  Gly Asp Val Pro Ser  Phe Ala Arg Leu His  Asp
            3490                 3495                 3500

ctg tat aac aga  cct ata act tat tac  ttc aga aag caa ttc  att      11544
Leu Tyr Asn Arg  Pro Ile Thr Tyr Tyr  Phe Arg Lys Gln Phe  Ile
            3505                 3510                 3515

cga ggg aac gtt  tat cta tct tgg agt  tgg tcc aac gac acc  tca      11589
Arg Gly Asn Val  Tyr Leu Ser Trp Ser  Trp Ser Asn Asp Thr  Ser
            3520                 3525                 3530

gtg ttc aaa agg  gta gcc tgt aat tct  agc ctg agt ctg tca  tct      11634
Val Phe Lys Arg  Val Ala Cys Asn Ser  Ser Leu Ser Leu Ser  Ser
            3535                 3540                 3545

cac tgg atc agg  ttg att tac aag ata  gtg aag gct acc aga  ctc      11679
His Trp Ile Arg  Leu Ile Tyr Lys Ile  Val Lys Ala Thr Arg  Leu
            3550                 3555                 3560

gtt ggc agc atc  aag gat cta tcc aga  gaa gtg gaa aga cac  ctt      11724
Val Gly Ser Ile  Lys Asp Leu Ser Arg  Glu Val Glu Arg His  Leu
            3565                 3570                 3575

cat agg tac aac  agg tgg atc acc cta  gag gat atc aga tct  aga      11769
His Arg Tyr Asn  Arg Trp Ile Thr Leu  Glu Asp Ile Arg Ser  Arg
            3580                 3585                 3590

tca tcc cta cta  gac tac agt tgc ctg  tgaaccggat actcctggaa         11816
Ser Ser Leu Leu  Asp Tyr Ser Cys Leu
            3595                 3600

gcctgcccat gctaagactc ttgtgtgatg tatcttgaaa aaaacaagat cctaaatctg  11876

aacctttggt tgtttgattg tttttctcat ttttgttgtt tatttgttaa gcgt         11930


<210> SEQ ID NO 2
<211> LENGTH: 450
<212> TYPE: PRT
<213> ORGANISM: Artificial Sequence
<220> FEATURE:
<223> OTHER INFORMATION: Synthetic Construct

<400> SEQUENCE: 2

Met Asp Ala Asp Lys Ile Val Phe Lys Val Asn Asn Gln Val Val Ser
1               5                   10                  15

Leu Lys Pro Glu Ile Ile Val Asp Gln His Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asp Pro Asp Asp Val Cys Ser Tyr Leu Ala Ala Ala Met Gln Phe
65                  70                  75                  80

Phe Glu Gly Thr Cys Pro Glu Asp Trp Thr Ser Tyr Gly Ile Val Ile
85                  90                  95

Ala Arg Lys Gly Asp Lys Ile Thr Pro Gly Ser Leu Val Glu Ile Lys
100                 105                 110

Arg Thr Asp Val Glu Gly Asn Trp Ala Leu Thr Gly Gly Met Glu Leu
115                 120                 125

Thr Arg Asp Pro Thr Val Pro Glu His Ala Ser Leu Val Gly Leu Leu
130                 135                 140
```

```
Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
165                 170                 175

Pro Phe Val Lys Ile Val Glu His His Thr Leu Met Thr Thr His Lys
180                 185                 190

Met Cys Ala Asn Trp Ser Thr Ile Pro Asn Phe Arg Phe Leu Ala Gly
195                 200                 205

Thr Tyr Asp Met Phe Phe Ser Arg Ile Glu His Leu Tyr Ser Ala Ile
210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
245                 250                 255

Ile Leu Tyr Phe Phe His Lys Asn Phe Glu Glu Glu Ile Arg Arg Met
260                 265                 270

Phe Glu Pro Gly Gln Glu Thr Ala Val Pro His Ser Tyr Phe Ile His
275                 280                 285

Phe Arg Ser Leu Gly Leu Ser Gly Lys Ser Pro Tyr Ser Ser Asn Ala
290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
325                 330                 335

Glu Met Ser Val Leu Gly Gly Tyr Leu Gly Glu Glu Phe Phe Gly Lys
340                 345                 350

Gly Thr Phe Glu Arg Arg Phe Phe Arg Asp Glu Lys Glu Leu Gln Glu
355                 360                 365

Tyr Glu Ala Ala Glu Leu Thr Lys Thr Asp Val Ala Leu Ala Asp Asp
370                 375                 380

Gly Thr Val Asn Ser Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
405                 410                 415

Lys Arg Ser His Ile Arg Arg Tyr Val Ser Val Ser Ser Asn His Gln
420                 425                 430

Ala Arg Pro Asn Ser Phe Ala Glu Phe Leu Asn Lys Thr Tyr Ser Ser
435                 440                 445

Asp Ser
450


<210> SEQ ID NO 3
<211> LENGTH: 297
<212> TYPE: PRT
<213> ORGANISM: Artificial Sequence
<220> FEATURE:
<223> OTHER INFORMATION: Synthetic Construct

<400> SEQUENCE: 3

Met Ser Lys Ile Phe Val Asn Pro Ser Ala Ile Arg Ala Gly Leu Ala
1               5                   10                  15

Asp Leu Glu Met Ala Glu Glu Thr Val Asp Leu Ile Asn Arg Asn Ile
            20                  25                  30

Glu Asp Asn Gln Ala His Leu Gln Gly Glu Pro Ile Glu Val Asp Asn
        35                  40                  45
```

Leu Pro Glu Asp Met Gly Arg Leu His Leu Asp Asp Gly Lys Ser Pro
50 55 60

Asn Pro Gly Glu Met Ala Lys Val Gly Glu Gly Lys Tyr Arg Glu Asp
65 70 75 80

Phe Gln Met Asp Glu Gly Glu Asp Leu Ser Phe Leu Phe Gln Ser Tyr
85 90 95

Leu Glu Asn Val Gly Val Gln Ile Val Arg Gln Met Arg Ser Gly Glu
100 105 110

Arg Phe Leu Lys Ile Trp Ser Gln Thr Val Glu Glu Ile Ile Ser Tyr
115 120 125

Val Ala Val Asn Phe Pro Asn Pro Pro Gly Lys Ser Ser Glu Asp Lys
130 135 140

Ser Thr Gln Thr Thr Gly Arg Glu Leu Lys Lys Glu Thr Thr Pro Thr
145 150 155 160

Pro Ser Gln Arg Glu Ser Gln Ser Ser Lys Ala Arg Met Ala Ala Gln
165 170 175

Ile Ala Ser Gly Pro Pro Ala Leu Glu Trp Ser Ala Thr Asn Glu Glu
180 185 190

Asp Asp Leu Ser Val Glu Ala Glu Ile Ala His Gln Ile Ala Glu Ser
195 200 205

Phe Ser Lys Lys Tyr Lys Phe Pro Ser Arg Ser Ser Gly Ile Leu Leu
210 215 220

Tyr Asn Phe Glu Gln Leu Lys Met Asn Leu Asp Asp Ile Val Lys Glu
225 230 235 240

Ala Lys Asn Val Pro Gly Val Thr Arg Leu Ala His Asp Gly Ser Lys
245 250 255

Leu Pro Leu Arg Cys Val Leu Gly Trp Val Ala Leu Ala Asn Pro Lys
260 265 270

Lys Phe Gln Leu Leu Val Glu Ser Asp Lys Leu Ser Lys Ile Met Gln
275 280 285

Asp Asp Leu Asn Arg Tyr Thr Ser Cys
290 295

<210> SEQ ID NO 4
<211> LENGTH: 202
<212> TYPE: PRT
<213> ORGANISM: Artificial Sequence
<220> FEATURE:
<223> OTHER INFORMATION: Synthetic Construct

<400> SEQUENCE: 4

Met Asn Phe Leu Arg Lys Ile Val Lys Asn Cys Arg Asp Glu Asp Thr
1 5 10 15

Gln Lys Pro Ser Pro Val Ser Ala Pro Leu Asp Asp Asp Asp Leu Trp
20 25 30

Leu Pro Pro Pro Glu Tyr Val Pro Leu Lys Glu Leu Thr Ser Lys Lys
35 40 45

Asn Met Arg Asn Phe Cys Ile Asn Gly Gly Val Lys Val Cys Ser Pro
50 55 60

Asn Gly Tyr Ser Phe Arg Ile Leu Arg His Ile Leu Lys Ser Phe Asp
65 70 75 80

Glu Ile Tyr Ser Gly Asn His Arg Met Ile Gly Leu Ala Lys Val Val
85 90 95

Ile Gly Leu Ala Leu Ser Gly Ser Pro Val Pro Glu Gly Met Asn Trp
100 105 110

Val Tyr Lys Leu Arg Arg Thr Phe Ile Phe Gln Trp Ala Asp Ser Arg

```
        115                 120                 125

Gly Pro Leu Glu Gly Glu Glu Leu Glu Tyr Ser Gln Glu Ile Thr Trp
    130                 135                 140

Asp Asp Asp Thr Glu Phe Val Gly Leu Gln Ile Arg Val Ile Ala Lys
145                 150                 155                 160

Gln Cys His Ile Gln Gly Arg Ile Trp Cys Ile Asn Met Asn Pro Arg
                165                 170                 175

Ala Cys Gln Leu Trp Ser Asp Met Ser Leu Gln Thr Gln Arg Ser Glu
            180                 185                 190

Glu Asp Lys Asp Ser Ser Leu Leu Leu Glu
        195                 200


<210> SEQ ID NO 5
<211> LENGTH: 524
<212> TYPE: PRT
<213> ORGANISM: Artificial Sequence
<220> FEATURE:
<221> NAME/KEY: misc_feature
<222> LOCATION: (352)..(352)
<223> OTHER INFORMATION: The 'Xaa' at location 352 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 5

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255
```

```
Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Pro
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Xaa
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520


<210> SEQ ID NO 6
<211> LENGTH: 2127
<212> TYPE: PRT
<213> ORGANISM: Artificial Sequence
<220> FEATURE:
<223> OTHER INFORMATION: Synthetic Construct

<400> SEQUENCE: 6

Met Leu Asp Pro Gly Glu Val Tyr Asp Asp Pro Ile Asp Pro Ile Glu
1               5                   10                  15

Leu Glu Asp Glu Pro Arg Gly Thr Pro Thr Val Pro Asn Ile Leu Arg
            20                  25                  30

Asn Ser Asp Tyr Asn Leu Asn Ser Pro Leu Ile Glu Asp Pro Ala Arg
        35                  40                  45

Leu Met Leu Glu Trp Leu Lys Thr Gly Asn Arg Pro Tyr Arg Met Thr
    50                  55                  60

Leu Thr Asp Asn Cys Ser Arg Ser Phe Arg Val Leu Lys Asp Tyr Phe
65                  70                  75                  80

Lys Lys Val Asp Leu Gly Ser Leu Lys Val Gly Gly Met Ala Ala Gln
                85                  90                  95
```

-continued

```
Ser Met Ile Ser Leu Trp Leu Tyr Gly Ala His Ser Glu Ser Asn Arg
            100                 105                 110

Ser Arg Arg Cys Ile Thr Asp Leu Ala His Phe Tyr Ser Lys Ser Ser
        115                 120                 125

Pro Ile Glu Lys Leu Leu Asn Leu Thr Leu Gly Asn Arg Gly Leu Arg
    130                 135                 140

Ile Pro Pro Glu Gly Val Leu Ser Cys Leu Glu Arg Val Asp Tyr Asp
145                 150                 155                 160

Asn Ala Phe Gly Arg Tyr Leu Ala Asn Thr Tyr Ser Ser Tyr Leu Phe
                165                 170                 175

Phe His Val Ile Thr Leu Tyr Met Asn Ala Leu Asp Trp Asp Glu Glu
            180                 185                 190

Lys Thr Ile Leu Ala Leu Trp Lys Asp Leu Thr Ser Val Asp Ile Gly
        195                 200                 205

Lys Asp Leu Val Lys Phe Lys Asp Gln Ile Trp Gly Leu Pro Ile Val
    210                 215                 220

Thr Lys Asp Phe Val Tyr Ser Gln Ser Ser Asn Cys Leu Phe Asp Arg
225                 230                 235                 240

Asn Tyr Thr Leu Met Leu Lys Glu Leu Phe Leu Ser Arg Phe Asn Ser
                245                 250                 255

Leu Met Val Leu Leu Ser Pro Pro Glu Pro Arg Tyr Ser Asp Asp Leu
            260                 265                 270

Ile Ser Gln Leu Cys Gln Leu Tyr Ile Ala Gly Asp Gln Val Leu Ser
        275                 280                 285

Met Cys Gly Asn Ser Gly Tyr Glu Val Ile Lys Ile Leu Glu Pro Tyr
    290                 295                 300

Val Val Asn Ser Leu Val Gln Arg Ala Glu Lys Phe Arg Pro Leu Ile
305                 310                 315                 320

His Ser Leu Gly Asp Phe Pro Val Phe Ile Lys Asp Lys Val Ser Gln
                325                 330                 335

Leu Glu Glu Thr Phe Gly Pro Cys Ala Arg Arg Phe Phe Arg Ala Leu
            340                 345                 350

Asp Gln Phe Asp Asn Ile His Asp Leu Val Phe Val Tyr Gly Cys Tyr
        355                 360                 365

Arg His Trp Gly His Pro Tyr Ile Asp Tyr Arg Lys Gly Leu Ser Lys
    370                 375                 380

Leu Tyr Asp Gln Val His Ile Lys Lys Val Ile Asp Lys Ser Tyr Gln
385                 390                 395                 400

Glu Cys Leu Ala Ser Asp Leu Ala Arg Arg Ile Leu Arg Trp Gly Phe
                405                 410                 415

Asp Lys Tyr Ser Lys Trp Tyr Leu Asp Ser Arg Phe Leu Ala Arg Asp
            420                 425                 430

His Pro Leu Thr Pro Tyr Ile Lys Thr Gln Thr Trp Pro Pro Lys His
        435                 440                 445

Ile Val Asp Leu Val Gly Asp Thr Trp His Lys Leu Pro Ile Thr Gln
    450                 455                 460

Ile Phe Glu Ile Pro Glu Ser Met Asp Pro Ser Glu Ile Leu Asp Asp
465                 470                 475                 480

Lys Ser His Ser Phe Thr Arg Thr Arg Leu Ala Ser Trp Leu Ser Glu
                485                 490                 495

Asn Arg Gly Gly Pro Val Pro Ser Glu Lys Val Ile Ile Thr Ala Leu
            500                 505                 510

Ser Lys Pro Pro Val Asn Pro Arg Glu Phe Leu Arg Ser Ile Asp Leu
        515                 520                 525
```

-continued

```
Gly Gly Leu Pro Asp Glu Asp Leu Ile Ile Gly Leu Lys Pro Lys Glu
    530                 535                 540

Arg Glu Leu Lys Ile Glu Gly Arg Phe Phe Ala Leu Met Ser Trp Asn
545                 550                 555                 560

Leu Arg Leu Tyr Phe Val Ile Thr Glu Lys Leu Leu Ala Asn Tyr Ile
                565                 570                 575

Leu Pro Leu Phe Asp Ala Leu Thr Met Thr Asp Asn Leu Asn Lys Val
            580                 585                 590

Phe Lys Lys Leu Ile Asp Arg Val Thr Gly Gln Gly Leu Leu Asp Tyr
        595                 600                 605

Ser Arg Val Thr Tyr Ala Phe His Leu Asp Tyr Glu Lys Trp Asn Asn
    610                 615                 620

His Gln Arg Leu Glu Ser Thr Glu Asp Val Phe Ser Val Leu Asp Gln
625                 630                 635                 640

Val Phe Gly Leu Lys Arg Val Phe Ser Arg Thr His Glu Phe Phe Gln
                645                 650                 655

Lys Ala Trp Ile Tyr Tyr Ser Asp Arg Ser Asp Leu Ile Gly Leu Arg
            660                 665                 670

Glu Asp Gln Ile Tyr Cys Leu Asp Ala Ser Asn Gly Pro Thr Cys Trp
        675                 680                 685

Asn Gly Gln Asp Gly Gly Leu Glu Gly Leu Arg Gln Lys Gly Trp Ser
    690                 695                 700

Leu Val Ser Leu Leu Met Ile Asp Arg Glu Ser Gln Ile Arg Asn Thr
705                 710                 715                 720

Arg Thr Lys Ile Leu Ala Gln Gly Asp Asn Gln Val Leu Cys Pro Thr
                725                 730                 735

Tyr Met Leu Ser Pro Gly Leu Ser Gln Glu Gly Leu Leu Tyr Glu Leu
            740                 745                 750

Glu Arg Ile Ser Arg Asn Ala Leu Ser Ile Tyr Arg Ala Val Glu Glu
        755                 760                 765

Gly Ala Ser Lys Leu Gly Leu Ile Thr Lys Lys Glu Glu Thr Met Cys
    770                 775                 780

Ser Tyr Asp Phe Leu Ile Tyr Gly Lys Thr Pro Leu Phe Arg Gly Asn
785                 790                 795                 800

Ile Leu Val Pro Glu Ser Lys Arg Trp Ala Arg Val Ser Cys Val Ser
                805                 810                 815

Asn Asp Gln Ile Val Asn Leu Ala Asn Ile Met Ser Thr Val Ser Thr
            820                 825                 830

Asn Ala Leu Thr Val Ala Gln His Ser Gln Ser Leu Ile Lys Pro Met
        835                 840                 845

Gly Asp Phe Leu Leu Met Ser Val Gln Ala Val Phe His Tyr Leu Leu
    850                 855                 860

Phe Ser Pro Ile Leu Lys Gly Arg Val Tyr Lys Ile Leu Ser Ala Glu
865                 870                 875                 880

Gly Asp Ser Phe Leu Leu Ala Met Ser Arg Ile Ile Tyr Leu Asp Pro
                885                 890                 895

Ser Leu Gly Gly Val Ser Gly Met Ser Leu Gly Arg Phe His Ile Arg
            900                 905                 910

Gln Phe Ser Asp Pro Val Ser Glu Gly Leu Ser Phe Trp Arg Glu Ile
        915                 920                 925

Trp Leu Ser Ser His Glu Ser Trp Val His Ala Leu Cys Gln Glu Ala
    930                 935                 940

Gly Asn Pro Asp Leu Gly Glu Arg Thr Leu Glu Ser Phe Thr Arg Leu
```

-continued

```
945                 950                 955                 960

Leu Glu Asp Pro Thr Thr Leu Asn Ile Arg Gly Gly Ala Ser Pro Thr
                965                 970                 975

Ile Leu Leu Lys Asp Ala Ile Arg Lys Ala Leu Tyr Asp Glu Val Asp
            980                 985                 990

Lys Val Glu Asn Ser Glu Phe Arg  Glu Ala Ile Leu Leu  Ser Lys Thr
        995                 1000                1005

His Arg  Asp Asn Phe Ile Leu  Phe Leu Thr Ser Val  Glu Pro Leu
    1010                1015                1020

Phe Pro  Arg Phe Leu Ser Glu  Leu Phe Ser Ser Ser  Phe Leu Gly
    1025                1030                1035

Ile Pro  Glu Ser Ile Ile Gly  Leu Ile Gln Asn Ser  Arg Thr Ile
    1040                1045                1050

Arg Arg  Gln Phe Arg Lys Ser  Leu Ser Lys Thr Leu  Glu Glu Ser
    1055                1060                1065

Phe Tyr  Asn Ser Glu Ile His  Gly Ile Ser Arg Met  Thr Gln Thr
    1070                1075                1080

Pro Gln  Arg Val Gly Gly Val  Trp Pro Cys Ser Ser  Glu Arg Ala
    1085                1090                1095

Asp Leu  Leu Arg Glu Ile Ser  Trp Gly Arg Lys Val  Val Gly Thr
    1100                1105                1110

Thr Val  Pro His Pro Ser Glu  Met Leu Gly Leu Leu  Pro Lys Ser
    1115                1120                1125

Ser Ile  Ser Cys Thr Cys Gly  Ala Thr Gly Gly Gly  Asn Pro Arg
    1130                1135                1140

Val Ser  Val Ser Val Leu Pro  Ser Phe Asp Gln Ser  Phe Phe Ser
    1145                1150                1155

Arg Gly  Pro Leu Lys Gly Tyr  Leu Gly Ser Ser Thr  Ser Met Ser
    1160                1165                1170

Thr Gln  Leu Phe His Ala Trp  Glu Lys Val Thr Asn  Val His Val
    1175                1180                1185

Val Lys  Arg Ala Leu Ser Leu  Lys Glu Ser Ile Asn  Trp Phe Ile
    1190                1195                1200

Thr Arg  Asp Ser Asn Leu Ala  Gln Ala Leu Ile Arg  Asn Ile Met
    1205                1210                1215

Ser Leu  Thr Gly Pro Asp Phe  Pro Leu Glu Glu Ala  Pro Val Phe
    1220                1225                1230

Lys Arg  Thr Gly Ser Ala Leu  His Arg Phe Lys Ser  Ala Arg Tyr
    1235                1240                1245

Ser Glu  Gly Gly Tyr Ser Ser  Val Cys Pro Asn Leu  Leu Ser His
    1250                1255                1260

Ile Ser  Val Ser Thr Asp Thr  Met Ser Asp Leu Thr  Gln Asp Gly
    1265                1270                1275

Lys Asn  Tyr Asp Phe Met Phe  Gln Pro Leu Met Leu  Tyr Ala Gln
    1280                1285                1290

Thr Trp  Thr Ser Glu Leu Val  Gln Arg Asp Thr Arg  Leu Arg Asp
    1295                1300                1305

Ser Thr  Phe His Trp His Leu  Arg Cys Asn Arg Cys  Val Arg Pro
    1310                1315                1320

Ile Asp  Asp Val Thr Leu Glu  Thr Ser Gln Ile Phe  Glu Phe Pro
    1325                1330                1335

Asp Val  Ser Lys Arg Ile Ser  Arg Met Val Ser Gly  Ala Val Pro
    1340                1345                1350
```

-continued

```
His Phe  Gln Arg Leu Pro Asp  Ile Arg Leu Arg Pro  Gly Asp Phe
    1355                 1360                 1365

Glu Ser  Leu Ser Gly Arg Glu  Lys Ser His His Ile  Gly Ser Ala
    1370                 1375                 1380

Gln Gly  Leu Leu Tyr Ser Ile  Leu Val Ala Ile His  Asp Ser Gly
    1385                 1390                 1395

Tyr Asn  Asp Gly Thr Ile Phe  Pro Ala Asn Ile Tyr  Gly Lys Val
    1400                 1405                 1410

Ser Pro  Arg Asp Tyr Leu Arg  Gly Leu Ala Arg Gly  Val Leu Ile
    1415                 1420                 1425

Gly Ser  Ser Ile Cys Phe Leu  Thr Arg Met Thr Asn  Ile Asn Ile
    1430                 1435                 1440

Asn Arg  Pro Leu Glu Leu Ile  Ser Gly Val Ile Ser  Tyr Ile Leu
    1445                 1450                 1455

Leu Arg  Leu Asp Asn His Pro  Ser Leu Tyr Ile Met  Leu Arg Glu
    1460                 1465                 1470

Pro Ser  Leu Arg Gly Glu Ile  Phe Ser Ile Pro Gln  Lys Ile Pro
    1475                 1480                 1485

Ala Ala  Tyr Pro Thr Thr Met  Lys Glu Gly Asn Arg  Ser Ile Leu
    1490                 1495                 1500

Cys Tyr  Leu Gln His Val Leu  Arg Tyr Glu Arg Glu  Ile Ile Thr
    1505                 1510                 1515

Ala Ser  Pro Glu Asn Asp Trp  Leu Trp Ile Phe Ser  Asp Phe Arg
    1520                 1525                 1530

Ser Ala  Lys Met Thr Tyr Leu  Thr Leu Ile Thr Tyr  Gln Ser His
    1535                 1540                 1545

Leu Leu  Leu Gln Arg Val Glu  Arg Asn Leu Ser Lys  Ser Met Arg
    1550                 1555                 1560

Asp Asn  Leu Arg Gln Leu Ser  Ser Leu Met Arg Gln  Val Leu Gly
    1565                 1570                 1575

Gly His  Gly Glu Asp Thr Leu  Glu Ser Asp Asp Asn  Ile Gln Arg
    1580                 1585                 1590

Leu Leu  Lys Asp Ser Leu Arg  Arg Thr Arg Trp Val  Asp Gln Glu
    1595                 1600                 1605

Val Arg  His Ala Ala Arg Thr  Met Thr Gly Asp Tyr  Ser Pro Asn
    1610                 1615                 1620

Lys Lys  Val Ser Arg Lys Val  Gly Cys Ser Glu Trp  Val Cys Ser
    1625                 1630                 1635

Ala Gln  Gln Val Ala Val Ser  Thr Ser Ala Asn Pro  Ala Pro Val
    1640                 1645                 1650

Ser Glu  Leu Asp Ile Arg Ala  Leu Ser Lys Arg Phe  Gln Asn Pro
    1655                 1660                 1665

Leu Ile  Ser Gly Leu Arg Val  Val Gln Trp Ala Thr  Gly Ala His
    1670                 1675                 1680

Tyr Lys  Leu Lys Pro Ile Leu  Asp Asp Leu Asn Val  Phe Pro Ser
    1685                 1690                 1695

Leu Cys  Leu Val Val Gly Asp  Gly Ser Gly Gly Ile  Ser Arg Ala
    1700                 1705                 1710

Val Leu  Asn Met Phe Pro Asp  Ala Lys Leu Val Phe  Asn Ser Leu
    1715                 1720                 1725

Leu Glu  Val Asn Asp Leu Met  Ala Ser Gly Thr His  Pro Leu Pro
    1730                 1735                 1740

Pro Ser  Ala Ile Met Arg Gly  Gly Asn Gly Ile Val  Ser Arg Val
    1745                 1750                 1755
```

```
Ile Asp  Phe Asp Ser Ile Trp  Glu Lys Pro Ser Asp  Leu Arg Asn
    1760                 1765                 1770

Leu Ala  Thr Trp Lys Tyr Phe  Gln Ser Val Gln Lys  Gln Val Asn
    1775                 1780                 1785

Met Ser  Tyr Asp Leu Ile Ile  Cys Asp Ala Glu Val  Thr Asp Ile
    1790                 1795                 1800

Ala Ser  Ile Asn Arg Ile Thr  Leu Leu Met Ser Asp  Phe Ala Leu
    1805                 1810                 1815

Ser Ile  Asp Gly Pro Leu Tyr  Leu Val Phe Lys Thr  Tyr Gly Thr
    1820                 1825                 1830

Met Leu  Val Asn Pro Asn Tyr  Lys Ala Ile Gln His  Leu Ser Arg
    1835                 1840                 1845

Ala Phe  Pro Ser Val Thr Gly  Phe Ile Thr Gln Val  Thr Ser Ser
    1850                 1855                 1860

Phe Ser  Ser Glu Leu Tyr Leu  Arg Phe Ser Lys Arg  Gly Lys Leu
    1865                 1870                 1875

Phe Arg  Asp Ala Glu Tyr Leu  Thr Ser Ser Thr Leu  Arg Glu Met
    1880                 1885                 1890

Ser Leu  Val Leu Phe Asn Cys  Ser Ser Pro Lys Ser  Glu Met Gln
    1895                 1900                 1905

Arg Ala  Arg Ser Leu Asn Tyr  Gln Asp Leu Val Arg  Gly Phe Pro
    1910                 1915                 1920

Glu Glu  Ile Ile Ser Asn Pro  Tyr Asn Glu Met Ile  Ile Thr Leu
    1925                 1930                 1935

Ile Asp  Ser Asp Val Glu Ser  Phe Leu Val His Lys  Met Val Asp
    1940                 1945                 1950

Asp Leu  Glu Leu Gln Arg Gly  Thr Leu Ser Lys Val  Ala Ile Ile
    1955                 1960                 1965

Ile Ala  Ile Met Ile Val Phe  Ser Asn Arg Val Phe  Asn Val Ser
    1970                 1975                 1980

Lys Pro  Leu Thr Asp Pro Leu  Phe Tyr Pro Pro Ser  Asp Pro Lys
    1985                 1990                 1995

Ile Leu  Arg His Phe Asn Ile  Cys Arg Ser Thr Met  Met Tyr Leu
    2000                 2005                 2010

Ser Thr  Ala Leu Gly Asp Val  Pro Ser Phe Ala Arg  Leu His Asp
    2015                 2020                 2025

Leu Tyr  Asn Arg Pro Ile Thr  Tyr Tyr Phe Arg Lys  Gln Phe Ile
    2030                 2035                 2040

Arg Gly  Asn Val Tyr Leu Ser  Trp Ser Trp Ser Asn  Asp Thr Ser
    2045                 2050                 2055

Val Phe  Lys Arg Val Ala Cys  Asn Ser Ser Leu Ser  Leu Ser Ser
    2060                 2065                 2070

His Trp  Ile Arg Leu Ile Tyr  Lys Ile Val Lys Ala  Thr Arg Leu
    2075                 2080                 2085

Val Gly  Ser Ile Lys Asp Leu  Ser Arg Glu Val Glu  Arg His Leu
    2090                 2095                 2100

His Arg  Tyr Asn Arg Trp Ile  Thr Leu Glu Asp Ile  Arg Ser Arg
    2105                 2110                 2115

Ser Ser  Leu Leu Asp Tyr Ser  Cys Leu
    2120                 2125
```

<210> SEQ ID NO 7
<211> LENGTH: 1281
<212> TYPE: DNA

```
<213> ORGANISM: Canis familiaris
<220> FEATURE:
<221> NAME/KEY: CDS
<222> LOCATION: (1)..(1281)

<400> SEQUENCE: 7

atg ggg ctg agc tat gga att ttc atc tgt ttt ctg ctc ctg gga ggc      48
Met Gly Leu Ser Tyr Gly Ile Phe Ile Cys Phe Leu Leu Leu Gly Gly
1               5                   10                  15

atg gag ctg tgc tgc ccc cag acc atc tgg cca act gag acc tac tac      96
Met Glu Leu Cys Cys Pro Gln Thr Ile Trp Pro Thr Glu Thr Tyr Tyr
            20                  25                  30

cca ttg aca tct agg ccc cca gta atg gtg gac tgt ctg gag tcc cag     144
Pro Leu Thr Ser Arg Pro Pro Val Met Val Asp Cys Leu Glu Ser Gln
        35                  40                  45

ctg gtg gtc act gtc agc aaa gac ctt ttt ggt act ggg aag ctc atc     192
Leu Val Val Thr Val Ser Lys Asp Leu Phe Gly Thr Gly Lys Leu Ile
    50                  55                  60

agg cca gca gac ctc acc ctg ggt cca gag aac tgt gag ccc ctg gtc     240
Arg Pro Ala Asp Leu Thr Leu Gly Pro Glu Asn Cys Glu Pro Leu Val
65                  70                  75                  80

tcc atg gac acg gat gat gtg gtc agg ttt gag gtt ggg ctg cac gag     288
Ser Met Asp Thr Asp Asp Val Val Arg Phe Glu Val Gly Leu His Glu
                85                  90                  95

tgt ggc agc agg gtg cag gtg act gac aat gct ctg gtg tac agc acc     336
Cys Gly Ser Arg Val Gln Val Thr Asp Asn Ala Leu Val Tyr Ser Thr
            100                 105                 110

ttc ctg atc cac agc ccc cgc cct gcg ggc aac ctg tcc atc ctg aga     384
Phe Leu Ile His Ser Pro Arg Pro Ala Gly Asn Leu Ser Ile Leu Arg
        115                 120                 125

act aat cgt gcc gag gtt ccc atc gag tgc cac tac ccc agg cac agc     432
Thr Asn Arg Ala Glu Val Pro Ile Glu Cys His Tyr Pro Arg His Ser
    130                 135                 140

aat gtg agc agc cag gcc atc ctg ccc act tgg gtg ccc ttc agg acc     480
Asn Val Ser Ser Gln Ala Ile Leu Pro Thr Trp Val Pro Phe Arg Thr
145                 150                 155                 160

aca atg ctc ttc gag gag aag cta gtt ttc tct ctc cgc cta atg gag     528
Thr Met Leu Phe Glu Glu Lys Leu Val Phe Ser Leu Arg Leu Met Glu
                165                 170                 175

gag gac tgg ggc tcc gag aag caa tcc ccc aca ttc cag ctg gga gac     576
Glu Asp Trp Gly Ser Glu Lys Gln Ser Pro Thr Phe Gln Leu Gly Asp
            180                 185                 190

ata gcc cac ctc cag gct gaa gtc cac act ggc agc cat atg cca ctg     624
Ile Ala His Leu Gln Ala Glu Val His Thr Gly Ser His Met Pro Leu
        195                 200                 205

cga ctt ttt gtg gac cac tgt gtg gcc acg ctg aca cca gat cgg aat     672
Arg Leu Phe Val Asp His Cys Val Ala Thr Leu Thr Pro Asp Arg Asn
    210                 215                 220

gcc ttc cct cat cac aaa att gtg gac ttc cat ggc tgt ctt gtg gat     720
Ala Phe Pro His His Lys Ile Val Asp Phe His Gly Cys Leu Val Asp
225                 230                 235                 240

ggt ctc tac aat tcc tct tca gcc ttc aaa gcc ccc aga ccc agg cca     768
Gly Leu Tyr Asn Ser Ser Ser Ala Phe Lys Ala Pro Arg Pro Arg Pro
                245                 250                 255

gag act ctt cag ttc aca gtg gat gtt ttc cac ttt gct aag gac tca     816
Glu Thr Leu Gln Phe Thr Val Asp Val Phe His Phe Ala Lys Asp Ser
            260                 265                 270

aga aac acg atc tat atc acc tgc cat ctg aag gtc act ccg gct gac     864
Arg Asn Thr Ile Tyr Ile Thr Cys His Leu Lys Val Thr Pro Ala Asp
        275                 280                 285

cga gtc cca gac cag cta aac aaa gct tgt tcc ttc atc aag tct acc     912
```

-continued

```
Arg Val Pro Asp Gln Leu Asn Lys Ala Cys Ser Phe Ile Lys Ser Thr
    290                 295                 300

aag agg tcc tac cct gta gaa ggc tcg gct gat att tgt cgc tgt tgt      960
Lys Arg Ser Tyr Pro Val Glu Gly Ser Ala Asp Ile Cys Arg Cys Cys
305                 310                 315                 320

aac aaa ggc agc tgt ggc ctt cca ggc cgg tcc agg agg ctg tcc cac     1008
Asn Lys Gly Ser Cys Gly Leu Pro Gly Arg Ser Arg Arg Leu Ser His
                325                 330                 335

cta gag aga ggg tgg cgc agg tct gtt tcc cac act aga aat cgc agg     1056
Leu Glu Arg Gly Trp Arg Arg Ser Val Ser His Thr Arg Asn Arg Arg
            340                 345                 350

cac gtg act gaa gaa gca gag atc acc gtg ggg cct ctg atc ttc ctg     1104
His Val Thr Glu Glu Ala Glu Ile Thr Val Gly Pro Leu Ile Phe Leu
        355                 360                 365

gga aag gct agt gat cat ggt ata gag ggg tca acc tct cct cac acc     1152
Gly Lys Ala Ser Asp His Gly Ile Glu Gly Ser Thr Ser Pro His Thr
    370                 375                 380

tct gtg atg ttg ggc tta ggc ctg gcc acg gtg gta tcc ctg act cta     1200
Ser Val Met Leu Gly Leu Gly Leu Ala Thr Val Val Ser Leu Thr Leu
385                 390                 395                 400

gct acc att gtc ctg gtc ctt gcc aag agg cat cgt act gct tcc cac     1248
Ala Thr Ile Val Leu Val Leu Ala Lys Arg His Arg Thr Ala Ser His
                405                 410                 415

cct gtg ata tgc cct gca tct gtc tcc caa taa                         1281
Pro Val Ile Cys Pro Ala Ser Val Ser Gln
            420                 425


<210> SEQ ID NO 8
<211> LENGTH: 426
<212> TYPE: PRT
<213> ORGANISM: Canis familiaris

<400> SEQUENCE: 8

Met Gly Leu Ser Tyr Gly Ile Phe Ile Cys Phe Leu Leu Leu Gly Gly
1               5                   10                  15

Met Glu Leu Cys Cys Pro Gln Thr Ile Trp Pro Thr Glu Thr Tyr Tyr
            20                  25                  30

Pro Leu Thr Ser Arg Pro Pro Val Met Val Asp Cys Leu Glu Ser Gln
        35                  40                  45

Leu Val Val Thr Val Ser Lys Asp Leu Phe Gly Thr Gly Lys Leu Ile
    50                  55                  60

Arg Pro Ala Asp Leu Thr Leu Gly Pro Glu Asn Cys Glu Pro Leu Val
65                  70                  75                  80

Ser Met Asp Thr Asp Asp Val Val Arg Phe Glu Val Gly Leu His Glu
                85                  90                  95

Cys Gly Ser Arg Val Gln Val Thr Asp Asn Ala Leu Val Tyr Ser Thr
            100                 105                 110

Phe Leu Ile His Ser Pro Arg Pro Ala Gly Asn Leu Ser Ile Leu Arg
        115                 120                 125

Thr Asn Arg Ala Glu Val Pro Ile Glu Cys His Tyr Pro Arg His Ser
    130                 135                 140

Asn Val Ser Ser Gln Ala Ile Leu Pro Thr Trp Val Pro Phe Arg Thr
145                 150                 155                 160

Thr Met Leu Phe Glu Glu Lys Leu Val Phe Ser Leu Arg Leu Met Glu
                165                 170                 175

Glu Asp Trp Gly Ser Glu Lys Gln Ser Pro Thr Phe Gln Leu Gly Asp
            180                 185                 190

Ile Ala His Leu Gln Ala Glu Val His Thr Gly Ser His Met Pro Leu
```

```
        195                 200                 205

Arg Leu Phe Val Asp His Cys Val Ala Thr Leu Thr Pro Asp Arg Asn
    210                 215                 220

Ala Phe Pro His His Lys Ile Val Asp Phe His Gly Cys Leu Val Asp
225                 230                 235                 240

Gly Leu Tyr Asn Ser Ser Ser Ala Phe Lys Ala Pro Arg Pro Arg Pro
                245                 250                 255

Glu Thr Leu Gln Phe Thr Val Asp Val Phe His Phe Ala Lys Asp Ser
            260                 265                 270

Arg Asn Thr Ile Tyr Ile Thr Cys His Leu Lys Val Thr Pro Ala Asp
        275                 280                 285

Arg Val Pro Asp Gln Leu Asn Lys Ala Cys Ser Phe Ile Lys Ser Thr
    290                 295                 300

Lys Arg Ser Tyr Pro Val Glu Gly Ser Ala Asp Ile Cys Arg Cys Cys
305                 310                 315                 320

Asn Lys Gly Ser Cys Gly Leu Pro Gly Arg Ser Arg Arg Leu Ser His
                325                 330                 335

Leu Glu Arg Gly Trp Arg Arg Ser Val Ser His Thr Arg Asn Arg Arg
            340                 345                 350

His Val Thr Glu Glu Ala Glu Ile Thr Val Gly Pro Leu Ile Phe Leu
        355                 360                 365

Gly Lys Ala Ser Asp His Gly Ile Glu Gly Ser Thr Ser Pro His Thr
    370                 375                 380

Ser Val Met Leu Gly Leu Gly Leu Ala Thr Val Val Ser Leu Thr Leu
385                 390                 395                 400

Ala Thr Ile Val Leu Val Leu Ala Lys Arg His Arg Thr Ala Ser His
                405                 410                 415

Pro Val Ile Cys Pro Ala Ser Val Ser Gln
            420                 425
```

<210> SEQ ID NO 9
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 9
aaaactgcag ccaccatg 18

<210> SEQ ID NO 10
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 10
aactgcagcc accatggggc tgagctatgg aattttcatc tgttttctgc tcct 54

<210> SEQ ID NO 11
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 11
tttcatctgt tttctgctcc tgggaggcat ggagctgtgc tgcccccaga ccat 54

<210> SEQ ID NO 12
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 12
ctgcccccag accatctggc caactgagac ctactaccca ttgacatcta ggcc 54

<210> SEQ ID NO 13
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 13
cccattgaca tctaggcccc cagtaatggt ggactgtctg gagtcccagc tggt 54

<210> SEQ ID NO 14
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 14
ggagtcccag ctggtggtca ctgtcagcaa agaccttttt ggtactggga agct 54

<210> SEQ ID NO 15
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 15
ctttttggtt acgggaagct catcaggcca gcagacctca ccctgggtcc agag 54

<210> SEQ ID NO 16
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 16
caccctgggt ccagagaact gtgagcccct ggtctccatg gacacggatg atgt 54

<210> SEQ ID NO 17
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 17
catggacacg gatgatgtgg tcaggtttga ggttgggctg cacgagtgtg gcag 54

<210> SEQ ID NO 18
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 18
gtgctgtaca ccagagcatt gtcagtcacc tgcaccctgc tgccacactc gtgc 54

<210> SEQ ID NO 19
<211> LENGTH: 54
<212> TYPE: DNA
<213> ORGANISM: Artificial Sequence
<220> FEATURE:
<223> OTHER INFORMATION: Synethic oligonucleotide

<400> SEQUENCE: 19
caggttgccc gcagggcggg ggctgtggat caggaaggtg ctgtacacca gagc 54

<210> SEQ ID NO 20
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 20
actcgatggg gacctcggca cgattagttc tcaggatgga caggttgccc gcag 54

<210> SEQ ID NO 21
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 21
ggcctggctg ctcacattgc tgtgcctggg gtagtggcac tcgatgggga cctc 54

<210> SEQ ID NO 22
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 22
agagcattgt ggtcctgaag ggcacccaag tgggcaggat ggcctggctg ctca 54

<210> SEQ ID NO 23
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 23
ccattaggcg gagagagaaa actagcttct cctcgaagag cattgtggtc ctga 54

<210> SEQ ID NO 24
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 24
atgtggggga ttgcttctcg gagccccagt cctcctccat taggcggaga gaga 54

<210> SEQ ID NO 25
<211> LENGTH: 54
<212> TYPE: DNA

<213> ORGANISM: Artificial Sequence
<220> FEATURE:
<223> OTHER INFORMATION: Synthetic oligonucleotide

<400> SEQUENCE: 25
cttcagcctg gaggtgggct atgtctccca gctggaatgt gggggattgc ttct 54

<210> SEQ ID NO 26
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 26
acaaaaagtc gcagtggcat atggctgcca gtgtggactt cagcctggag gtg 53

<210> SEQ ID NO 27
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 27
tggcagccat atgccactgc gactttttgt ggaccactgt 40

<210> SEQ ID NO 28
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 28
gactttttgt ggaccactgt gtggccacgc tgacaccaga tcggaatgcc ttcc 54

<210> SEQ ID NO 29
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 29
cagatcggaa tgccttccct catcacaaaa ttgtggactt ccatggctgt cttg 54

<210> SEQ ID NO 30
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 30
gacttccatg gctgtcttgt ggatggtctc tacaattcct cttcagcctt caaa 54

<210> SEQ ID NO 31
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 31
aattcctctt cagccttcaa agcccccaga cccaggccag agactcttca gttc 54

<210> SEQ ID NO 32
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 32
gccagagact cttcagttca cagtggatgt tttccacttt gctaaggact caag 54

<210> SEQ ID NO 33
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 33
ccactttgct aaggactcaa gaaacacgat ctatatcacc tgccatctga aggt 54

<210> SEQ ID NO 34
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 34
acctgccatc tgaaggtcac tccggctgac cgagtcccag accagctaaa caaa 54

<210> SEQ ID NO 35
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 35
cccagaccag ctaaacaaag cttgttcctt catcaagtct accaagaggt ccta 54

<210> SEQ ID NO 36
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 36
caagtctacc aagaggtcct accctgtaga aggctcggct gatatttgtc gctg 54

<210> SEQ ID NO 37
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 37
accggcctgg aaggccacag ctgcctttgt tacaacagcg acaaatatca gccg 54

<210> SEQ ID NO 38
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 38
gacctgcgcc accctctctc taggtgggac agcctcctgg accggcctgg aagg 54

<210> SEQ ID NO 39
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 39
ttcttcagtc acgtgcctgc gatttctagt gtgggaaaca gacctgcgcc accc 54

<210> SEQ ID NO 40
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 40
ttcccaggaa gatcagaggc cccacggtga tctctgcttc ttcagtcacg tgcc 54

<210> SEQ ID NO 41
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 41
agaggttgac ccctctatac catgatcact agcctttccc aggaagatca gagg 54

<210> SEQ ID NO 42
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 42
ccaggcctaa gcccaacatc acagaggtgt gaggagaggt tgacccctct atac 54

<210> SEQ ID NO 43
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 43
ccaggacaat ggtagctaga gtcagggata ccaccgtggc caggcctaag ccca 54

<210> SEQ ID NO 44
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 44
gggtgggaag cagtacgatg cctcttggca aggaccagga caatggtagc taga 54

<210> SEQ ID NO 45
<211> LENGTH: 54
<212> TYPE: DNA

<213> ORGANISM: Artificial Sequence
<220> FEATURE:
<223> OTHER INFORMATION: Synthetic oligonucleotide

<400> SEQUENCE: 45
cggtacctta ttgggagaca gatgcagggc atatcacagg gtgggaagca gtac 54

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 46
gacggcggta ccttattggg agac 24

<210> SEQ ID NO 47
<211> LENGTH: 30
<212> TYPE: DNA
<213> ORGANISM: Canis familiaris
<220> FEATURE:
<221> NAME/KEY: CDS
<222> LOCATION: (1)..(30)

<400> SEQUENCE: 47

```
gaa cac tgg agc tac ggt ttg aga ccc ggg                          30
Glu His Trp Ser Tyr Gly Leu Arg Pro Gly
1               5                   10
```

<210> SEQ ID NO 48
<211> LENGTH: 10
<212> TYPE: PRT
<213> ORGANISM: Canis familiaris

<400> SEQUENCE: 48

```
Glu His Trp Ser Tyr Gly Leu Arg Pro Gly
1               5                   10
```

<210> SEQ ID NO 49
<211> LENGTH: 1605
<212> TYPE: DNA
<213> ORGANISM: Artificial Sequence
<220> FEATURE:
<223> OTHER INFORMATION: Recombinant Rabies Virus Glycoprotein N-GnRH
<220> FEATURE:
<221> NAME/KEY: CDS
<222> LOCATION: (1)..(1605)

<400> SEQUENCE: 49

```
atg gtt cct cag gct ctc ctg ttt gta ccc ctt ctg gtt ttt cca ttg       48
Met Val Pro Gln Ala Leu Leu Phe Val Pro Leu Leu Val Phe Pro Leu
1               5                   10                  15

tgt ttt ggg gaa cac tgg agc tac ggt ttg aga ccc ggg aaa ttc cct       96
Cys Phe Gly Glu His Trp Ser Tyr Gly Leu Arg Pro Gly Lys Phe Pro
            20                  25                  30

att tac acg ata cca gac aag ctt ggt ccc tgg agt ccg att gac ata      144
Ile Tyr Thr Ile Pro Asp Lys Leu Gly Pro Trp Ser Pro Ile Asp Ile
        35                  40                  45

cat cac ctc agc tgc cca aac aat ttg gta gtg gag gac gaa gga tgc      192
His His Leu Ser Cys Pro Asn Asn Leu Val Val Glu Asp Glu Gly Cys
    50                  55                  60

acc aac ctg tca ggg ttc tcc tac atg gaa ctt aaa gtt gga tac atc      240
Thr Asn Leu Ser Gly Phe Ser Tyr Met Glu Leu Lys Val Gly Tyr Ile
65                  70                  75                  80

tta gcc ata aaa gtg aac ggg ttc act tgc aca ggc gtt gtg acg gag      288
```

-continued

```
Leu Ala Ile Lys Val Asn Gly Phe Thr Cys Thr Gly Val Val Thr Glu
                85                  90                  95

gct gaa acc tac act aac ttc gtt ggt tat gtc aca acc acg ttc aaa      336
Ala Glu Thr Tyr Thr Asn Phe Val Gly Tyr Val Thr Thr Thr Phe Lys
            100                 105                 110

aga aag cat ttc cgc cca aca cca gat gca tgt aga gcc gcg tac aac      384
Arg Lys His Phe Arg Pro Thr Pro Asp Ala Cys Arg Ala Ala Tyr Asn
        115                 120                 125

tgg aag atg gcc ggt gac ccc aga tat gaa gag tct cta cac aat ccg      432
Trp Lys Met Ala Gly Asp Pro Arg Tyr Glu Glu Ser Leu His Asn Pro
    130                 135                 140

tac cct gac tac cgc tgg ctt cga act gta aaa acc acc aag gag tct      480
Tyr Pro Asp Tyr Arg Trp Leu Arg Thr Val Lys Thr Thr Lys Glu Ser
145                 150                 155                 160

ctc gtt atc ata tct cca agt gtg gca gat ttg gac cca tat gac aga      528
Leu Val Ile Ile Ser Pro Ser Val Ala Asp Leu Asp Pro Tyr Asp Arg
                165                 170                 175

tcc ctt cac tcg agg gtc ttc cct agc ggg aag tgc tca gga gta gcg      576
Ser Leu His Ser Arg Val Phe Pro Ser Gly Lys Cys Ser Gly Val Ala
            180                 185                 190

gtg tct tct acc tac tgc tcc act aac cac gat tac acc att tgg atg      624
Val Ser Ser Thr Tyr Cys Ser Thr Asn His Asp Tyr Thr Ile Trp Met
        195                 200                 205

ccc gag aat ccg aga cta ggg atg tct tgt gac att ttt acc aat agt      672
Pro Glu Asn Pro Arg Leu Gly Met Ser Cys Asp Ile Phe Thr Asn Ser
    210                 215                 220

aga ggg aag aga gca tcc aaa ggg agt gag act tgc ggc ttt gta gat      720
Arg Gly Lys Arg Ala Ser Lys Gly Ser Glu Thr Cys Gly Phe Val Asp
225                 230                 235                 240

gaa aga ggc cta tat aag tct tta aaa gga gca tgc aaa ctc aag tta      768
Glu Arg Gly Leu Tyr Lys Ser Leu Lys Gly Ala Cys Lys Leu Lys Leu
                245                 250                 255

tgt gga gtt cta gga ctt aga ctt atg gat gga aca tgg gtc tcg atg      816
Cys Gly Val Leu Gly Leu Arg Leu Met Asp Gly Thr Trp Val Ser Met
            260                 265                 270

caa aca tca aat gaa acc aaa tgg tgc cct ccc gat aag ttg gtg aac      864
Gln Thr Ser Asn Glu Thr Lys Trp Cys Pro Pro Asp Lys Leu Val Asn
        275                 280                 285

ctg cac gac ttt cgc tca gac gaa att gag cac ctt gtt gta gag gag      912
Leu His Asp Phe Arg Ser Asp Glu Ile Glu His Leu Val Val Glu Glu
    290                 295                 300

ttg gtc agg aag aga gag gag tgt ctg gat gca cta gag tcc atc atg      960
Leu Val Arg Lys Arg Glu Glu Cys Leu Asp Ala Leu Glu Ser Ile Met
305                 310                 315                 320

aca acc aag tca gtg agt ttc aga cgt ctc agt cat tta aga aaa ctt     1008
Thr Thr Lys Ser Val Ser Phe Arg Arg Leu Ser His Leu Arg Lys Leu
                325                 330                 335

gtc cct ggg ttt gga aaa gca tat acc ata ttc aac aag acc ttg atg     1056
Val Pro Gly Phe Gly Lys Ala Tyr Thr Ile Phe Asn Lys Thr Leu Met
            340                 345                 350

gaa gcc gat gct cac tac aag tca gtc gaa act tgg aat gag atc ctc     1104
Glu Ala Asp Ala His Tyr Lys Ser Val Glu Thr Trp Asn Glu Ile Leu
        355                 360                 365

cct tca aaa ggg tgt tta aga gtt ggg ggg agg tgt cat cct cat gtg     1152
Pro Ser Lys Gly Cys Leu Arg Val Gly Gly Arg Cys His Pro His Val
    370                 375                 380

aac ggg gtg ttt ttc aat ggt ata ata tta gga cct gac ggc aat gtc     1200
Asn Gly Val Phe Phe Asn Gly Ile Ile Leu Gly Pro Asp Gly Asn Val
385                 390                 395                 400

tta atc cca gag atg caa tca tcc ctc ctc cag caa cat atg gag ttg     1248
```

```
Leu Ile Pro Glu Met Gln Ser Ser Leu Leu Gln Gln His Met Glu Leu
                405                 410                 415

ttg gaa tcc tcg gtt atc ccc ctt gtg cac ccc ctg gca gac ccg tct     1296
Leu Glu Ser Ser Val Ile Pro Leu Val His Pro Leu Ala Asp Pro Ser
            420                 425                 430

acc gtt ttc aag gac ggt gac gag gct gag gat ttt gtt gaa gtt cac     1344
Thr Val Phe Lys Asp Gly Asp Glu Ala Glu Asp Phe Val Glu Val His
        435                 440                 445

ctt ccc gat gtg cac aat cag gtc tca gga gtt gac ttg ggt ctc ccg     1392
Leu Pro Asp Val His Asn Gln Val Ser Gly Val Asp Leu Gly Leu Pro
    450                 455                 460

aac tgg ggg aag tat gta tta ctg agt gca ggg gcc ctg act gcc ttg     1440
Asn Trp Gly Lys Tyr Val Leu Leu Ser Ala Gly Ala Leu Thr Ala Leu
465                 470                 475                 480

atg ttg ata att ttc ctg atg aca tgt tgt aga aga gtc aat cga tca     1488
Met Leu Ile Ile Phe Leu Met Thr Cys Cys Arg Arg Val Asn Arg Ser
                485                 490                 495

gaa cct acg caa cac aat ctc aga ggg aca ggg agg gag gtg tca gtc     1536
Glu Pro Thr Gln His Asn Leu Arg Gly Thr Gly Arg Glu Val Ser Val
            500                 505                 510

act ccc caa agc ggg aag atc ata tct tca tgg gaa tca cac aag agt     1584
Thr Pro Gln Ser Gly Lys Ile Ile Ser Ser Trp Glu Ser His Lys Ser
        515                 520                 525

ggg ggt gag acc ata ctg taa                                         1605
Gly Gly Glu Thr Ile Leu
    530


<210> SEQ ID NO 50
<211> LENGTH: 534
<212> TYPE: PRT
<213> ORGANISM: Artificial Sequence
<220> FEATURE:
<223> OTHER INFORMATION: Synthetic Construct

<400> SEQUENCE: 50

Met Val Pro Gln Ala Leu Leu Phe Val Pro Leu Leu Val Phe Pro Leu
1               5                   10                  15

Cys Phe Gly Glu His Trp Ser Tyr Gly Leu Arg Pro Gly Lys Phe Pro
            20                  25                  30

Ile Tyr Thr Ile Pro Asp Lys Leu Gly Pro Trp Ser Pro Ile Asp Ile
        35                  40                  45

His His Leu Ser Cys Pro Asn Asn Leu Val Val Glu Asp Glu Gly Cys
    50                  55                  60

Thr Asn Leu Ser Gly Phe Ser Tyr Met Glu Leu Lys Val Gly Tyr Ile
65                  70                  75                  80

Leu Ala Ile Lys Val Asn Gly Phe Thr Cys Thr Gly Val Val Thr Glu
                85                  90                  95

Ala Glu Thr Tyr Thr Asn Phe Val Gly Tyr Val Thr Thr Thr Phe Lys
            100                 105                 110

Arg Lys His Phe Arg Pro Thr Pro Asp Ala Cys Arg Ala Ala Tyr Asn
        115                 120                 125

Trp Lys Met Ala Gly Asp Pro Arg Tyr Glu Glu Ser Leu His Asn Pro
    130                 135                 140

Tyr Pro Asp Tyr Arg Trp Leu Arg Thr Val Lys Thr Thr Lys Glu Ser
145                 150                 155                 160

Leu Val Ile Ile Ser Pro Ser Val Ala Asp Leu Asp Pro Tyr Asp Arg
                165                 170                 175

Ser Leu His Ser Arg Val Phe Pro Ser Gly Lys Cys Ser Gly Val Ala
            180                 185                 190
```

Val Ser Ser Thr Tyr Cys Ser Thr Asn His Asp Tyr Thr Ile Trp Met
195 200 205

Pro Glu Asn Pro Arg Leu Gly Met Ser Cys Asp Ile Phe Thr Asn Ser
210 215 220

Arg Gly Lys Arg Ala Ser Lys Gly Ser Glu Thr Cys Gly Phe Val Asp
225 230 235 240

Glu Arg Gly Leu Tyr Lys Ser Leu Lys Gly Ala Cys Lys Leu Lys Leu
245 250 255

Cys Gly Val Leu Gly Leu Arg Leu Met Asp Gly Thr Trp Val Ser Met
260 265 270

Gln Thr Ser Asn Glu Thr Lys Trp Cys Pro Pro Asp Lys Leu Val Asn
275 280 285

Leu His Asp Phe Arg Ser Asp Glu Ile Glu His Leu Val Val Glu Glu
290 295 300

Leu Val Arg Lys Arg Glu Glu Cys Leu Asp Ala Leu Glu Ser Ile Met
305 310 315 320

Thr Thr Lys Ser Val Ser Phe Arg Arg Leu Ser His Leu Arg Lys Leu
325 330 335

Val Pro Gly Phe Gly Lys Ala Tyr Thr Ile Phe Asn Lys Thr Leu Met
340 345 350

Glu Ala Asp Ala His Tyr Lys Ser Val Glu Thr Trp Asn Glu Ile Leu
355 360 365

Pro Ser Lys Gly Cys Leu Arg Val Gly Gly Arg Cys His Pro His Val
370 375 380

Asn Gly Val Phe Phe Asn Gly Ile Ile Leu Gly Pro Asp Gly Asn Val
385 390 395 400

Leu Ile Pro Glu Met Gln Ser Ser Leu Leu Gln Gln His Met Glu Leu
405 410 415

Leu Glu Ser Ser Val Ile Pro Leu Val His Pro Leu Ala Asp Pro Ser
420 425 430

Thr Val Phe Lys Asp Gly Asp Glu Ala Glu Asp Phe Val Glu Val His
435 440 445

Leu Pro Asp Val His Asn Gln Val Ser Gly Val Asp Leu Gly Leu Pro
450 455 460

Asn Trp Gly Lys Tyr Val Leu Leu Ser Ala Gly Ala Leu Thr Ala Leu
465 470 475 480

Met Leu Ile Ile Phe Leu Met Thr Cys Cys Arg Arg Val Asn Arg Ser
485 490 495

Glu Pro Thr Gln His Asn Leu Arg Gly Thr Gly Arg Glu Val Ser Val
500 505 510

Thr Pro Gln Ser Gly Lys Ile Ile Ser Ser Trp Glu Ser His Lys Ser
515 520 525

Gly Gly Glu Thr Ile Leu
530

<210> SEQ ID NO 51
<211> LENGTH: 1635
<212> TYPE: DNA
<213> ORGANISM: Artificial Sequence
<220> FEATURE:
<223> OTHER INFORMATION: Recombinant Rabies Virus Glycoprotein N-2GnRH
<220> FEATURE:
<221> NAME/KEY: CDS
<222> LOCATION: (1)..(1635)

<400> SEQUENCE: 51

-continued

```
atg gtt cct cag gct ctc ctg ttt gta ccc ctt ctg gtt ttt cca ttg        48
Met Val Pro Gln Ala Leu Leu Phe Val Pro Leu Leu Val Phe Pro Leu
1               5                   10                  15

tgt ttt ggg gaa cac tgg agc tac ggt ttg aga ccc ggg gaa cac tgg        96
Cys Phe Gly Glu His Trp Ser Tyr Gly Leu Arg Pro Gly Glu His Trp
            20                  25                  30

agc tac ggt ttg aga ccc ggg aaa ttc cct att tac acg ata cca gac       144
Ser Tyr Gly Leu Arg Pro Gly Lys Phe Pro Ile Tyr Thr Ile Pro Asp
        35                  40                  45

aag ctt ggt ccc tgg agt ccg att gac ata cat cac ctc agc tgc cca       192
Lys Leu Gly Pro Trp Ser Pro Ile Asp Ile His His Leu Ser Cys Pro
    50                  55                  60

aac aat ttg gta gtg gag gac gaa gga tgc acc aac ctg tca ggg ttc       240
Asn Asn Leu Val Val Glu Asp Glu Gly Cys Thr Asn Leu Ser Gly Phe
65                  70                  75                  80

tcc tac atg gaa ctt aaa gtt gga tac atc tta gcc ata aaa gtg aac       288
Ser Tyr Met Glu Leu Lys Val Gly Tyr Ile Leu Ala Ile Lys Val Asn
                85                  90                  95

ggg ttc act tgc aca ggc gtt gtg acg gag gct gaa acc tac act aac       336
Gly Phe Thr Cys Thr Gly Val Val Thr Glu Ala Glu Thr Tyr Thr Asn
            100                 105                 110

ttc gtt ggt tat gtc aca acc acg ttc aaa aga aag cat ttc cgc cca       384
Phe Val Gly Tyr Val Thr Thr Thr Phe Lys Arg Lys His Phe Arg Pro
        115                 120                 125

aca cca gat gca tgt aga gcc gcg tac aac tgg aag atg gcc ggt gac       432
Thr Pro Asp Ala Cys Arg Ala Ala Tyr Asn Trp Lys Met Ala Gly Asp
    130                 135                 140

ccc aga tat gaa gag tct cta cac aat ccg tac cct gac tac cgc tgg       480
Pro Arg Tyr Glu Glu Ser Leu His Asn Pro Tyr Pro Asp Tyr Arg Trp
145                 150                 155                 160

ctt cga act gta aaa acc acc aag gag tct ctc gtt atc ata tct cca       528
Leu Arg Thr Val Lys Thr Thr Lys Glu Ser Leu Val Ile Ile Ser Pro
                165                 170                 175

agt gtg gca gat ttg gac cca tat gac aga tcc ctt cac tcg agg gtc       576
Ser Val Ala Asp Leu Asp Pro Tyr Asp Arg Ser Leu His Ser Arg Val
            180                 185                 190

ttc cct agc ggg aag tgc tca gga gta gcg gtg tct tct acc tac tgc       624
Phe Pro Ser Gly Lys Cys Ser Gly Val Ala Val Ser Ser Thr Tyr Cys
        195                 200                 205

tcc act aac cac gat tac acc att tgg atg ccc gag aat ccg aga cta       672
Ser Thr Asn His Asp Tyr Thr Ile Trp Met Pro Glu Asn Pro Arg Leu
    210                 215                 220

ggg atg tct tgt gac att ttt acc aat agt aga ggg aag aga gca tcc       720
Gly Met Ser Cys Asp Ile Phe Thr Asn Ser Arg Gly Lys Arg Ala Ser
225                 230                 235                 240

aaa ggg agt gag act tgc ggc ttt gta gat gaa aga ggc cta tat aag       768
Lys Gly Ser Glu Thr Cys Gly Phe Val Asp Glu Arg Gly Leu Tyr Lys
                245                 250                 255

tct tta aaa gga gca tgc aaa ctc aag tta tgt gga gtt cta gga ctt       816
Ser Leu Lys Gly Ala Cys Lys Leu Lys Leu Cys Gly Val Leu Gly Leu
            260                 265                 270

aga ctt atg gat gga aca tgg gtc tcg atg caa aca tca aat gaa acc       864
Arg Leu Met Asp Gly Thr Trp Val Ser Met Gln Thr Ser Asn Glu Thr
        275                 280                 285

aaa tgg tgc cct ccc gat aag ttg gtg aac ctg cac gac ttt cgc tca       912
Lys Trp Cys Pro Pro Asp Lys Leu Val Asn Leu His Asp Phe Arg Ser
    290                 295                 300

gac gaa att gag cac ctt gtt gta gag gag ttg gtc agg aag aga gag       960
Asp Glu Ile Glu His Leu Val Val Glu Glu Leu Val Arg Lys Arg Glu
305                 310                 315                 320
```

```
gag tgt ctg gat gca cta gag tcc atc atg aca acc aag tca gtg agt      1008
Glu Cys Leu Asp Ala Leu Glu Ser Ile Met Thr Thr Lys Ser Val Ser
                325                 330                 335

ttc aga cgt ctc agt cat tta aga aaa ctt gtc cct ggg ttt gga aaa      1056
Phe Arg Arg Leu Ser His Leu Arg Lys Leu Val Pro Gly Phe Gly Lys
            340                 345                 350

gca tat acc ata ttc aac aag acc ttg atg gaa gcc gat gct cac tac      1104
Ala Tyr Thr Ile Phe Asn Lys Thr Leu Met Glu Ala Asp Ala His Tyr
        355                 360                 365

aag tca gtc gaa act tgg aat gag atc ctc cct tca aaa ggg tgt tta      1152
Lys Ser Val Glu Thr Trp Asn Glu Ile Leu Pro Ser Lys Gly Cys Leu
    370                 375                 380

aga gtt ggg ggg agg tgt cat cct cat gtg aac ggg gtg ttt ttc aat      1200
Arg Val Gly Gly Arg Cys His Pro His Val Asn Gly Val Phe Phe Asn
385                 390                 395                 400

ggt ata ata tta gga cct gac ggc aat gtc tta atc cca gag atg caa      1248
Gly Ile Ile Leu Gly Pro Asp Gly Asn Val Leu Ile Pro Glu Met Gln
                405                 410                 415

tca tcc ctc ctc cag caa cat atg gag ttg ttg gaa tcc tcg gtt atc      1296
Ser Ser Leu Leu Gln Gln His Met Glu Leu Leu Glu Ser Ser Val Ile
            420                 425                 430

ccc ctt gtg cac ccc ctg gca gac ccg tct acc gtt ttc aag gac ggt      1344
Pro Leu Val His Pro Leu Ala Asp Pro Ser Thr Val Phe Lys Asp Gly
        435                 440                 445

gac gag gct gag gat ttt gtt gaa gtt cac ctt ccc gat gtg cac aat      1392
Asp Glu Ala Glu Asp Phe Val Glu Val His Leu Pro Asp Val His Asn
    450                 455                 460

cag gtc tca gga gtt gac ttg ggt ctc ccg aac tgg ggg aag tat gta      1440
Gln Val Ser Gly Val Asp Leu Gly Leu Pro Asn Trp Gly Lys Tyr Val
465                 470                 475                 480

tta ctg agt gca ggg gcc ctg act gcc ttg atg ttg ata att ttc ctg      1488
Leu Leu Ser Ala Gly Ala Leu Thr Ala Leu Met Leu Ile Ile Phe Leu
                485                 490                 495

atg aca tgt tgt aga aga gtc aat cga tca gaa cct acg caa cac aat      1536
Met Thr Cys Cys Arg Arg Val Asn Arg Ser Glu Pro Thr Gln His Asn
            500                 505                 510

ctc aga ggg aca ggg agg gag gtg tca gtc act ccc caa agc ggg aag      1584
Leu Arg Gly Thr Gly Arg Glu Val Ser Val Thr Pro Gln Ser Gly Lys
        515                 520                 525

atc ata tct tca tgg gaa tca cac aag agt ggg ggt gag acc ata ctg      1632
Ile Ile Ser Ser Trp Glu Ser His Lys Ser Gly Gly Glu Thr Ile Leu
    530                 535                 540

taa                                                                  1635
```

<210> SEQ ID NO 52
<211> LENGTH: 544
<212> TYPE: PRT
<213> ORGANISM: Artificial Sequence
<220> FEATURE:
<223> OTHER INFORMATION: Synthetic Construct

<400> SEQUENCE: 52

```
Met Val Pro Gln Ala Leu Leu Phe Val Pro Leu Leu Val Phe Pro Leu
1               5                   10                  15

Cys Phe Gly Glu His Trp Ser Tyr Gly Leu Arg Pro Gly Glu His Trp
            20                  25                  30

Ser Tyr Gly Leu Arg Pro Gly Lys Phe Pro Ile Tyr Thr Ile Pro Asp
        35                  40                  45

Lys Leu Gly Pro Trp Ser Pro Ile Asp Ile His His Leu Ser Cys Pro
    50                  55                  60
```

```
Asn Asn Leu Val Val Glu Asp Glu Gly Cys Thr Asn Leu Ser Gly Phe
65                  70                  75                  80

Ser Tyr Met Glu Leu Lys Val Gly Tyr Ile Leu Ala Ile Lys Val Asn
                85                  90                  95

Gly Phe Thr Cys Thr Gly Val Val Thr Glu Ala Glu Thr Tyr Thr Asn
            100                 105                 110

Phe Val Gly Tyr Val Thr Thr Thr Phe Lys Arg Lys His Phe Arg Pro
        115                 120                 125

Thr Pro Asp Ala Cys Arg Ala Ala Tyr Asn Trp Lys Met Ala Gly Asp
    130                 135                 140

Pro Arg Tyr Glu Glu Ser Leu His Asn Pro Tyr Pro Asp Tyr Arg Trp
145                 150                 155                 160

Leu Arg Thr Val Lys Thr Thr Lys Glu Ser Leu Val Ile Ile Ser Pro
                165                 170                 175

Ser Val Ala Asp Leu Asp Pro Tyr Asp Arg Ser Leu His Ser Arg Val
            180                 185                 190

Phe Pro Ser Gly Lys Cys Ser Gly Val Ala Val Ser Ser Thr Tyr Cys
        195                 200                 205

Ser Thr Asn His Asp Tyr Thr Ile Trp Met Pro Glu Asn Pro Arg Leu
    210                 215                 220

Gly Met Ser Cys Asp Ile Phe Thr Asn Ser Arg Gly Lys Arg Ala Ser
225                 230                 235                 240

Lys Gly Ser Glu Thr Cys Gly Phe Val Asp Glu Arg Gly Leu Tyr Lys
                245                 250                 255

Ser Leu Lys Gly Ala Cys Lys Leu Lys Leu Cys Gly Val Leu Gly Leu
            260                 265                 270

Arg Leu Met Asp Gly Thr Trp Val Ser Met Gln Thr Ser Asn Glu Thr
        275                 280                 285

Lys Trp Cys Pro Pro Asp Lys Leu Val Asn Leu His Asp Phe Arg Ser
    290                 295                 300

Asp Glu Ile Glu His Leu Val Val Glu Glu Leu Val Arg Lys Arg Glu
305                 310                 315                 320

Glu Cys Leu Asp Ala Leu Glu Ser Ile Met Thr Thr Lys Ser Val Ser
                325                 330                 335

Phe Arg Arg Leu Ser His Leu Arg Lys Leu Val Pro Gly Phe Gly Lys
            340                 345                 350

Ala Tyr Thr Ile Phe Asn Lys Thr Leu Met Glu Ala Asp Ala His Tyr
        355                 360                 365

Lys Ser Val Glu Thr Trp Asn Glu Ile Leu Pro Ser Lys Gly Cys Leu
    370                 375                 380

Arg Val Gly Gly Arg Cys His Pro His Val Asn Gly Val Phe Phe Asn
385                 390                 395                 400

Gly Ile Ile Leu Gly Pro Asp Gly Asn Val Leu Ile Pro Glu Met Gln
                405                 410                 415

Ser Ser Leu Leu Gln Gln His Met Glu Leu Leu Glu Ser Ser Val Ile
            420                 425                 430

Pro Leu Val His Pro Leu Ala Asp Pro Ser Thr Val Phe Lys Asp Gly
        435                 440                 445

Asp Glu Ala Glu Asp Phe Val Glu Val His Leu Pro Asp Val His Asn
    450                 455                 460

Gln Val Ser Gly Val Asp Leu Gly Leu Pro Asn Trp Gly Lys Tyr Val
465                 470                 475                 480

Leu Leu Ser Ala Gly Ala Leu Thr Ala Leu Met Leu Ile Ile Phe Leu
                485                 490                 495
```

```
Met Thr Cys Cys Arg Arg Val Asn Arg Ser Glu Pro Thr Gln His Asn
            500                 505                 510

Leu Arg Gly Thr Gly Arg Glu Val Ser Val Thr Pro Gln Ser Gly Lys
        515                 520                 525

Ile Ile Ser Ser Trp Glu Ser His Lys Ser Gly Gly Glu Thr Ile Leu
    530                 535                 540


<210> SEQ ID NO 53
<211> LENGTH: 1605
<212> TYPE: DNA
<213> ORGANISM: Artificial Sequence
<220> FEATURE:
<223> OTHER INFORMATION: Recombinant Rabies Virus Glycoprotein GnRH-p3
<220> FEATURE:
<221> NAME/KEY: CDS
<222> LOCATION: (1)..(1605)

<400> SEQUENCE: 53

atg gtt cct cag gct ctc ctg ttt gta ccc ctt ctg gtt ttt cca ttg       48
Met Val Pro Gln Ala Leu Leu Phe Val Pro Leu Leu Val Phe Pro Leu
1               5                   10                  15

tgt ttt ggg aaa ttc cct att tac acg ata cca gac aag ctt ggt ccc       96
Cys Phe Gly Lys Phe Pro Ile Tyr Thr Ile Pro Asp Lys Leu Gly Pro
            20                  25                  30

tgg agt ccg att gac ata cat cac ctc agc tgc cca aac aat ttg gta      144
Trp Ser Pro Ile Asp Ile His His Leu Ser Cys Pro Asn Asn Leu Val
        35                  40                  45

gtg gag gac gaa gga tgc acc aac ctg tca ggg ttc tcc tac atg gaa      192
Val Glu Asp Glu Gly Cys Thr Asn Leu Ser Gly Phe Ser Tyr Met Glu
    50                  55                  60

ctt aaa gtt gga tac atc tta gcc ata aaa gtg aac ggg ttc act tgc      240
Leu Lys Val Gly Tyr Ile Leu Ala Ile Lys Val Asn Gly Phe Thr Cys
65                  70                  75                  80

aca ggc gtt gtg acg gag gct gaa acc tac act aac ttc gtt ggt tat      288
Thr Gly Val Val Thr Glu Ala Glu Thr Tyr Thr Asn Phe Val Gly Tyr
                85                  90                  95

gtc aca acc acg ttc aaa aga aag cat ttc cgc cca aca cca gat gca      336
Val Thr Thr Thr Phe Lys Arg Lys His Phe Arg Pro Thr Pro Asp Ala
            100                 105                 110

tgt aga gcc gcg tac aac tgg aag atg gcc ggt gac ccc aga tat gaa      384
Cys Arg Ala Ala Tyr Asn Trp Lys Met Ala Gly Asp Pro Arg Tyr Glu
        115                 120                 125

gag tct cta cac aat ccg tac cct gac tac cgc tgg ctt cga act gta      432
Glu Ser Leu His Asn Pro Tyr Pro Asp Tyr Arg Trp Leu Arg Thr Val
    130                 135                 140

aaa acc acc aag gag tct ctc gtt atc ata tct cca agt gtg gca gat      480
Lys Thr Thr Lys Glu Ser Leu Val Ile Ile Ser Pro Ser Val Ala Asp
145                 150                 155                 160

ttg gac cca tat gac aga tcc ctt cac tcg agg gtc ttc cct agc ggg      528
Leu Asp Pro Tyr Asp Arg Ser Leu His Ser Arg Val Phe Pro Ser Gly
                165                 170                 175

aag tgc tca gga gta gcg gtg tct tct acc tac tgc tcc act aac cac      576
Lys Cys Ser Gly Val Ala Val Ser Ser Thr Tyr Cys Ser Thr Asn His
            180                 185                 190

gat tac acc att tgg atg ccc gag aat ccg aga cta ggg atg tct tgt      624
Asp Tyr Thr Ile Trp Met Pro Glu Asn Pro Arg Leu Gly Met Ser Cys
        195                 200                 205

gac att ttt acc aat agt aga ggg aag aga gca tcc aaa gaa cac tgg      672
Asp Ile Phe Thr Asn Ser Arg Gly Lys Arg Ala Ser Lys Glu His Trp
    210                 215                 220

agc tac ggt ttg aga ccc ggg ggg agt gag act tgc ggc ttt gta gat      720
```

-continued

```
Ser Tyr Gly Leu Arg Pro Gly Gly Ser Glu Thr Cys Gly Phe Val Asp
225                 230                 235                 240

gaa aga ggc cta tat aag tct tta aaa gga gca tgc aaa ctc aag tta      768
Glu Arg Gly Leu Tyr Lys Ser Leu Lys Gly Ala Cys Lys Leu Lys Leu
                245                 250                 255

tgt gga gtt cta gga ctt aga ctt atg gat gga aca tgg gtc tcg atg      816
Cys Gly Val Leu Gly Leu Arg Leu Met Asp Gly Thr Trp Val Ser Met
            260                 265                 270

caa aca tca aat gaa acc aaa tgg tgc cct ccc gat aag ttg gtg aac      864
Gln Thr Ser Asn Glu Thr Lys Trp Cys Pro Pro Asp Lys Leu Val Asn
        275                 280                 285

ctg cac gac ttt cgc tca gac gaa att gag cac ctt gtt gta gag gag      912
Leu His Asp Phe Arg Ser Asp Glu Ile Glu His Leu Val Val Glu Glu
    290                 295                 300

ttg gtc agg aag aga gag gag tgt ctg gat gca cta gag tcc atc atg      960
Leu Val Arg Lys Arg Glu Glu Cys Leu Asp Ala Leu Glu Ser Ile Met
305                 310                 315                 320

aca acc aag tca gtg agt ttc aga cgt ctc agt cat tta aga aaa ctt     1008
Thr Thr Lys Ser Val Ser Phe Arg Arg Leu Ser His Leu Arg Lys Leu
                325                 330                 335

gtc cct ggg ttt gga aaa gca tat acc ata ttc aac aag acc ttg atg     1056
Val Pro Gly Phe Gly Lys Ala Tyr Thr Ile Phe Asn Lys Thr Leu Met
            340                 345                 350

gaa gcc gat gct cac tac aag tca gtc gaa act tgg aat gag atc ctc     1104
Glu Ala Asp Ala His Tyr Lys Ser Val Glu Thr Trp Asn Glu Ile Leu
        355                 360                 365

cct tca aaa ggg tgt tta aga gtt ggg ggg agg tgt cat cct cat gtg     1152
Pro Ser Lys Gly Cys Leu Arg Val Gly Gly Arg Cys His Pro His Val
    370                 375                 380

aac ggg gtg ttt ttc aat ggt ata ata tta gga cct gac ggc aat gtc     1200
Asn Gly Val Phe Phe Asn Gly Ile Ile Leu Gly Pro Asp Gly Asn Val
385                 390                 395                 400

tta atc cca gag atg caa tca tcc ctc ctc cag caa cat atg gag ttg     1248
Leu Ile Pro Glu Met Gln Ser Ser Leu Leu Gln Gln His Met Glu Leu
                405                 410                 415

ttg gaa tcc tcg gtt atc ccc ctt gtg cac ccc ctg gca gac ccg tct     1296
Leu Glu Ser Ser Val Ile Pro Leu Val His Pro Leu Ala Asp Pro Ser
            420                 425                 430

acc gtt ttc aag gac ggt gac gag gct gag gat ttt gtt gaa gtt cac     1344
Thr Val Phe Lys Asp Gly Asp Glu Ala Glu Asp Phe Val Glu Val His
        435                 440                 445

ctt ccc gat gtg cac aat cag gtc tca gga gtt gac ttg ggt ctc ccg     1392
Leu Pro Asp Val His Asn Gln Val Ser Gly Val Asp Leu Gly Leu Pro
    450                 455                 460

aac tgg ggg aag tat gta tta ctg agt gca ggg gcc ctg act gcc ttg     1440
Asn Trp Gly Lys Tyr Val Leu Leu Ser Ala Gly Ala Leu Thr Ala Leu
465                 470                 475                 480

atg ttg ata att ttc ctg atg aca tgt tgt aga aga gtc aat cga tca     1488
Met Leu Ile Ile Phe Leu Met Thr Cys Cys Arg Arg Val Asn Arg Ser
                485                 490                 495

gaa cct acg caa cac aat ctc aga ggg aca ggg agg gag gtg tca gtc     1536
Glu Pro Thr Gln His Asn Leu Arg Gly Thr Gly Arg Glu Val Ser Val
            500                 505                 510

act ccc caa agc ggg aag atc ata tct tca tgg gaa tca cac aag agt     1584
Thr Pro Gln Ser Gly Lys Ile Ile Ser Ser Trp Glu Ser His Lys Ser
        515                 520                 525

ggg ggt gag acc ata ctg taa                                         1605
Gly Gly Glu Thr Ile Leu
    530
```

<210> SEQ ID NO 54
<211> LENGTH: 534
<212> TYPE: PRT
<213> ORGANISM: Artificial Sequence
<220> FEATURE:
<223> OTHER INFORMATION: Synthetic Construct

<400> SEQUENCE: 54

```
Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr Arg Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Glu His Trp
    210                 215                 220

Ser Tyr Gly Leu Arg Pro Gly Gly Ser Glu Thr Cys Gly Phe Val Asp
225                 230                 235                 240

Glu Arg Gly Leu Tyr Lys Ser Leu Lys Gly Ala Cys Lys Leu Lys Leu
                245                 250                 255

Cys Gly Val Leu Gly Leu Arg Leu Met Asp Gly Thr Trp Val Ser Met
            260                 265                 270

Gln Thr Ser Asn Glu Thr Lys Trp Cys Pro Pro Asp Lys Leu Val Asn
        275                 280                 285

Leu His Asp Phe Arg Ser Asp Glu Ile Glu His Leu Val Val Glu Glu
    290                 295                 300

Leu Val Arg Lys Arg Glu Glu Cys Leu Asp Ala Leu Glu Ser Ile Met
305                 310                 315                 320

Thr Thr Lys Ser Val Ser Phe Arg Arg Leu Ser His Leu Arg Lys Leu
                325                 330                 335

Val Pro Gly Phe Gly Lys Ala Tyr Thr Ile Phe Asn Lys Thr Leu Met
            340                 345                 350

Glu Ala Asp Ala His Tyr Lys Ser Val Glu Thr Trp Asn Glu Ile Leu
        355                 360                 365

Pro Ser Lys Gly Cys Leu Arg Val Gly Gly Arg Cys His Pro His Val
    370                 375                 380
```

```
Asn Gly Val Phe Phe Asn Gly Ile Ile Leu Gly Pro Asp Gly Asn Val
385                 390                 395                 400

Leu Ile Pro Glu Met Gln Ser Ser Leu Leu Gln Gln His Met Glu Leu
                405                 410                 415

Leu Glu Ser Ser Val Ile Pro Leu Val His Pro Leu Ala Asp Pro Ser
            420                 425                 430

Thr Val Phe Lys Asp Gly Asp Glu Ala Glu Asp Phe Val Glu Val His
        435                 440                 445

Leu Pro Asp Val His Asn Gln Val Ser Gly Val Asp Leu Gly Leu Pro
    450                 455                 460

Asn Trp Gly Lys Tyr Val Leu Leu Ser Ala Gly Ala Leu Thr Ala Leu
465                 470                 475                 480

Met Leu Ile Ile Phe Leu Met Thr Cys Cys Arg Arg Val Asn Arg Ser
                485                 490                 495

Glu Pro Thr Gln His Asn Leu Arg Gly Thr Gly Arg Glu Val Ser Val
            500                 505                 510

Thr Pro Gln Ser Gly Lys Ile Ile Ser Ser Trp Glu Ser His Lys Ser
        515                 520                 525

Gly Gly Glu Thr Ile Leu
    530


<210> SEQ ID NO 55
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 55

Cys Glu His Trp Ser Tyr Gly Leu Arg Pro Gly
1               5                   10


<210> SEQ ID NO 56
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 56

Cys Glu His Trp Ser Tyr Gly Leu Arg Pro Gly Glu His Trp Ser Tyr
1               5                   10                  15

Gly Leu Arg Pro Gly
            20


<210> SEQ ID NO 57
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 57

gaacactgga gctacggttt gagacccggg gaacactgga gctacggttt gagacccggg     60


<210> SEQ ID NO 58
<211> LENGTH: 69
<212> TYPE: DNA
<213> ORGANISM: Artificial Sequence
<220> FEATURE:
<223> OTHER INFORMATION: Synthetic oligonucleotide
```

<400> SEQUENCE: 58
ccaacctgtc agggttctcc gaacactgga gctacggttt gagacccggg tacatggaac 60
ttaaagttg 69

<210> SEQ ID NO 59
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 59
ggagaaccct gacaggttgg tgcatccttc gtcctccac 39

<210> SEQ ID NO 60
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 60
ggtttttcca ttgtgttttg gggaacactg gagctacggt ttgagacccg gggaacactg 60
gagctacggt ttgagacccg ggaaattccc tatttacacg 100

<210> SEQ ID NO 61
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 61
cccaaaacac aatggaaaaa ccagaagggg tacaaacagg 40

<210> SEQ ID NO 62
<211> LENGTH: 1319
<212> TYPE: DNA
<213> ORGANISM: Canis familiaris

<400> SEQUENCE: 62
ggttaccagt gggagtgact ggaggagcta tggggctgag ctatggaatt ttcatctgtt 60
ttctgctcct gggaggcatg gagctgtgct gcccccagac catctggcca actgagacct 120
actacccatt gacatctagg cccccagtaa tggtggactg tctggagtcc cagctggtgg 180
tcactgtcag caaagacctt tttggtactg ggaagctcat caggccagca gacctcaccc 240
tgggtccaga gaactgtgag cccctggtct ccatggacac ggatgatgtg gtcaggtttg 300
aggttgggct gcacgagtgt ggcagcaggg tgcaggtgac tgacaatgct ctggtgtaca 360
gcaccttcct gatccacagc cccgccctg cgggcaacct gtccatcctg agaactaatc 420
gtgccgaggt ccccatcgag tgccactacc ccaggcacag caatgtgagc agccaggcca 480
tcctgcccac ttgggtgccc ttcaggacca caatgctctt cgaggagaag ctagttttct 540
ctctccgcct aatggaggag gactggggct ccgagaagca atcccccaca ttccagctgg 600
gagacatagc ccacctccag gctgaagtcc acactggcag ccatatgcca ctgcgacttt 660
ttgtggacca ctgtgtggcc acgctgacac cagatcggaa tgccttccct catcacaaaa 720
ttgtggactt ccatggctgt cttgtggatg gtctctacaa ttcctcttca gccttcaaag 780
cccccagacc caggccagag actcttcagt tcacagtgga tgttttccac tttgctaagg 840
actcaagaaa cacgatctat atcacctgcc atctgaaggt cactccggct gaccgagtcc 900
cagaccagct aaacaaagct tgttccttca tcaagtctac caagaggtcc taccctgtag 960
aaggctcggc tgatatttgt cgctgttgta acaaaggcag ctgtggcctt ccaggccggt 1020
ccaggaggct gtcccaccta gagagagggt ggcgcaggtc tgtttcccac actagaaatc 1080
gcaggcacgt gactgaagaa gcagagatca ccgtggggcc tctgatcttc ctgggaaagg 1140
ctagtgatca tggtatagag gggtcaacct ctcctcacac ctctgtgatg ttgggcttag 1200
gcctggccac ggtggtatcc ctgactctag ctaccattgt cctggtcctt gccaagaggc 1260
atcgtactgc ttcccaccct gtgatatgcc ctgcatctgt ctcccaataa agaataagc 1319

<210> SEQ ID NO 63
<211> LENGTH: 1602
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: (1)..(1602)
<220> FEATURE:
<221> NAME/KEY: misc_feature
<222> LOCATION: (1054)..(1056)
<223> OTHER INFORMATION: n is a, c, g, or t

<400> SEQUENCE: 63

```
atg gtt cct cag gct ctc ctg ttt gta ccc ctt ctg gtt ttt cca ttg       48
Met Val Pro Gln Ala Leu Leu Phe Val Pro Leu Leu Val Phe Pro Leu
1               5                   10                  15

tgt ttt ggg aaa ttc cct att tac acg ata cca gac aag ctt ggt ccc       96
Cys Phe Gly Lys Phe Pro Ile Tyr Thr Ile Pro Asp Lys Leu Gly Pro
            20                  25                  30

tgg agc ccg att gac ata cat cac ctc agc tgc cca aac aat ttg gta      144
Trp Ser Pro Ile Asp Ile His His Leu Ser Cys Pro Asn Asn Leu Val
        35                  40                  45

gtg gag gac gaa gga tgc acc aac ctg tca ggg ttc tcc tac atg gaa      192
Val Glu Asp Glu Gly Cys Thr Asn Leu Ser Gly Phe Ser Tyr Met Glu
    50                  55                  60

ctt aaa gtt gga tac atc tta gcc ata aaa atg aac ggg ttc act tgc      240
Leu Lys Val Gly Tyr Ile Leu Ala Ile Lys Met Asn Gly Phe Thr Cys
65                  70                  75                  80

aca ggc gtt gtg acg gag gct gaa acc tat act aac ttc gtt ggt tat      288
Thr Gly Val Val Thr Glu Ala Glu Thr Tyr Thr Asn Phe Val Gly Tyr
                85                  90                  95

gtc aca acc acg ttc aaa aga aag cat ttc cgc cca aca cca gat gca      336
Val Thr Thr Thr Phe Lys Arg Lys His Phe Arg Pro Thr Pro Asp Ala
            100                 105                 110

tgt aga gcc gcg tac aac tgg aag atg gcc ggt gac ccc aga tat gaa      384
Cys Arg Ala Ala Tyr Asn Trp Lys Met Ala Gly Asp Pro Arg Tyr Glu
        115                 120                 125

gag tct cta cac aat ccg tac cct gac tac cac tgg ctt cga act gta      432
Glu Ser Leu His Asn Pro Tyr Pro Asp Tyr His Trp Leu Arg Thr Val
    130                 135                 140

aaa acc acc aag gag tct ctc gtt atc ata tct cca agt gtg gca gat      480
Lys Thr Thr Lys Glu Ser Leu Val Ile Ile Ser Pro Ser Val Ala Asp
145                 150                 155                 160

ttg gac cca tat gac aga tcc ctt cac tcg agg gtc ttc cct agc ggg      528
Leu Asp Pro Tyr Asp Arg Ser Leu His Ser Arg Val Phe Pro Ser Gly
                165                 170                 175

aag tgc tca gga gta gcg gtg tct tct acc tac tgc tcc act aac cac      576
Lys Cys Ser Gly Val Ala Val Ser Ser Thr Tyr Cys Ser Thr Asn His
            180                 185                 190
```

-continued

```
gat tac acc att tgg atg ccc gag aat ccg aga cta ggg atg tct tgt      624
Asp Tyr Thr Ile Trp Met Pro Glu Asn Pro Arg Leu Gly Met Ser Cys
        195                 200                 205

gac att ttt acc aat agt agg ggg aag aga gca tcc aaa ggg agt gag      672
Asp Ile Phe Thr Asn Ser Arg Gly Lys Arg Ala Ser Lys Gly Ser Glu
    210                 215                 220

act tgc ggc ttt gta gat gaa aga ggc cta tat aag tct tta aaa gga      720
Thr Cys Gly Phe Val Asp Glu Arg Gly Leu Tyr Lys Ser Leu Lys Gly
225                 230                 235                 240

gca tgc aaa ctc aag tta tgt gga gtt cta gga ctt aga ctt atg gat      768
Ala Cys Lys Leu Lys Leu Cys Gly Val Leu Gly Leu Arg Leu Met Asp
                245                 250                 255

gga aca tgg gtc gcg atg caa aca tca aat gaa acc aaa tgg tgc ccc      816
Gly Thr Trp Val Ala Met Gln Thr Ser Asn Glu Thr Lys Trp Cys Pro
            260                 265                 270

ccc gat cag ttg gtg aac ctg cac gac ttt cgc tca gac gaa att gag      864
Pro Asp Gln Leu Val Asn Leu His Asp Phe Arg Ser Asp Glu Ile Glu
        275                 280                 285

cac ctt gtt gta gag gag ttg gtc agg aag aga gag gag tgt ctg gat      912
His Leu Val Val Glu Glu Leu Val Arg Lys Arg Glu Glu Cys Leu Asp
    290                 295                 300

gca cta gag tcc atc atg aca acc aag tca gtg agt ttc aga cgt ccc      960
Ala Leu Glu Ser Ile Met Thr Thr Lys Ser Val Ser Phe Arg Arg Pro
305                 310                 315                 320

agt cat tta aga aaa ctt gtc cct ggg ttt gga aaa gca tat acc ata     1008
Ser His Leu Arg Lys Leu Val Pro Gly Phe Gly Lys Ala Tyr Thr Ile
                325                 330                 335

ttc aac aag acc ttg atg gaa gcc gat gct cac tac aag tca gtc nnn     1056
Phe Asn Lys Thr Leu Met Glu Ala Asp Ala His Tyr Lys Ser Val Xaa
            340                 345                 350

act tgg aat gag atc ctc cct tca aaa ggg tgt tta aga gtt ggg ggg     1104
Thr Trp Asn Glu Ile Leu Pro Ser Lys Gly Cys Leu Arg Val Gly Gly
        355                 360                 365

agg tgt cat cct cat gtg aac ggg gtg ttt ttc aat ggt ata ata tta     1152
Arg Cys His Pro His Val Asn Gly Val Phe Phe Asn Gly Ile Ile Leu
    370                 375                 380

gga cct gac ggc aat gtc tta atc cca gag atg caa tca tcc ctc ctc     1200
Gly Pro Asp Gly Asn Val Leu Ile Pro Glu Met Gln Ser Ser Leu Leu
385                 390                 395                 400

cag caa cat atg gag ttg ttg gaa tcc tcg gtt atc ccc ctt gtg cac     1248
Gln Gln His Met Glu Leu Leu Glu Ser Ser Val Ile Pro Leu Val His
                405                 410                 415

ccc ctg gca gac ccg tct acc gtt ttc aag gac ggt gac gag gct gag     1296
Pro Leu Ala Asp Pro Ser Thr Val Phe Lys Asp Gly Asp Glu Ala Glu
            420                 425                 430

gat ttt gtt gaa gtt cac ctt ccc gat gtg cac aat cag gtc tca gga     1344
Asp Phe Val Glu Val His Leu Pro Asp Val His Asn Gln Val Ser Gly
        435                 440                 445

gtt gac ttg ggt ctc ccg aac tgg ggg aag gaa cac tgg agc tac ggt     1392
Val Asp Leu Gly Leu Pro Asn Trp Gly Lys Glu His Trp Ser Tyr Gly
    450                 455                 460

ttg aga ccc ggg tat gta tta ctg agt gca ggg gcc ctg act gcc ttg     1440
Leu Arg Pro Gly Tyr Val Leu Leu Ser Ala Gly Ala Leu Thr Ala Leu
465                 470                 475                 480

atg ttg ata att ttc ctg atg aca tgt tgt aga aga gtc aat cga tca     1488
Met Leu Ile Ile Phe Leu Met Thr Cys Cys Arg Arg Val Asn Arg Ser
                485                 490                 495

gaa cct acg caa cac aat ctc aga ggg aca ggg agg gag gtg tca gtc     1536
Glu Pro Thr Gln His Asn Leu Arg Gly Thr Gly Arg Glu Val Ser Val
            500                 505                 510
```

```
act ccc caa agc ggg aag atc ata tct tca tgg gaa tca cac aag agt     1584
Thr Pro Gln Ser Gly Lys Ile Ile Ser Ser Trp Glu Ser His Lys Ser
        515                 520                 525

ggg ggt gag acc aga ctg                                             1602
Gly Gly Glu Thr Arg Leu
    530


<210> SEQ ID NO 64
<211> LENGTH: 534
<212> TYPE: PRT
<213> ORGANISM: Artificial Sequence
<220> FEATURE:
<221> NAME/KEY: misc_feature
<222> LOCATION: (352)..(352)
<223> OTHER INFORMATION: The 'Xaa' at location 352 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 64

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
```

-continued

```
    290                 295                 300

Ala Leu Glu Ser Ile Met Thr Thr Lys Ser Val Ser Phe Arg Arg Pro
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Xaa
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Glu His Trp Ser Tyr Gly
    450                 455                 460

Leu Arg Pro Gly Tyr Val Leu Leu Ser Ala Gly Ala Leu Thr Ala Leu
465                 470                 475                 480

Met Leu Ile Ile Phe Leu Met Thr Cys Cys Arg Arg Val Asn Arg Ser
                485                 490                 495

Glu Pro Thr Gln His Asn Leu Arg Gly Thr Gly Arg Glu Val Ser Val
            500                 505                 510

Thr Pro Gln Ser Gly Lys Ile Ile Ser Ser Trp Glu Ser His Lys Ser
        515                 520                 525

Gly Gly Glu Thr Arg Leu
    530
```